(12) United States Patent
Coull et al.

(10) Patent No.: US 6,962,778 B1
(45) Date of Patent: *Nov. 8, 2005

(54) METHODS, KITS AND COMPOSITIONS FOR SUPPRESSING THE BINDING OF DETECTABLE PROBES TO NON-TARGET SEQUENCES IN HYBRIDIZATION ASSAYS

(75) Inventors: James M. Coull, Westford, MA (US); Jens J. Hyldig-Nielson, Holliston, MA (US); Sven E. Godtfredsen, Værløse (DK); Mark J. Fiandaca, Acton, MA (US); Kyriaki Stefano, Hopkinton, MA (US)

(73) Assignee: Boston Probes, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/545,084

(22) Filed: Apr. 7, 2000

Related U.S. Application Data

(63) Continuation of application No. 08/963,472, filed on Nov. 3, 1997, now Pat. No. 6,110,676, which is a continuation-in-part of application No. 08/927,709, filed on Sep. 25, 1997, now abandoned.

(51) Int. Cl.[7] ............................ C12Q 1/68; C12P 19/34; C07H 21/02
(52) U.S. Cl. .................. 435/6; 435/91.2; 536/23.1; 536/24.3
(58) Field of Search .................. 435/6, 91.2; 536/23.1, 536/24.3

(56) References Cited

U.S. PATENT DOCUMENTS

| | | | |
|---|---|---|---|
| 4,851,330 A | 7/1989 | Kohne | |
| 5,030,577 A | 7/1991 | Genna et al. | |
| 5,200,313 A | 4/1993 | Carrico et al. | |
| 5,288,611 A | 2/1994 | Kohne | |
| 5,387,510 A | 2/1995 | Wu | |
| 5,410,068 A | 4/1995 | Coull et al. | |
| 5,434,047 A | 7/1995 | Arnold | |
| 5,447,841 A | 9/1995 | Gray et al. | |
| 5,527,675 A | 6/1996 | Coull et al. | |
| 5,539,082 A | 7/1996 | Nielsen et al. | |
| 5,567,587 A | 10/1996 | Kohne | |
| 5,578,458 A | 11/1996 | Caskey et al. | |
| 5,582,970 A | 12/1996 | Wallace | |
| 5,601,984 A | 2/1997 | Kohne | |
| 5,612,183 A | 3/1997 | Kohne | |
| 5,612,458 A | 3/1997 | Hyldig-Nielsen et al. | |
| 5,623,049 A | 4/1997 | L obberding et al. | |
| 5,641,625 A | 6/1997 | Ecker et al. | |
| 5,641,631 A | 6/1997 | Kohne | |
| 5,641,632 A | 6/1997 | Kohne | |
| 5,656,427 A | 8/1997 | Hammond et al. | |
| 5,656,461 A | 8/1997 | Demers | |
| 5,691,141 A | 11/1997 | Koster et al. | |
| 5,712,386 A | 1/1998 | Wang et al. | |
| 5,714,331 A | 2/1998 | Buchardt, et al. | |
| 5,723,294 A | 3/1998 | Glass et al. | |
| 5,723,296 A | 3/1998 | Nycz et al. | |
| 5,753,444 A | 5/1998 | Wu | |
| 5,756,696 A | 5/1998 | Gray | |
| 5,824,476 A | 10/1998 | Wallace | |
| 5,849,483 A | 12/1998 | Shuber | |
| 5,985,563 A | 11/1999 | Hyldig-Nielsen et al. | 435/6 |

FOREIGN PATENT DOCUMENTS

| | | |
|---|---|---|
| EP | 0304184 | 7/1988 |
| EP | 0546590 A1 | 9/1992 |
| EP | 0333465 B1 | 7/1994 |
| EP | 0 611 876 A1 | 8/1994 |
| EP | 0725148 A2 | 11/1995 |
| WO | WO98/20166 | 5/1998 |

OTHER PUBLICATIONS

Aich, P. et al, Fast kinetic studies by fluorescence correlation spectroscopy of PNA–DNA interactions. Nucleosides & Nucleotides, 16(5&6), 609–615 (May/Jun., 1997).

Almarsson, O. et al, Molecular mechanics calculations of the structures of polyamide nucleic acid DNA duplexes and triple helical hybrids. Proc. Natl. Acad. Sci., U.S.A. 90, 7518–7522 (1993).

Almarsson, É. et al, Peptide nucleic acid (PNA) conformation and polymorphism in PNA–DNA and PNA–RNA hybrids. Proc. Natl. Acad. Sci., U.S.A. 90, 9542–9546 (1993).

Altmann, K–H. et al, polyamide based nucleic acid analogs—synthesis of δ–amino acids with nucleic acid bases bearing side chains. Bioorg. & Med Chem Lett, 7, 9, 1119–1122 (May, 1997).

Amado, F.M.L. et al, Analysis of Peptide and Protein Samples Containing Surfactants by MALDI–MS. Anal. Chem. 69, 1102–1106 (Mar., 1997).

Basu, S. et al, An efficient method for improving the cellular uptake of peptide nucleic acids. FASEB J 10, A446 Abstract #2574 (1996).

(Continued)

*Primary Examiner*—Jeffrey Fredman
(74) *Attorney, Agent, or Firm*—Brian D. Gildea

(57) ABSTRACT

This invention relates to methods, kits and compositions suitable for the improved detection, analysis and quantitation of nucleic acid target sequences using probe based hybridization assays. The invention is more specifically directed to methods, kits and compositions suitable for suppressing the binding of detectable nucleic acid probes or detectable PNA probes to non-target nucleic acid sequences in an assay for a target nucleic acid sequence to thereby improve the reliability, sensitivity and specificity of the assay. The methods, kits and compositions of this invention are particularly well suited to the detection and analysis of nucleic acid point mutations.

41 Claims, 19 Drawing Sheets

OTHER PUBLICATIONS

Bentin, T. et al, Enhanced Peptide Nucleic Acid binding to supercoiled DNA: Possible implications for DNA ñbreathingi dynamics. Biochemistry 35, 8863–8869 (1996).

Bergmann, F. et al, Solid phase synthesis of directly linked PNA–DNA–hybrids. Tetrahedron Lett. 36, 6823–6826 (1995).

Betts, L. et al, A nucleic acid triple helix formed by a peptide nucleic acid–DNA complex. Science 270, 1838–1841 (1995).

Betts, L. et al, Crystal Structure of a Nucleic Acid Triplex at 2.5□: A Peptide Nucleic Acid: DNA Complex. Abstract from Ninth Conversation in Biomolecular Stereodynamics, Jun. 20–24, 1995, a020 (1995).

Bigey, P. et al, DNA binding and cleavage by a cationic manganese porphyrin—peptide nucleic acid conjugate, Bioconjugate Chem. 8, 267–70 (May/Jun., 1997).

Boado, R.J., Antisense drug delivery through the blood–brain barrier. Adv. Drug Deliv. Rev. 15, 73–107 (1995).

Boffa, L.C. et al, Isolation of active genes containing CAG repeats by DNA strand invasion by a peptide nucleic acid. Proc. Natl. Acad. Sci., U.S.A. 92, 1901–1905 (1995).

B?hler, C. et al, Template switching between PNA and RNA oligonucleotides. Nature 376, 578–581 (1995).

Bonham, M.A. et al, An assessment of the antisense properties of Rnase H–competent and steric–blocking oligomers. Nucleic Acids Res. 23, 1197–1203 (1995).

Breipohl, G. et al, Synthesis of Polyamide Nucleic Acids (PNAs) using a novel Fmoc/MmT protecting–group combination. Bioorgan. Med. Chem. Lett. 6, 665–670 (1996).

Brown, S.C. et al, NMR solution structure of a peptide nucleic acid complexed with RNA. Science 265, 777–780 (1994).

Buchardt, O. et al, Peptide nucleic acids and their potential applications in biotechnology. TIBTECH. 11, 384–386 (1993).

Buchardt, O. et al, The use of nucleic acid analogues in diagnostics and analytical procedures. WO 92/20703 (Nov. 26, 1992).

Buchardt, O. et al, Peptide Nucleic Acids. WO 92/20702 (Nov. 26, 1992).

Butler, J.M. et al, Peptide Nucleic Acid Characterization by MALDI–TOF Mass Spectrometry. Anal. Chem. 68, 3283–3287 (Sep. 1996).

Carlsson, C. et al, Rapid Detection of Single–Base Substitution by PNA–DNA Hybridization Capillary Electrophoresis. Nature 380, 207 (Mar., 1996).

Chen, S.–M. et al, Molecular dynamics and NMR studies of single–stranded PNAs. Tetrahedron Lett. 35, 5105–5108 (1994).

Cherny, D.Y. et al, DNA unwinding upon strand–displacement of binding of thymine–substituted polyamide to double–stranded DNA. Proc. Natl. Acad. Sci., U.S.A. 90, 1667 (1993).

Cherney, D.I. et al, Electron Microscopic studies of sequence–specific recognition of duplex DNA by different ligands. J. Mol. Recog. 7, 171–176 (1994).

Christensen, L. et al, Improved synthesis, purification and characterization of PNA oligomers. 3rd Solid Phase Symposium, Oxford, UK, 149 (Aug. 31–Sep. 4, 1994).

Christensen, L. et al, Solid–phase Synthesis of Peptide Nucleic Acids. Journal of Peptide Science 3, 175–183 (1995).

Clivio, P. et al, A photochemical approach to highlight backbone effects in PNA. J. Am. Chem. Soc. 119, 5255–5256 (Jun., 1997).

Cohen, J., Getting all turned around over the origins of life on earth. Science 267, 1265–1266 (1995).

Colainni, S.E.M. et al, Raman spectroscopic studies of some biochemically relevant molecules. Vib. Spect. 9, 111–120 (1995).

Corey, D.R., 48000–fold acceleration of Hybridization by Chemically Modified Oligonucleotides. J. Am. Chem. Soc. 117, 9373–9374 (1995).

Corey, D.R. et al, Accleration hybridization of Peptide Nucleic Acid oligomers to targetted sequences within duplex DNA. FASEB Journal 9, A1391 (1995).

Danheiser, S.L., Peptide Nucleic Acids Raise Biotech Firms'interest as potential drugs and diagnostics, Gen. Eng. News 13, pp. 1, 22 + 23 (1993).

Demers, D.B. et al, Enhanced PCR amplification of VNTR locus D1S80 using peptide nucleic acid (PNA). Nucleic Acids Res. 23, 3050–3055 (1995).

Demers, D.B. et al, Enhanced PCR amplification of VNTR loci using Peptide Nucleic Acids. Am. J. Hum. Gen. Abstract (1996).

Demidov, V. et al, Sequence selective double strand DNA cleavage by PNA targeting using nuclease S1. Nucleic Acids Res. 21, 2103–2107 (1993).

Demidov, V. et al, Stability of peptide nucleic acids in human serum and cellular extracts. Biochem. Pharmacol. 48, 1310–1313 (1994).

Demidov, V.V. et al, Complexes of duplex DNA with homopyrimidine Peptide Nucleic Acid (PNA). J. Biomolec. Struct. Dyn. 12, A042 (1995).

Demidov, V.V. et al, Electron Microscopy mapping of oligopurine tracts in duplex DNA by Peptide Nucleic Acid targetting. Nucleic Acids Res. 22, 5218–5222 (1994).

Demidov, V.V. et al, Kinetics and mechanism of polyamide (ñpeptidei) nucleic acid binding to duplex DNA. Proc. Natl. Acad. Sci., U.S.A. 92, 2637–2641 (1995).

Diderichsen, U. et al, Self–Pairing PNA with alternating alanyl/homoalanyl backbone. Tetrahedron Lett. 37, 475–478 (1996).

Diederichsen, U. Alanyl–PNA oligomers: a new system for intercalation. Bioogranic & Med Chem Lett 7, 13, 1743–1746 (Jul., 1997).

Dueholm, K. et al, An efficient synthesis of Boc–aminoacetaldehyde and its application to the synthesis of N–(2–Bocaminoethyl)glycine esters. Org. Prep. & Proc., Int. 25, 457–461 (1993).

Dueholm, K.L. et al, Chemistry, properties and applications of PNA. New J. Chem. 21, 19–31 (Jan., 1997).

Dueholm, K.L. et al, Peptide Nucleic Acid (PNA) with a chiral backbone based on alanine. Bioorg. & Med. Chem. Lett. 4, 1077–1080 (1994).

Dueholm, K.L. et al, Synthesis of Peptide Nucleic Acid Monomers containing the four natural nucleobases: Thymine, Cytosine, Adenine, and Guanine and their oligomerization. J. Org. Chem. 59, 5767–5773 (1994).

Egholm, M. et al, Efficient pH–independent sequence–specific DNA binding by pseudoisocytosine–containing bis–PNA. Nucleic Acids Res. 23, 217–222 (1995).

Egholm, M. et al, Peptide nucleic acids (PNA): Oligonucleotide analogues with an achiral peptide backbone. J. Am. Chem. Soc. 114, 1895–1897 (1992).

Egholm, M. et al, Peptide nucleic acids containing adenine or guanine recognize thymine and cytosine in complementary DNA sequences. J. Chem. Soc., Commun. 800–801 (1993).

Egholm, M. et al, PNA hybridizes to complementary oligonucleotides obeying the Watson–Crick hydrogen bonding rules. Nature 365, 566–568 (1993).

Egholm, M. et al, Recognition of guanine and adenine in DNA by cytosine and thymine containing peptide nucleic acids. J. Am. Chem. Soc. 114, 9677–9678 (1992).

Eriksson, M. et al, PNA–nucleic acid complexes. Structure, stability and dynamics. Quarterly Review of Biophysics, 29, 369–394 (1996).

Eriksson, M. et al, Solution structure of a peptide nucleic acid–DNA duplex. Nature Structural Biology 3, 410–413 (May, 1996).

Eriksson, M., Structure of PNA–nucleic acid complexes. Nucleosides & Nucleotides 16(5&6), 617–621 (May/Jun., 1997).

Finn, P.J. et al, Synthesis and properties of DNA –PNA chirmeric oligomers. Nucleic Acids Res. 24, 3357–3363 (1996).

Flam, F., Can DNA Mimics Improve on the real thing? Science 262, 1647–1649 (1993).

Flensburg, C. et al, Ethyl 9–Adeninylacetate at 122 K. Acta Crystallogr. C50, 1480–1482 (1994).

Footer, M. et al, Biochemical evidence that a D–loop is part of a four stranded PNA–DNA bundle. Nickel–Mediated cleavage of duplex DNA by a Gly–Gly–His Bis–PNA. Biochemistry 35, 10673–10679 (1996).

Frank–Kamenetskii, M.D. et al, Triplex DNA structures, Annu. Rev. Biochem. 64, 65–95 (1995).

Fujii, M. et al, Nucleic acid analog peptide (NAAP) 2, syntheses and properties of novel DNA analog peptides containing nucleobase linked β–aminoalanine. Bioorg. & Med. Chem. Lett. 7, 637–640 (Mar., 1997).

Gambacorti–Passerini, C. et al, In vitro transcription and translation inhibition by anti–promyelocytic leukemia (PML)/Retinoic acid receptor α and anti–PML Peptide Nucleic Acid. Blood 88, 1411–1417 (Aug., 1996).

Goodnow, R.A. et al, Oligomer synthesis and DNA/RNA recognition properties of a novel oligonucleotid backbone analog: glucopyranosyl nucleic amide (GNA), Tett Lett 38, 18, 3190–3202 (May, 1997).

Goodnow, R.A. Jr. et al, Synthesis of thymine, cytosine, adenine, and guanine containing N–Fmoc protected amino acids: building blocks for construction of novel oligonucleotide backbone analogs, Tett Lett 38, 18, 3195–3198 (May, 1997).

Griffith, M.C. et al, Single and Bis Peptide Nucleic Acids as triplexing agents: Binding and stoichiometry. J. Am. Chem. Soc. 117, 831–832 (1995).

Guo, Z. Enhanced discrimination of single nucleotide polymorphisms by artificial mismatch hybridization. Nature Biotech. 15, 331–335 (Apr., 1997).

Haaima, G. et al, Peptide Nucleic Acids (PNA) containing thymine monomers derived from chiral amino acids: Hybridization & solubility properties of D–Lysine PNA. Angew. Chem. Int. Engl. 35, 1939–1941 (1996).

Hamilton, S.E. et al, Specific and nonspecific inhibition of transcription by DNA, PNA, and phosphorothioate promoter analog duplexes. Bioorg. Med. Chem. Lett. 6, 2897–2900 (1996).

Hanvey, L.C. et al, Antisense and antigene properties of peptide nucleic acids. Science 258, 1481–1485 (1992).

Howarth, N.M. et al, α–PNA: A novel peptide nucleic acid analogue of DNA. J. Org. Chem. 62, 5441–5450 (Aug., 1997).

Hyldig–Nielsen, J. et al, Polyclonal antibody to PNA/ Nucleic acid complexes. WO 95/17430 (Jun. 29, 1995).

Hyldig–Nielson, et al, PNA probes for detection of *neisseria gonorrhoeae* and *chlamydia trachomatis*. WO 95/32305 (Nov. 30, 1995).

Hyrup, B. et al, A flexible and positively charged PNA analogue with an ethylene–linker to the nucleobase: Synthesis and hybridization properties. Bioorg. Med. Chem. Lett. 6, 1083–1088 (1996).

Hyrup, B. et al, Peptide Nucleic Acids (PNA): Synthesis, Properties and Potential Applications. Bioorg. Med. Chem. 4, 5–23 (1996).

Hyrup, B. et al, Peptide Nucleic Acids with extended backbones. J. Chem. Soc., Chem. Commun. 518–519 (1993).

Hyrup, B. et al, Structure–Activity studies of the binding modified Peptide Nucleic Acids to DNA. J. Am. Chem. Soc. 116, 7964–7970 (1994).

Iyer, M. et al, Accelerated Hybridization of Oligonucleotides to Duplex DNA. The J. of Biol. Chem. 270, 14712–14717 (1995).

Jankowsky, E. et al, Peptide nucleic acid (PNA) is capable of enhancing hammerhead ribozyme activity with long but not with short RNA substrates. Nucl. Acids Res. 25, 14, 2690–2693 (Jul., 1997).

Jensen, K.K. et al, Kinetics for hybridization of peptide nucleic acids (PNA) with DNA and RNA studies with the BIAcore technique. Biochemistry 36, 5072–5077 (Apr., 1997).

Jordan, S. et al, New hetero–oligomeric peptide nucleic acids with improved binding properties to complementary DNA. Bioorg. & Med. Chem. Lett. 7, 687–690 (Mar., 1997).

Jordan, S. et al, Synthesis of new building blocks for peptide nucleic acids containing monomers with variations in the backbone. Bioorg. & Med. Chem. Lett. 7, 681–688 (Mar., 1997).

Jurinke, C. et al, Recovery of Nucleic Acids from Immobilized Biotin–Streptavidin Complexes Using Ammonium Hydroxide and Applications in MALDI–TOF Mass Spectrometry. Anal. Chem. 69, 904–910 (Mar., 1997).

Kastrup, J.S. et al, Crystalization and preliminary X–ray analysis of a PNA–DNA complex. FEBS Lett. 363, 115–117 (1995).

Kennel, D.E. Principles and Practices of Nucleic Acid Hybridization, pp 259–301. source unknown.

Kim, S.K. et al, Right–handed triplex formed between Peptide Nucleic Acid PNA–T8 and Poly(dA) shown by linear and circular dichroism spectroscopy. J. Am. Chem. Soc. 115, 6477–6481 (1993).

Knudsen, H. et al, Antisense properties of duplex– and triplex– forming PNAs. Nucleic Acids Res. 24, 494–500 (1996).

Koch, T. et al, PNA–Peptide Chimerae. Tetrahedron Lett. 36, 6933–6936 (1995).

Krasil'nikova, M.M. et al, Enhancing the specificity of peptide–nucleic acid binding with DNA. Molecular Biology, 30, 226–230 (1996).

Krotz, A.H. et al, Synthesis of ñRetro–inversoî Peptide Nucleic Acids: 1. Characterization of the monomers. Tetrahedron Lett. 36, 6937–6940 (1995).

Krotz, A.H. et al, Synthesis of ñRetro–inversoîPeptide Nucleic Acids: 2. Oligomerization and stability. Tetrahedron Lett. 36, 6941–6944 (1995).

Lagiffoul, P.–H. et al, The synthesis, co–oligomerization and hybridization of a thymine–thymine heterodimer containing PNA. Bioorg. & Med. Chem. Lett. 4, 1081–1082 (1994).

Lansdorp, P.M. et al, Heterogeneity in telomere length of human chromosomes. Human Mol. Gen. 5, 685–691 (1996).

Larsen, H.J. et al, Transcription–mediated binding of peptide nucleic acid (PNA) to double–stranded DNA: Sequence–specific suicide transcription. Nucleic Acids Res. 24, 458–463 (1996).

Leijon, M. et al, Structural Characterization of PNA–DNA Duplexes by NMR. Evidence for DNA in a B–like Conformation. Biochemistry 33, 9820–9825 (1994).

Leijon, M. et al, Unique base–pair breathing dynamics in PNA–DNA hybrids. J. Mol. Bio. 271, 438–455 (Aug., 1997).

Lenzi, A. et al, Synthesis of N–Boc–α–amino acids with nucleobase residues as building blocks for the preparation of chiral PNA (Peptide Nucleic Acids). Tetrahedron Lett. 36, 1713–1716 (1995).

Lesnik, E.A. et al, Evaluation of pyrimidine PNA binding to ssDNA targets from nonequilibrium melting experiments. Nucl. Acids. Res. 25, 568–574 (Feb., 1997).

Lester, Ane. PNA Array Technology. Presented at Biochip Technologies Conference in Annapolis, Oct. 1997.

Lohse, J. et al, Sequence selective DNA cleavage by PNA–NTA conjugates in DNA and RNA Cleavers and Chemotherapy of Cancer and Viral Diseases; B. Meunier, Ed.; Kluwr Academic Publishers: 133–141 (1996).

Lowe, G. et al, Amino Acids bearing nucleobases for the synthesis of novel peptide nucleic acids. J. Chem. Soc., Perkin Trans. 1, 4, 539–546 (Feb., 1997).

Lowe, G. et al, Dipeptides bearing nucleobases for the synthesis of novel peptide nucleic acids. J. Chem. Soc., Perkin Trans. 1, 4, 547–554 (Feb., 1997).

Lowe, G. et al, Solid–phase synthesis of novel peptide nucleic acids. J. Chem. Soc., Perkin Trans. 1, 4, 555–560 (Feb., 1997).

Miller, S. Peptide nucleic acids and prebiotic chemistry. Nature Structural Biology, 4, 167–169 (Mar., 1997).

MÁllegaard, N.E. et al, Peptide nucleic acid•DNA strand displacement loops as artificial transcription promotors. Proc. Natl. Acad. Sci., U.S.A. 91, 3892–3895 (1994).

Nazarenko, I.A. et al, A closed–tube format for amplification and detection of nucleic acids based on energy transfer. Cambridge Healthtech Institute's Fifth Annual Advances in Nucleic Acid Amplification and Detection. San Francisco (Jun., 1997).

Nazarenko, I.a. et al, A closed tube format for amplication and detection of DNA based on energy transfer. Nucleic Acids Res. 25, 12 (Jun., 1997).

Nielsen, P.E. Peptide nucleic acid (PNA): A lead for gene therapeuctic drugs. Perseptives in Drug Discovery and Design 4, 76–84 (1996).

Nielsen, P.E. et al, Evidence for (PNA)2/DNA triplex structure upon binding of PNA to dsDNA by strand displacement. J. Mol. Recog. 7, 165–170 (1994).

Nielsen, P.E. et al, Peptide Nucelic Acid (PNA). A DNA mimic with a peptide backbone. Bioconjugate Chemistry 5, 3–7 (1994).

Nielsen, P.E. et al, Peptide nucelic acids (PNAs): Potential Antisense and Anti–gene Agents. Anti–Cancer Drug Design 8, 53–63 (1993).

Nielsen, P.E. et al, Sequence specific inhibition of DNA restriction enzyme cleavage by PNA. Nucleic Acids Res. 21, 197–200 (1993).

Nielsen, P.E. et al, Sequence–selective recognition of DNA by strand displacement with a thymine–substituted polyamide. Science 254, 1497–1500 (1991).

Nielsen, P.E. et al, Sequence–specific transcription arrest by peptide nucleic acid bound to the DNA template strand. Gene 149, 139–145 (1994).

Nielsen, P.E. et al, Strand displacement binding of duplex–forming homopurine PNA to a homopyrimidine duplex DNA target. J. Am. Chem. Soc. 118, 2287–2288 (1996).

Nielsen, P.E. Peptide Nucleic Acid (PNA). Implications for the origin of the genetic material and the homochirality of life in Physical Origin of Homochirality in Life (D.B. Cline, Ed.) 55–61 (1996).

Nielsen, P.E. Peptide nucleic acids: A new dimension to peptide libraries and aptamers. Methods Enzymol. 267, 426–433 (1996).

Nielsen, P.E., A new target for gene therapeutics: Telomerase. Nature Biotechnology 14, 580 (May, 1996).

Nielsen, P.E., DNA analogues with nonphosphodiester backbones. Annu. Rev. Biophys. Biomol. Struct. 24, 167–183 (1995).

Noble, S.A. et al, Impact of biophysical parameters on the biological assessment of peptide nucleic acids, antisense inhibitors of gene expression. Drug Devel. Res. 34, 184–195 (1995).

Norton, J.C. et al, Inhibition of human telomerase activity by peptide nucleic acids. Nature Biotechnology 14, 615–619 (1996).

Norton, J.C. et al, Targeting Peptide Nucleic Acid–Protein conjugates to structural features within duplex DNA. Bioorg. & Med. Chem. 3, 437–445 (1995).

ørum, H. et al, Sequence specific purification of nucleic acids by PNA controlled hybrid selection. BioTechniques 19, 472–480 (1995).

ørum, H. et al, Single base pair mutation analysis by PNA directed PCR clamping. Nucleic Acids Res. 21, 5332–5336 (1993).

Pardridge, W.M. et al, Vector–mediated delivery of a polyamide (ñpeptideî) nucleic acid analogue through the blood–brain barrier in vivo. Proc. Natl. Acad. Sci., U.S.A. 92, 5592–5596 (1995).

Patel, D.J., Marriage of convenience. Nature 365, 490–492 (1993).

Peffer, N.J. et al, Strand–invasion of duplex DNA by peptide nucleic acid oligomers. Proc. Natl. Acad. Sci., U.S.A. 90, 10648–10652 (1993).

Perry–O'Keefe, H. et al, PNA pre–gel hybridization: an alternative to southern blotting. Proc. Natl. Acad. Sci., U.S.A. 93, 14670–14675 (1996).

PerSeptive Promotional Literature. Peptide Nucleic Acids (PNA): Expanding the role of synthetic DNA analogs. 1995.

PerSeptive Promotional Literature. PNA Oligomers as hybridization probes. 1995.

PerSeptive Promotional Literature. Bio ConSepts: PNA and its use as an analytical molecular biology tool. 1996.

PerSeptive Promotional Literature. PNA: Probing the Improbable. 1997.

Petersen, K. et al, A PNA–DNA linker synthesis of N–((4, 4–Dimethoxytrityloxy)ethyl)–N–(Thymin–1–ylacetyl)glycine. Bioorg. & Med. Chem. Lett. 11, 1119–1124 (1995).

Petersen, K.H. et al, Synthesis and oligomerization of N–Boc–N(thymin–1–ylacetyl)ornithine. Bioorg. & Med. Chem. Lett. 6, 793–796 (1996).

Rasmussen, H. et al, Crystal structure of a peptide nucleic acid (PNA) duplex at 1.7 □ resolution. Nature Structural Biology, 4, 98–101 (Feb., 1997).

Rose, D.J. Characterization of Antisense Binding Properties of Peptide Nucleic Acids by Capillary Gel Electrophoresis. Anal. Chem. 65, 3545–3549 (1993).

Schmidt, J.G. et al., Separation of ñUnchargedî oligodeoxynucleotides analogs by anion–exchange chromatography at high pH. Anal. Biochem. 235, 239–241 (1996).

Seeger, C. et al, PNA–Mediated purification of PCR amplifiable human genomic DNA from whole blood. Biotechniques 23, 512–517 (Sep., 1997).

Shampine, L.J. et al, Electrospray Ionization Mass Spectrometry of ñPeptide Nucleic Acidsî. 42nd ASMS Conference on Mass Spectrometry (May 1994).

Shuber, A.P. et al, High throughput parallel analysis of hundreds of patients samples for more than 10 mutations in multiple disease genes. Human Mol. Genetics 6, 337–347 (Mar., 1997).

Shuber, A.P. et al, Efficient 12–mutation testing in the CFTR gene: a general model for complex mutation analysis. Human Mol. Genetics 2, 152–158 (1993).

Takao, T. et al, Positive–Ion Fast–Atom Bombardment Tandem Mass Spectrometry of Peptide Nucleic Acids. Rapid Cumm. Mass Spec. 8, 925–928 (1994).

Taylor, R.W. et al, Selective inhibition of mutant human mitochrondrial DNA replication in vitro by peptide nucleic acids. Nature Genetics 15, 212–215 (Feb., 1997).

Thiede, C. et al, Simple and sensitive detection of mutations in the ras proto–oncogenes using PNA–mediated PCR clamping. Nucleic Acids Res. 24, 983–984 (1996).

Thisted, M. et al, Detection of Immunoglobulin Kappa Light Chain mRNA in Paraffin Sections by In Situ Hybridization Using Peptide Nucleic Acid Probes. Cell Vision, 3, 5, 358–363 (Sep./Oct. 1996).

Thomson, S.A. et al, Fmoc Mediated Synthesis of Peptide Nucleic Acids, Tetrahedron 51, 6179–6194 (1995).

Tomac, S. et al, Ionic effects on the stability and conformation of Peptide Nucleic Acid Complexes. J. Am. Chem. Soc. 118, 5544–5552 (1996).

Torres, R.A. et al, Interresidue hydrogen bonding in a peptide nucleic acid RNA heteroduplex. Proc. Natl. Acad. Sci. USA, 93, 649–653 (1996).

Tsantrizos, Y. et al, Stereoselective synthesis of a thymine derivative of (S)–2–hydroxy–4–(2–aminophenyl)butanoic acid. A novel building block for the synthesis of aromatic peptide nucleic acid oligomers. J. Org. Chem. 62, 5451–5457 (Aug., 1997).

Tyagi, S. et al, Molecular Beacons: Probes that Fluoresce upon Hybridization. Nature Biotech. 14, 303–308 (1996).

Uhlmann, E. et al, Synthesis of polyamide nucleic acids (PNAs), PNA/DNA–chimerase and phosphonic ester nucleic acids (PHONAs). Nucleosides & Nucleotides, 16(5&6), 603–608 (May/Jun., 1997).

Valdivia, L. et al, Polymeric peptide probes and uses thereof. WO 96/36734 (Nov. 21, 1996).

van der Laan, A.C. et al, A Convenient Automated Solid–Phase Synthesis of PNA–(5')–DNA–(3')–PNA Chimera. Tett Lett, 38, 2249–2252 (Mar., 1997).

Veselkov, A.G. et al, A new class of genome rare cutters. Nucleic Acids Res. 24, 2483–2487 (Jan., 1996).

Veselkov, A.G. et al, PNA as a rare genome–cutter. Nature 379, 214 (Jan., 1996).

Wang, J. et al, Peptide Nucleic Acid Probes for Sequence–Specific DNA Biosensors. J. Am. Chem. Soc. 118, 7667–7670 (1996).

Weller, J. et al, Hybridisation based DNA screening on peptide nucleic acid (PNA) oligomer arrays. Nucl. Acids Res., 25, 14, 2792–2799 (Jul., 1997).

Wittung, P. et al, Direct observation of strand invasion by peptide nucleic acid (PNA) into double–stranded DNA. J. Am. Chem. Soc. 118, 7049–7054 (1996).

Wittung, P. et al, DNA–like double helix formed by peptide nucleic acid. Nature 368, 561–563 (1994).

Wittung, P. et al, Induced Chirality in PNA–PNA Duplexes. J. Am. Chem. Soc. 117, 10167–10173 (1995).

Wittung, P. et al, Interactions of DNA binding ligands with PNA–DNA hybrids. Nucleic Acids Res. 22, 5371–5377 (1994).

Wittung, P. et al, Phospholipid membrane permeability of peptide nucleic acid. FEBS Lett. 365, 27–29 (1995).

Wittung, P. et al, Extended DNA–recognition repertoire of peptide nucleic acid (PNA): PNA–dsDNA triple formed with cytosine–rich homopyrimidine PNA. Biochemistry 36, 7973–7979 (Jul., 1997).

Zimmer, C. Life Takes Backbone. Discover, Dec. 38 (1995).

Castro, A. et al, Single–molecule detection of specific nucleic acid sequences in unamplified genomic DNA. Anal. Chem. 69, 3915–3920 (Oct. 1, 1997).

Demidov, V. et al, Kinetic analysis of specificity of duplex DNA targeting by homopyrimidine peptide nucleic acids. Biophysical Journal 72, 2763–2769 (Jun. 1997).

Good, L. et al, Progress in developing PNA as a gene–targeting dug. Antisense & Nucleic Acid Drug Develop. 7, 431–437 (Aug. 1997).

Hamilton, S.E., Identification of determinants for inhibitor binding within the RNA active site of human telomer using PNA scanning. Biochem. 36, 11873–11880 (Sep. 30, 1997).

Ross, P.L. et al, Discrimination of single–nucleotide polymorphisms in human DNA using peptide nucleic acid probes detected by MALDI–TOF mass spectrometry. Anal. Chem. 69, 4197–4202 (Oct. 15, 1997).

Tyagi, S. et al, Detection probes, kits and assays. WO97/39008 (Oct. 23, 1997).

Wittung, P. et al, Observation of a PNA–PNA–PNA triplex. J. Am. Chem. Soc. 119, 3189–3190 (Apr. 2, 1997).

Wittung, P. et al, Recognition of double–stranded DNA by peptide nucleic acid. Nucleosides & Nucleotides 16, 599–602 (May/Jun. 1997).

Puskas, L.G. et al. Reduction of mispriming in amplification reactions with restricted PCR. Genome Res. 3, 309–311 (1995).

Corey, D.R. Peptide nucleic acids: expanding the scope of nucleic acid recognition. TIBTECH 15, 224 229 (1997).

Smulevitch, S.V. et al, Enhancement of strand invasion by oligonucleotides through manipulation of backbone charge. Nature Biotech. 14, 1700–1704 (1996).

Bentin, T. et al, Enhanced Peptide Nucleic Acid Binding to Supercoiled DNA: Possbile Implications for DNA "Breathing" Dynamics. Biochemistry 35, 8863–8869 (1996).

Corey, D.R. 48000–fold Acceleration of Hybridization by Chemically Modified Oligonucleotides. J.Am. Chem. Soc. 117, 9373–9374 (1995).

Jensen, K.K. et al, Kinetics for Hybridization of Peptide Nucleic Acids (PNA) with DNA and RNA Studied with the BIAcore Technique. Biochemistry 36, 5072–5077 (1997).

Leijon, M. et al, Unique Base–pair Breathing Dynamics in PNA–DNA Hybrids. J. Mol. Biol. 271, 438–455 (1997).

Lesnik, E.A. et al. Evaluation of pyrimidine PNA binding to ssDNA targets from nonequilibrium melting experiments. Nucleic Acids Research 25, 568–574 (1997).

Norton, J.C. et al, Targeting Peptide Nucleic Acid–Protein Conjugates to Structural Features Within Duplex DNA. Bioogranic & Medicinal Chemistry 3, 437–445 (1995).

Torres, R.A. et al, Interresidue hydrogen bonding in a peptide nucleic acid RNA heteroduplex. Proc. Natl. Acad. Sci. 93, 649–653 (1996).

Wetmur, J.G., DNA Probes: Applications of the Principals of Nucleic Acid Hybridization. Critical Reviews in Biochemistry and Molecular Biology 26, 227–259 (1991).

Molecular Diagram

Figure 4A

|  | Labeled Wild Type Probes | | | | | | Labeled Mutant Probes | | | | | |
|---|---|---|---|---|---|---|---|---|---|---|---|---|
| Blocker Probe (X) | 0.0 | 0.5 | 1.0 | 2.0 | 4.0 | 8.0 | 0.0 | 0.5 | 1.0 | 2.0 | 4.0 | 8.0 |
| Match Target | A1 | A2 | A3 | A4 | A5 | A6 | A7 | A8 | A9 | A10 | A11 | A12 |
|  | B1 | B2 | B3 | B4 | B5 | B6 | B7 | B8 | B9 | B10 | B11 | B12 |
|  | C1 | C2 | C3 | C4 | C5 | C6 | C7 | C8 | C9 | C10 | C11 | C12 |
| Mismatch Target | D1 | D2 | D3 | D4 | D5 | D6 | D7 | D8 | D9 | D10 | D11 | D12 |
|  | E1 | E2 | E3 | E4 | E5 | E6 | E7 | E8 | E9 | E10 | E11 | E12 |
|  | F1 | F2 | F3 | F4 | F5 | F6 | F7 | F8 | F9 | F10 | F11 | F12 |
| No Target | G1 | G2 | G3 | G4 | G5 | G6 | G7 | G8 | G9 | G10 | G11 | G12 |
|  | H1 | H2 | H3 | H4 | H5 | H6 | H7 | H8 | H9 | H10 | H11 | H12 |

Figure 4D

Match to Mismatch Ratio

| # | A | B | C | D | E | F | G |
|---|---|---|---|---|---|---|---|
| 1 | Blocker Probe(X) | \multicolumn{6}{c}{LABELED PROBES} | | | | | |
| 2 | | Wild Type DNA 25-mer | Mutant DNA 25-mer | Wild Type PNA | Mutant PNA | Wild Type DNA15-mer | Mutant DNA 15-mer |
| 3 | No Blocker | 9 | 12 | 6 | 5 | 6 | 5 |
| 4 | 0.5X | 27 | 73 | 497 | 255 | 46 | 83 |
| 5 | 1X | 34 | 125 | 1211 | 407 | 68 | 134 |
| 6 | 2X | 110 | 173 | 1009 | 929 | 105 | 185 |
| 7 | 4X | 222 | 320 | 1084 | 1192 | 129 | 211 |
| 8 | 8X | 279 | 278 | 1557 | 1186 | 169 | 278 |

Figure 5A

| | Match Target | | | | | | No Target | | Mismatch Target | | | |
|---|---|---|---|---|---|---|---|---|---|---|---|---|
| Target (fmole) | 50 | | 5 | | 0.5 | | 0 | | 500 | | 50 | |
| Blocker Probe | - | + | - | + | - | + | - | + | - | + | - | + |
| Labeled Wild Type Probe | A1 | A2 | A3 | A4 | A5 | A6 | A7 | A8 | A9 | A10 | A11 | A12 |
| | B1 | B2 | B3 | B4 | B5 | B6 | B7 | B8 | B9 | B10 | B11 | B12 |
| | C1 | C2 | C3 | C4 | C5 | C6 | C7 | C8 | C9 | C10 | C11 | C12 |
| | D1 | D2 | D3 | D4 | D5 | D6 | D7 | D8 | D9 | D10 | D11 | D12 |
| Labeled Mutant Probe | E1 | E2 | E3 | E4 | E5 | E6 | E7 | E8 | E9 | E10 | E11 | E12 |
| | F1 | F2 | F3 | F4 | F5 | F6 | F7 | F8 | F9 | F10 | F11 | F12 |
| | G1 | G2 | G3 | G4 | G5 | G6 | G7 | G8 | G9 | G10 | G11 | G12 |
| | H1 | H2 | H3 | H4 | H5 | H6 | H7 | H8 | H9 | H10 | H11 | H12 |

Figure 5B

Match to Mismatch Ratio

(50 fmole)

| # | A | B | C |
|---|---|---|---|
| 1 | Labeled Probe | No Blocker | 2X Blocker |
| 2 | Wild Type PNA | 2.5 | 78 |
| 3 | Mutant PNA | 4.1 | 140 |
| 4 | Wild Type DNA-25 | 2.5 | 30 |
| 5 | Mutant DNA-25 | 2.3 | 42 |
| 6 | Wild Type DNA-15 | 1.1 | 30 |
| 7 | Mutant DNA-15 | 1.1 | 65 |

Figure 5D

Blocker Effect

| # | A | B | C | D | E | F |
|---|---|---|---|---|---|---|
|   |   | 50 fmole | 5 fmole | 0.5 fmole | 500 fmole | 50 fmole |
| 1 | Labeled Probe | Match | Match | Match | Mismatch | Mismatch |
| 2 | Wild Type PNA | 1.5 | 1.0 | 0.8 | 132 | 46 |
| 3 | Mutant PNA | 1.2 | 0.9 | 1.3 | 86 | 40 |
| 4 | Wild Type DNA 25-mer | 0.8 | 1.4 | 1.0 | 11 | 10 |
| 5 | Mutant DNA 25-mer | 1.0 | 1.1 | 1.4 | 16 | 18 |
| 6 | Wild Type DNA 15-mer | 0.9 | 0.8 | 1.1 | 17 | 24 |
| 7 | Mutant DNA 15-mer | 0.5 | 0.6 | 1.1 | 23 | 31 |

Figure 6A

| Labeled Probe | Blocker Probe | TIMING | Mutant Target | | No Target | Wild Type Target |
|---|---|---|---|---|---|---|
| | | | 500 fmole | 50 fmole | | 50 fmole |
| Wild Type DNA 25-mer | Mutant DNA 25-mer | Normal (60 min.) | A1 A2 A3 | A4 A5 A6 | A7 A8 A9 | A10 A11 A12 |
| | Mutant PNA | | B1 B2 B3 | B4 B5 B6 | B7 B8 B9 | B10 B11 B12 |
| | No Blocker | | C1 C2 C3 | C4 C5 C6 | C7 C8 C9 | C10 C11 C12 |
| | Mutant DNA 25-mer | FAST (20 min.) | D1 D2 D3 | D4 D5 D6 | D7 D8 D9 | D10 D11 D12 |
| | Mutant PNA | | E1 E2 E3 | E4 E5 E6 | E7 E8 E9 | E10 E11 E12 |
| | No Blocker | | F1 F2 F3 | F4 F5 F6 | F7 F8 F9 | F10 F11 F12 |
| Wild Type PNA | Mutant PNA | | G1 G2 G3 | G4 G5 G6 | G7 G8 G9 | G10 G11 G12 |
| | No Blocker | | H1 H2 H3 | H4 H5 H6 | H7 H8 H9 | H10 H11 H12 |

Table 6B

Match to Mismatch Ratio

| # | A | B | C | D |
|---|---|---|---|---|
| 1 | LabeledProbe | Blocker Probe | Timing | 50 fmole |
| 2 | DNA 25-mer | DNA | 60 min. | 125 |
| 3 | | PNA | | 76 |
| 4 | | NB | | 16 |
| 5 | | DNA | 20 min. | 72 |
| 6 | | PNA | | 101 |
| 7 | | NB | | 10 |
| 8 | PNA | PNA | | 357 |
| 9 | | NB | | 2 |

NB = No Blocker

Table 6C

Blocker Effect

| # | A | B | C | D | E | F |
|---|---|---|---|---|---|---|
|   |   |   |   | 50 fmole | 500 fmole | 50 fmole |
| 1 | Labeled Probe | Blocker probe | Timing | Match | Mismatch | Mismatch |
| 2 | DNA-25 | DNA | 60 min. | 0.9 | 7 | 7 |
| 3 |   | PNA |   | 1.6 | 20 | 8 |
| 4 |   | DNA | 20 min. | 0.7 | 5 | 5 |
| 5 |   | PNA |   | 1.2 | 13 | 13 |
| 6 | PNA | PNA |   | 1.6 | 175 | 328 |

```
3'  765                                        725  '5
    |                                           |
...CUGUACUUGCAGUCACAAUAGGGUCCUCCGACGGAAGCGGT...    N. gonorrhoeae rRNA target ...CUGUACUUGCAGUCACAACAGGGUCCUCCGACGGAAGCGGT...    N. meningitidis rRNA target CAGTGTTATCCCAGG                            N.g. - PNA capture probe OL6
                       \
                (O-link)2-K-Arylamine CAGTGTTATCCCAGG                            N.g. - PNA blocker probe CAGTGTTGTCCCAGG                            N.m. - PNA blocker probe
       '5              3'
```

Figure 7

|  | No blocker | | N.g. Blocker | | N.m. Blocker | | |
|---|---|---|---|---|---|---|---|
|  | N.g. | N.m. | N.g. | N.m. | N.g. | N.m. | |
| 170 fmole | | | | | | | A |
| 54 fmole | | | | | | | B |
| 17 fmole | | | | | | | C |
| 5.4 fmole | | | | | | | D |
| 1.7 fmole | | | | | | | E |
| 0.54 fmole | | | | | | | F |
| 0.17 fmole | | | | | | | G |
| 0 fmole | | | | | | | H |
| | 1  2 | 3  4 | 5  6 | 7  8 | 9  10 | 11  12 | |

| | A | B | C | D | E | F | G |
|---|---|---|---|---|---|---|---|
| Target Level | No PNA Blocker | | PNA Blocker to N.m. | | PNA Blocker to N.g. | | Blocker |
| (fmole) | N.g. | N.m. | N.g. | N.m. | N.g. | N.m. | Target level |
| 170 | 0.775 | 0.037 | 0.478 | 0.012 | 0.101 | 0.031 | 10 |
| 54 | 0.232 | 0.019 | 0.168 | 0.005 | 0.033 | 0.021 | 31.6 |
| 17 | 0.096 | 0.012 | 0.070 | 0.004 | 0.013 | 0.012 | 100 |
| 5.4 | 0.034 | 0.007* | 0.032 | 0.002* | 0.009 | 0.008 | 316 |
| 1.7 | 0.016 | 0.004 | 0.012 | 0.003 | 0.009 | 0.005 | 1000 |
| 0.54 | 0.007 | 0.002 | 0.007 | 0.003* | 0.005 | 0.003 | 3160 |
| 0.17 | 0.002 | 0.002 | 0.001 | 0.002 | 0.003 | 0.003 | 10000 |

*One of 2 data points was clearly erroneous and omitted. All other values are average of 2 data points.

Figure 8C

| | A | B | C | D |
|---|---|---|---|---|
| Target | PNA Blocker to N.m. | | PNA Blocker to N.g. | |
| (fmole) | N.g. | N.m. | N.g. | N.m. |
| 170 | 38.3 | 67.6 | 87.0 | 16.2 |
| 54 | 27.6 | 73.7 | 85.8 | -10.5 |
| 17 | 27.1 | 66.7 | 86.5 | 0.0 |
| 5.4 | 5.9 | 71.4 | 73.5 | -14.3 |
| 1.7 | 25.0 | 25.0 | 43.8 | -25.0 |
| 0.54 | 0.0 | -50.0 | 28.6 | -50.0 |
| 0.17 | 50.0 | 0.0 | -50.0 | -50.0 |

| Target Level (fmole) | A<br>No blocker | B<br>N.m. blocker | C<br>N.g. blocker |
|---|---|---|---|
| 170 | 20.9 | 39.8 | 3.3 |
| 54 | 12.2 | 33.6 | 1.6 |
| 17 | 8.0 | 17.5 | 1.1 |
| 5.4 | 4.9 | 16.0 | 1.1 |
| 1.7 | 4.0 | 4.0 | 1.8 |
| 0.54 | 3.5 | 2.3 | 1.7 |
| 0.17 | 1.0 | 0.5 | 1.0 |

METHODS, KITS AND COMPOSITIONS FOR SUPPRESSING THE BINDING OF DETECTABLE PROBES TO NON-TARGET SEQUENCES IN HYBRIDIZATION ASSAYS

CROSS REFERENCE TO RELATED APPLICATIONS

This application is a continuation of U.S. Ser. No. 08/963,472 filed on Nov. 3, 1997, now U.S. Pat. No 6,110,676, which is a continuation-in-part of U.S. Ser. No. 08/927,709, filed on Sep. 25, 1997, now abandoned, which claims priority to U.S. Provisional Application No. 60/032,349, filed on Dec. 4, 1996, now abandoned.

BACKGROUND OF THE INVENTION

1. Field of the Invention

This invention is related to the field of probe based nucleic acid sequence detection, quantitation and analysis. More specifically, this invention relates to methods, kits and compositions suitable for suppressing the binding of detectable nucleic acid probes or detectable PNA probes to non-target sequences in an assay for detecting a target sequence of a nucleic acid molecule of interest.

2. Description of the Related Art

Probe based assays are useful in the detection, quantitation and analysis of nucleic acids. Nucleic acid probes have long been used to analyze samples for the presence of nucleic acid from a bacteria, fungi, virus or other organism (See for example: U.S. Pat. Nos. 4,851,330, 5,288,611, 5,567,587, 5,601,984 and 5,612,183). Probe-based assays are also useful in examining genetically-based clinical conditions of interest. Nonetheless, probe-based assays have been slow to achieve commercial success. This lack of commercial success is, at least partially, the result of difficulties associated with specificity, sensitivity and reliability.

Nucleic acid hybridization is a fundamental process in molecular biology. Sequence differences as subtle as a single base (point mutation) in very short oligomers (<10 base pairs "bp") can be sufficient to enable the discrimination of the hybridization to complementary nucleic acid target sequences as compared with non-target sequences. Nonetheless, nucleic acid probes of greater than 10 bp in length are generally required to obtain the sequence diversity necessary to correctly identify a unique organism or clinical condition of interest. However, the ability to discriminate between closely related sequences is inversely proportional to the length of the hybridization probe because the difference in thermal stability decreases between wild type and mutant complexes as the probe length increases. Consequently, the power of probe based hybridization to correctly identify the target sequence of interest from closely related (e.g. point mutations) non-target sequences can be very limited.

A extensive review of the "Principles and Practices of Nucleic Acid Hybridization" is available (See: David E Kennell, Principles and Practices of Nucleic Acid Hybridization, pp. 259–301). In the manuscript, the author discusses the "Use of Competitor RNA to Estimate Specificity". This process is based on the principle that two identical molecules will compete with each other for a common binding site. This principle is applied to assess similarities between two RNA populations competing for a common DNA. Typically, one population of RNA is labeled and the competitor population of RNA is unlabeled. The competition assay is used to estimate the degree of relation between the two RNA species. A process called "presaturation competition", wherein the unlabeled competitor RNA is hybridized to the DNA before hybridization of the labeled RNA, has been reported to be useful in improving the results of this type of assay (See: p 297). However, the author warns that "great caution should be exercised" in interpreting the data from these assays (See: p. 291 and p. 298 first full paragraph). No data is provided which quantitates the benefits associated with the application of this methodology.

Gray et al. describe in-situ methods for chromosome-specific staining wherein the hybridization of labeled nucleic acid fragments to repetitive sequences of chromosomal DNA is disabled (See: Gray et al. U.S. Pat. No. 5,447,841). In one embodiment of the invention, disabling of the hybridization capacity of the repetitive DNA sequences within nucleic acid fragments involves blocking the repetitive sequences by pre-reassociation of fragments with fragments of repetitive-sequence-rich DNA, by pre-reassociation of target DNA with fragments of repetitive-sequence-rich DNA, or pre-reassociation of both the fragments of the heterogeneous mixture and the target DNA with repetitive-sequence-rich DNA (See: col. 9, lns. 58–68). The pre-reassociation procedure may be performed in a number of differing formats (See: claims 2–5). This method provides blocking sufficient to permit detection of large labeled nucleic acid (greater than 1000 bp) hybridized to chromosomal DNA (See: Claim 1). No data is provided which quantitates the benefits associated with the application of this methodology. Moreover, this treatment merely results in nucleic acid fragments whose repetitive sequences are blocked by complementary fragments such that sufficient unique sequence regions remain free for attachment to chromosomal DNA during the in-situ hybridization step (See: col. 10, lns. 3–13).

Hybridization assays hold promise as a means to screen large numbers of patient samples for a large number of mutations. In practice, however, it is often difficult to multiplex an assay given the requirement that each of the many very different probes in the assay must exhibit a very high degree of specificity for a specific target nucleic acid under the same or similar conditions of stringency. Recently however, a probe based assay has been shown to be effective at selectively detecting up to twelve cystic fibrosis transmembrane conductance regulator (CFTR) mutations using pools of allele specific oligonucleotides "ASOs" (See: Shuber et al., Human Mol. Gen., (1993) 2, 153–158). The authors utilized a tetramethylammonium chloride (TMAC) buffer to eliminate variability in the affinity of the nucleic acid probes for their complementary target nucleic acid sequences. Interestingly, the authors describe the use of labeled and unlabeled nucleic acid probes in the hybridization cocktail. However, there is no discussion of the rational for applying this methodology and there is no data provided which quantitates the benefits associated with application of this technology.

More recently, Shuber and his coworkers introduced a technique they coined MASDA (multiplex allele specific diagnostic assay). See: Shuber et al. Human Mol. Gen. (1997) 6, 337–347. In this assay, a single hybridization is performed with a pool of allele specific oligonucleotide probes. The ASOs are affinity purified from the pool by hybridization to the target nucleic acid (patient sample) which has been immobilized to a surface. Probes, which hybridize to the target nucleic acid, are thereafter eluted from the surface and analyzed to thereby determine the presence or absence of one or more clinical conditions of interest. The authors report that they observe such a high degree of specificity of hybridization of the component labeled ASOs of the pool that, in a single assay, the method is capable of analyzing greater than 500 samples for greater than 100 known mutations. As in the prior Shuber publication, the authors describe the use of a hybridization cocktail containing both labeled and unlabeled probes. This cocktail is prepared to achieve uniform hybridization signals in the assay. However, no data is provided which quantitates the benefits associated with the application of this methodology.

The background art thus far discussed does not disclose, suggest or teach anything about Peptide Nucleic Acids (PNAs).

Peptide Nucleic Acids (PNAs) are non-naturally occurring polyamides which can hybridize to nucleic acids (DNA and RNA) with sequence specificity. (See U.S. Pat. No. 5,539,082 and Egholm et al., Nature (1993) 365, 566–568). PNA's are candidates for investigation as alternatives/substitutes to nucleic acid probes in probe-based hybridization assays because they exhibit several desirable properties. PNA's are achiral polymers which hybridize to nucleic acids to form hybrids which are more thermodynamically stable than a corresponding nucleic acid/nucleic acid complex (See: Egholm et. al., Nature (1993) 365, 566–568). Being non-naturally occurring molecules, they are not known to be substrates for the enzymes which are known to degrade peptides or nucleic acids. Therefore, PNA's should be stable in biological samples, as well as, have a long shelf-life. Unlike nucleic acid hybridization which is very dependent on ionic strength, the hybridization of a PNA with a nucleic acid is fairly independent of ionic strength and is favored at low ionic strength under conditions which strongly disfavor the hybridization of nucleic acid to nucleic acid (See: Egholm et. al., Nature, p. 567). The effect of ionic strength on the stability and conformation of PNA complexes has been extensively investigated (See: Tomac et al. J. Am. Chem. Soc. (1996) 118, 5544–5552). Sequence discrimination is more efficient for PNA recognizing DNA than for DNA recognizing DNA (See: Egholm et al., Nature, p. 566). However, the advantages in point mutation discrimination with PNA probes, as compared with DNA probes, in a hybridization assay appears to be somewhat sequence dependent (See: Nielsen et al. Anti-Cancer Drug Design (1993) 8, 53–65). As an additional advantage, PNA's hybridize to nucleic acid in both a parallel and antiparallel orientation, though the antiparallel orientation is preferred (See: Egholm et al., Nature, p. 566).

PNAs are synthesized by adaptation of standard peptide synthesis procedures in a format which is now commercially available. (For a general review of the preparation of PNA monomers and oligomers please see: Dueholm et al., New J. Chem. (1997), 21, 19–31 or Hyrup et. al., Bioorganic & Med. Chem. (1996) 4, 5–23). Labeled and unlabeled PNA oligomers can be purchased (See: PerSeptive Biosystems Promotional Literature: BioConcepts, Publication No. NL612, Practical PNA, Review and Practical PNA, Vol. 1, Iss. 2) or prepared using the commercially available products.

Labeled PNA probes have been hybridized to target nucleic acid subsequences of denatured dsDNA as a means to detect the presence and amount of the DNA of interest in an assay coined "pre-gel hybridization" (See: O'Keefe et al. Proc. Natl. Acad. Sci. USA (1996) 93, 14670–14675). This assay relies on the rapid kinetics of PNA/DNA hybrid formation and the relatively slow rate of reannealing of the dsDNA. Thus, under conditions of low salt, the sample is analyzed for the presence of the PNA/DNA hybrid before the PNA/nucleic acid complex is dissociated by the reannealing/reformation of the dsDNA. "Pre-gel hybridization" is reported to provide very good discrimination of point mutations in a DNA sample (See: FIG. 4 of the O'Keefe manuscript and the associated description).

In a similar manner, unlabeled PNAs have been shown to be effective at blocking the interstrand and intrastrand interactions of dsDNA to thereby enhance the PCR amplification of variable numbers of tandem repeat (VNTR) loci (See: Demers et al. Nucl. Acids Res., (1995) 23, 3050–3055 and U.S. Pat. No. 5,656,461). For this application, the unlabeled PNAs need to be designed such that they form PNA/nucleic acid hybrids which are stable enough to disrupt the interstrand and intrastrand interactions of dsDNA. However, the PNA/nucleic acid complex must be susceptible to dissociation by the operation of the polymerase during primer extension.

In still another related application, a process coined "PCR clamping" can be used to obtain point mutation discrimination when directing unlabeled PNAs of defined sequence to interfere with the PCR process (See: Ørum et al. Nucl. Acids Res. (1993), 21, 5332–5336). In one embodiment of PCR clamping, an unlabeled PNA, which is identical in nucleobase composition to the PCR primer, competes with the PCR primer for binding to the common recognition site. In another embodiment, the target site for the unlabeled PNA is located within the PCR amplicon region. In this embodiment, clamping operates if the PNA/nucleic acid hybrid is stable enough to prevent read through by the polymerase. In yet another embodiment, the target site for the unlabeled PNA is located adjacent to the PCR priming site. In this embodiment, PCR clamping may operate either by preventing read through of the polymerase or by preventing (blocking) primer annealing. To obtain point mutation discrimination using PCR clamping, longer mutant and wild type nucleic acid PCR primers are designed such that amplification proceeds only if the longer PCR primer is a perfect complement to the recognition site and thereby out competes the unlabeled PNA for binding within that site. PCR clamping has recently been directed to analysis of the Ki-ras mutations of codon 12 and 13 (See: Thiede et al. Nucl. Acids Res. (1996) 24, 983–984).

Very recently, the "Hybridization based screening on peptide nucleic acid (PNA) oligomer arrays" has been described wherein arrays of some 1000 PNA oligomers of individual sequence were synthesized on polymer membranes (See: Weller et al. Nucl. Acids Res. (1997) 25, 2792–2799). Arrays are generally used, in a single assay, to generate affinity binding (hybridization) information about a specific sequence or sample to numerous probes of defined composition. Thus, PNA arrays may be useful in diagnostic or antisence applications. However, in the present study, the authors note that the affinity and specificity of DNA hybridization to immobilized PNA oligomers depended on hybridization conditions more than was expected. Moreover, there was a tendency toward non-specific binding at lower ionic strength. Furthermore, certain very strong binding mismatches were identified which could not be eliminated by more stringent washing conditions. These results demonstrate the need for improved methods of suppressing the binding of nucleic acids to non-complementary PNAs. Moreover, these unexplained results are also illustrative of the lack of complete understanding of these newly discovered molecules (i.e. PNA)

There are indeed many differences between PNA probes and standard nucleic acid probes. These differences can be conveniently broken down into biological, structural, and physico-chemical differences. As discussed above and below, these biological, structural, and physico-chemical differences may lead to unpredictable results when attempting to use PNA probes in applications were nucleic acids have typically been employed. This non-equivalency of differing compositions is often observed in the chemical arts.

With regard to biological differences, nucleic acids, are biological materials that play a central role in the life of living species as agents of genetic transmission and expression. Their in vivo properties are fairly well understood. PNA, on the other hand is recently developed totally artificial molecule, conceived in the minds of chemists and made using synthetic organic chemistry. It has no known biological function.

Structurally, PNA also differs dramatically from nucleic acid. Although both can employ common nucleobases (A, C, G, T, and U), the backbones of these molecules are structurally diverse. The backbones of RNA and DNA are composed of repeating phosphodiester ribose and 2-deoxyribose units. In contrast, the backbones of PNA are composed on N-(2-aminoethyl)glycine units. Additionally, in PNA the nucleobases are connected to the backbone by an additional methylene carbonyl unit.

Despite its name, PNA is not an acid and contains no charged acidic groups such as those present in DNA and RNA. Because they lack formal charge, PNAs are generally more hydrophobic than their equivalent nucleic acid molecules. The hydrophobic character of PNA allows for the possibility of non-specific (hydrophobic/hydrophobic interactions) interactions not observed with nucleic acids. Further, PNA is achiral, providing it with the capability of adopting structural conformations the equivalent of which do not exist in the RNA/DNA realm.

The physico/chemical differences between PNA and DNA or RNA are also substantial. PNA binds to its complementary nucleic acid more rapidly than nucleic acid probes bind to the same target sequence. This behavior is believed to be, at least partially, due to the fact that PNA lacks charge on its backbone. Additionally, recent publications demonstrate that the incorporation of positively charged groups into PNAs will improve the kinetics of hybridization (See: Iyer et al. J. Biol. Chem. (1995) 270, 14712–14717). Because it lacks charge on the backbone, the stability of the PNA/nucleic acid complex is higher than that of an analogous DNA/DNA or RNA/DNA complex. In certain situations, PNA will form highly stable triple helical complexes or form small loops through a process called "strand displacement". No equivalent strand displacement processes or structures are known in the DNA/RNA world.

In summary, because PNAs hybridize to nucleic acids with sequence specificity, PNAs are useful candidates for developing probe-based assays. However, PNA probes are not the equivalent of nucleic acid probes. Nonetheless, even under the most stringent conditions both the exact target sequence and a closely related sequence (e.g. a non-target sequence having a single point mutation (a.k.a. single base pair mismatch)) will often exhibit detectable interaction with a labeled nucleic acid or labeled PNA probe (See: Nielsen et al. Anti-Cancer Drug Design at p. 56–57 and Weilep et al. at p. 2798, second full paragraph). Any hybridization to a closely related non-target sequence will result in the generation of undesired background signal. Because the sequences are so closely related, point mutations are the some of the most difficult of all nucleic acid modifications to detect using a probe based assay. Numerous diseases, such as sickle cell anemia and cystic fibrosis, are caused by a single point mutation of genomic nucleic acid. Consequently, any method, kits or compositions which could improve the specificity, sensitivity and reliability of probe-based assays would be useful in the detection, analysis and quantitation of nucleic acid containing samples and particularly useful for nucleic acid point mutation analysis.

OBJECTS OF THE INVENTION

It is an object of the invention to provide methods, kits and compositions suitable for the suppression of the binding of probes to non-target sequences in hybridization assays.

It is an object of this invention to provide methods, kits and compositions suitable for improving the specificity sensitivity and reliability of nucleic acid point mutation detection, analysis and quantitation.

SUMMARY OF THE INVENTION

This invention relates to methods, kits and compositions suitable for the improved detection, quantitation and analysis of nucleic acid target sequences using probe-based hybridization assays. The invention is more specifically directed to methods, kits and compositions suitable for suppressing the binding of detectable probes to non-target sequences in an assay for a target sequence of a nucleic acid target molecule. Suppression of the nonspecific binding of detectable probe directly improves the sensitivity of the assay thereby improving the signal to noise ratio of the assay. Suppression of nonspecific binding will also result in improvements in reliability since the incidence of false positives and false negative should also be reduced. Because the methods, kits and compositions of this invention are directed to the suppression of nonspecific binding of probes to nucleic acids, they are particularly well suited for the development of sensitive and reliable probe-based hybridization assays designed to analyze for point mutations. The methods, kits and compositions of this invention should also find utility for the detection, quantitation or analysis of organisms (micro-organisms), viruses, fungi and genetically based clinical conditions of interest.

It has been surprisingly observed that the signal caused by the nonspecific binding of detectable probes to one or more non-target nucleic acid sequences can be dramatically suppressed by the addition of one or more unlabeled probes wherein the sequence of the one or more unlabeled probes is complementary to one or more non-target sequences to which the detectable probe binds in a nonspecific manner. For example, it has been observed that the addition of 25 equivalents of unlabeled PNA probe, having a single mismatch as compared with the labeled PNA probe, does not substantially alter the detection limit of the assay. However, the presence of the unlabeled PNA probe resulted in at least a 10 fold suppression in the binding of labeled PNA probe to the non-target sequence (point mutation) and a correlating improvement of approximately 30 fold, in the signal to noise ratio of the assay (see Example 4A and FIG. 1).

When the unlabeled PNA probe was present at 500 equivalents, there was very little loss of detectable signal (approximately 3 to 10 fold). However, suppression of binding of the labeled probe to a non-target sequence (point mutation) is substantially improved as compared with the experiment wherein only 25 equivalents of unlabeled PNA probe was present (Compare: Examples 4A and 4B of this specification). The results demonstrate that point mutation discrimination improved from approximately 10 fold in the absence of the unlabeled probe to greater than 1000 fold in the presence of high levels of unlabeled (blocker) PNA probe. Consequently, when employing the methods described herein, one can achieve several logs of improvement in point mutation discrimination and similar dramatic improvements in the dynamic range of the hybridization assay.

The applicants are not aware of any similar method suitable for obtaining such a dramatic suppression of binding to non-target sequences and the correlating improvement in signal to noise ratio. The data presented in Example 6, demonstrates the clear superiority of PNA probes as compared with DNA probes with regard to suppression of binding to non-target sequences, improvement in signal to noise ratios and point mutation discrimination.

In preferred embodiments of this invention, PNA probes are used either alone or in combination with nucleic acid probes. When combined with nucleic acid probes, the preferred combination involves unlabeled PNA probes used to suppress the binding of detectable (labeled) nucleic acid probes to non-target sequences. In the most preferred embodiment of this invention, both the detectable probes and unlabeled or independently detectable probes are PNA probes because this embodiment exhibits both the greatest ability to suppress binding to non-target sequences and the greatest ability to discriminate point mutations.

The hybridization assay of this invention can be performed in solution. Alternatively, one or more assay components may be immobilized to a surface. Thus, in one embodiment the nucleic acid target molecule comprising the target sequence is immobilized to a surface. In this embodiment, the immobilized target sequence is contacted with a solution containing the detectable and unlabeled or independently detectable probes (e.g. dot blot format). Alternatively, one or more probes may be immobilized on a. surface and used, in a capture assay, to capture the nucleic acid target molecule comprising the target sequence. In a preferred embodiment, arrays of greater than two probes are used to generate binding (affinity) or sequence information about one or more nucleic acid target molecules of interest which may be present in the sample.

In one embodiment, the invention is related to a method for suppressing the binding of detectable probe to a non-target sequence in an assay of a sample for a target sequence. The method comprises contacting the sample with a set containing two or more probes under conditions suitable for the probes to hybridize to nucleic acid. At least one of the probes is a detectable probe labeled with a detectable moiety and having a sequence complementary or substantially complementary to a target sequence. At least one of the other probes is an unlabeled or independently detectable probe having a sequence complementary or substantially complementary to a non-target sequence. The second step comprises detecting the presence, absence or quantity of a target sequence in the sample by directly or indirectly detecting or quantitating the detectable moiety. At least one of either a detectable probe or an unlabeled or independently detectable probe is a PNA probe. Preferably, the one or more unlabeled or independently detectable probes is a PNA probe. Most preferably, all the probes are PNA probes. In preferred embodiments, the detectable probe is perfectly complementary to a target sequence and the unlabeled or independently detectable probe is perfectly complementary to a non-target sequence which may be present in the sample.

In another embodiment, the invention relates to a kit suitable for suppressing the binding of a detectable probe to a non-target sequence in an assay of a sample for a target sequence. The kit comprises a set of two or more probes wherein, at least one of the probes is a detectable probe labeled with a detectable moiety and having a sequence complementary or substantially complementary to the target sequence. At least one of the other probes is an unlabeled or independently detectable probe having a sequence complementary or substantially complementary to the non-target sequence. At least one of either a detectable probe or an unlabeled or independently detectable probe is a PNA probe. Preferably, the one or more unlabeled or independently detectable probes is a PNA probe. Most preferably, all the probes are PNA probes. In preferred embodiments, the detectable probe is perfectly complementary to a target sequence and the unlabeled or independently detectable probe is perfectly complementary to a non-target sequence which may be present in the sample.

In another embodiment, the invention relates to a composition for suppressing the binding of a detectable probe to a non-target sequence in an assay of a sample for a target sequence. The composition consists of a set of two probes wherein, one of the probes is a detectable probe labeled with a detectable moiety and having a sequence complementary to the target sequence. The other probe is an unlabeled or independently detectable probe having a sequence complementary to a non-target sequence. Either of the detectable probe or the unlabeled or independently detectable probe is a PNA probe. Preferably, the unlabeled or independently detectable probe is the PNA probe. Most preferably, both probes of the composition are PNA probes.

In another embodiment, the invention relates to a composition for suppressing the binding of a detectable probe to a non-target sequence in an assay of a sample for a target sequence. The composition consists of a set of four probes wherein, one of the probes is a detectable probe labeled with a detectable moiety and having a sequence complementary to the target sequence. The other three probes are unlabeled or independently detectable probes having sequences which hybridize specifically with non-target sequences which are related to the target sequence as the three possible single point mutations. Either of the detectable probe or at least one of the three unlabeled or independently detectable probes is a PNA probe. Preferably the three unlabeled or independently detectable probes are PNA probes. Most preferably, all probes of the composition are PNA probes.

In yet another embodiment, this invention relates to a method for suppressing the binding of a non-target sequence to a capture probe immobilized on a surface in a capture assay of a sample for a target sequence. The method comprises contacting the sample with a solution containing one or more blocking probes under conditions suitable for the blocking probes to hybridize to nucleic acid. Each of the blocking probes is complementary or substantially complementary to one or more non-target sequences which may be present in the sample. The sample is also contacted with at least one capture probe immobilized on a surface under conditions suitable for the target sequence, if present, to hybridize to the capture probe. The immobilized capture probe is complementary or substantially complementary to the target sequence and thereby forms a capture probe/target sequence complex. The presence or amount of nucleic acid target molecule immobilized to the surface is then detected, identified or quantitated. In preferred embodiments, an array of two or more capture probes immobilized on a surface is used to screen one or more samples for one or more target sequences of interest. In preferred embodiments, the blocking probe is perfectly complementary to a non-target sequence and the capture probe is perfectly complementary to a target sequence.

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, distinct independently detectable moieties are used to label each of the different labeled probes of the set. The ability to differentiate between and quantitate each of the independently detectable moieties provides the means to multiplex the hybridization assay because the data which correlates with the hybridization of each of the distinct independently detectable probes to a target sequence of interest can be correlated with the data for each of the independently detectable moieties. Because multiplex hybridization assays involve numerous probes and target sequences, there is a great potential for non-specific hybridization to adversely effect the reliability of the multiplex assay. However, application of the methods of this invention will substantially improve the sensitivity and reliability of multiplex probe-based hybridization assays.

In summary, the methods, kits and compositions of this invention are used to suppress binding of probes to non-target sequences thereby substantially improving sequence discrimination and dynamic range of the hybridization assay. These advantages substantially improve the sensitivity and reliability of probe-based assays in general and are particularly useful when employing multiplex methodologies and/or point mutation analysis.

BRIEF DESCRIPTION OF THE DRAWINGS

FIG. 4A is a schematic of a plate assay.

FIG. 4D is a tabular illustration of hybridization assay data.

FIG. 5A is a schematic of a plate assay.

FIG. 5B is a tabular illustration of hybridization assay data.

FIG. 5D is a tabular illustration of hybridization assay data.

FIG. 6A is a schematic of a plate assay.

FIG. 6B is a tabular illustration of hybridization assay data.

FIG. 6C is a tabular illustration of hybridization assay data.

FIG. 7 is a sequence schematic of the target and probe binding sites in *Neisseria gonorrhoeae* and *Neisseria meningitidis*.

FIG. 8A is a schematic of a plate assay.

FIG. 8B is a tabular illustration of hybridization assay data.

FIG. 8C is a tabular illustration of hybridization assay data.

DESCRIPTION OF THE PREFERRED EMBODIMENTS

Figure 1:
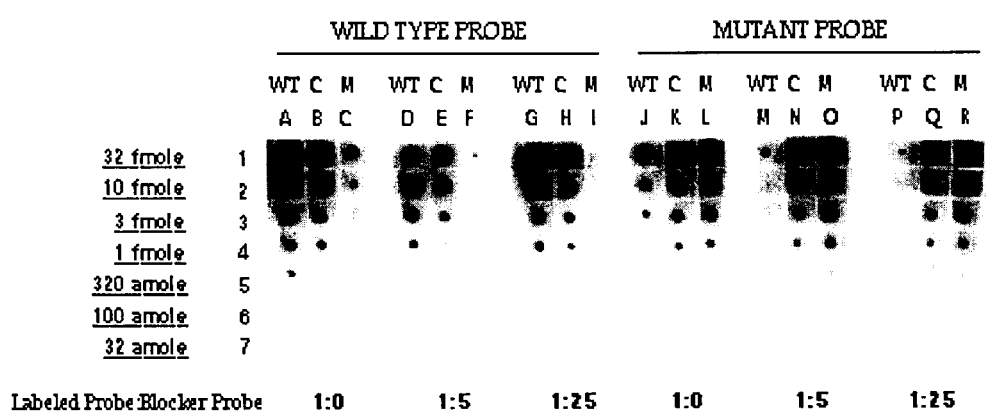
FIG. 1 is an autoradiogram generated by exposure of a film to enzymatically catalyzed chemiluminescence emanating from a nylon membrane.

1. Definitions:

a. As used herein, the term "Peptide Nucleic Acid" or "PNA" is defined as any of the compounds referred to or claimed as a Peptide Nucleic Acids in U.S. Pat. No. 5,539,082. The term "Peptide Nucleic Acid" or "PNA" shall also apply to those compositions referred to as Peptide Nucleic Acids in the following publications:

Diderichsen et al., Tett. Lett. (1996) 37, 475–478;
Fujii et al., Bioorg. Med. Chem. Lett. (1997) 7, 637–640;
Jordan et al., Bioorg. Med. Chem. Lett. (1997) 7, 687–690;
Krotz et al., Tett. Lett. (1995) 36, 6941–6944;
Lagriffoul et al., Bioorg. Med. Chem. Lett. (1994) 4, 1081–1082;
Lowe et al., J. Chem. Soc. Perkin Trans. 1, (1997) 1, 539–546;
Lowe et al., J. Chem. Soc. Perkin Trans. 1, (1997) 1, 547–554;
Lowe et al., J. Chem. Soc. Perkin Trans. 1, (1997) 1, 555–560;
Petersen et al., Bioorg. Med. Chem. Lett. (1996) 6, 793–796; and U.S. Pat. No. 5,623,049.

b. As used herein, the term "complementary sequence" or "complementary probe" is defined as the subunit sequence of a DNA, RNA or PNA oligomer designed to hybridize with exact complementarity to a nucleic acid sequence or subsequence.

c. As used herein, the term "PNA probe" is defined as any oligomer, comprising two or more PNA subunits (residues, monomer), suitable for hybridizing to a nucleic acid (DNA or RNA) sequence. The PNA probe may be labeled with a detectable moiety or may be unlabeled.

d. As used herein, the term "target sequence" is any defined nucleic acid sequence to be detected in an assay. The "target sequence" may comprise the entire sequence of interest or may be a subsequence of the nucleic acid target molecule of interest.

e. As used herein, the term "non-target sequence" is any defined nucleic acid sequence which is not a target sequence. The non-target sequences which generate the most background will be sequences which are closely related to the target sequence (e.g. point mutations).

f. As used herein, the term "single base pair mismatch" or "point mutation" is defined as the modification of a defined nucleic acid sequence such that a single nucleotide within the defined nucleic acid sequence has been substituted.

g. As used herein, the term "sensitivity" or "assay sensitivity" is defined as the difference in signal intensity caused by or attributable to the binding of detectable probe to its complementary sequence and any background or signal caused or attributable to any other source.

h. As used herein, the term "assay limit" or "limit of detection" is defined as the lower limit of signal intensity caused by the specific binding of detectable probe which can be detected above the background (noise).

i. As used herein, the terms "signal to noise" and "dynamic range" shall be interchangeable.

2. Detailed Description

General:

This invention relates to methods, kits and compositions suitable for the improved detection, quantitation and analysis of nucleic acid target sequences using probe-based hybridization assays. The invention is more specifically directed to methods, kits and compositions suitable for suppressing the binding of detectable probes to non-target sequences in an assay for a target sequence of a nucleic acid target molecule. Suppression of the nonspecific binding of detectable probe directly improves the sensitivity of the assay thereby improving the signal to noise ratio of the assay. Suppression of nonspecific binding will also result in improvements in reliability since the incidence of false positives and false negative should also be reduced. Because the methods, kits and compositions of this invention are directed to the suppression of nonspecific binding of probes to nucleic acids, they are particularly well suited for the development of sensitive and reliable probe-based hybridization assays designed to analyze for point mutations. The methods, kits and compositions of this invention should also find utility for the detection, quantitation or analysis of organisms (micro-organisms), viruses, fungi and genetically based clinical conditions of interest.

It has been surprisingly observed that the signal caused by the nonspecific binding of detectable probes to one or more non-target nucleic acid sequences can be dramatically suppressed by the addition of one or more unlabeled probes wherein the sequence of the one or more unlabeled probes is complementary to one or more non-target sequences to which the detectable probe binds in a nonspecific manner. For example, it has been observed that the addition of 25 equivalents of unlabeled PNA probe, having a single mismatch as compared with the labeled PNA probe, does not substantially alter the detection limit of the assay. However, the presence of the unlabeled PNA probe resulted in at least a 10 fold suppression in the binding of labeled PNA probe to the non-target sequence (point mutation) and a correlating improvement of approximately 30 fold, in the signal to noise ratio of the assay (see Example 4A and FIG. 1).

When the unlabeled PNA probe was present at 500 equivalents, there was very little loss of detectable signal (approximately 3 to 10 fold). However, suppression of binding of the labeled probe to a non-target sequence (point mutation) is substantially improved as compared with the experiment wherein only 25 equivalents of unlabeled PNA probe was present (Compare: Examples 4A and 4B of this specification). The results demonstrate that point mutation discrimination improved from approximately 10 fold in the absence of the unlabeled probe to greater than 1000 fold in the presence of high levels of unlabeled (blocker) PNA probe. Consequently, when employing the methods described herein, one can achieve several logs of improvement in point mutation discrimination and similar dramatic improvements in the dynamic range of the hybridization assay.

The applicants are not aware of any similar method suitable for obtaining such a dramatic suppression of binding to non-target sequences and the correlating improvement in signal to noise ratio. The data presented in Example 6, demonstrates the clear superiority of PNA probes as compared with DNA probes with regard to suppression of binding to non-target sequences, improvement in signal to noise ratios and point mutation discrimination.

In preferred embodiments of this invention, PNA probes are used either alone or in combination with nucleic acid probes. When combined with nucleic acid probes, the preferred combination involves unlabeled PNA probes used to suppress the binding of detectable (labeled) nucleic acid probes to non-target sequences. In the most preferred embodiment of this invention, both the detectable probes and unlabeled or independently detectable probes are PNA probes because this embodiment exhibits both the greatest ability to suppress binding to non-target sequences and the greatest ability to discriminate between point mutations.

Nucleic Acid Synthesis and Labeling

Those or ordinary skill in the art will recognize that both labeled, unlabeled or modified oligonucleotides are readily available. They can be synthesized using commercially available instrumentation and reagents or they can be purchased from numerous commercial vendors of custom manufactured oligonucleotides.

PNA Synthesis:

Methods for the chemical assembly of PNAs are well known (See: U.S. Pat. No. 5,539,082, entitled "Peptide Nucleic Acids" herein incorporated by reference). Chemicals and instrumentation for the support bound automated chemical assembly of Peptide Nucleic Acids are now commercially available. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the nucleic acid target sequence (the preferred orientation), the N-terminus of the PNA probe is the equivalent of the 5'-hydroxyl terminus of an equivalent DNA or RNA probe. Consequently, to design a PNA probe suitable for parallel binding to a nucleic acid target sequence, the C-terminus of the PNA probe will be the equivalent of the 5'-hydroxyl group of an equivalent DNA or RNA probe.

PNA Labeling:

PNA's are labeled using chemical methodologies well known to those of ordinary skill in the art. Chemical labeling of a PNA is analogous to peptide labeling. Because the synthetic chemistry of assembly is essentially the same, any method commonly used to label a peptide may be used to label the PNA. For example, the polymer may be labeled by condensation of a suitable detectable moiety to the amino terminus of the polymer during chemical assembly. Generally, the amino terminus is labeled by reaction with a detectable moiety having a carboxylic acid group or activated carboxylic acid group. Amide formation of this type is a well known and often utilized chemical reaction. The condensation reaction forms a very stable amide bond thereby generating the labeled PNA having a detectable moiety (label).

Similarly, the PNA can be extended with a linker moiety before the label (detectable moiety) is attached (e.g. Expedite™ PNA Linker; a.k.a. Fmoc-8-amino-3,6-dioxaoctanoic acid). Generally, linkers are used to minimize the adverse effects that bulky labeling reagents might have on hybridization properties of the PNA oligomers. Specialized reagents can be attached to the PNA terminus or the linker modified terminus for specific or optimized labeling reactions. For example, a terminal arylamine moiety can be generated by condensing a suitably protected 4-aminobenzoic acid derivative with either of the amino terminus of the PNA oligomer or the amino terminus of a linker extended PNA oligomer. After synthesis is complete, the labeled PNA is cleaved, deprotected and purified using well known methodologies.

Alternatively, the C-terminal end of the PNA can be labeled with a detectable moiety. Generally the C-terminal end of the PNA is labeled by first condensing a labeled moiety with the support upon which the labeled PNA is to be assembled. Next, the first synthon of the PNA can be condensed with the labeled moiety. Alternatively, one or more linker moieties or amino acids can be introduced between the labeled moiety and the PNA oligomer using commercially available reagents (e.g. Expedite™ PNA Linker; a.k.a. Fmoc-8-amino-3,6-dioxaoctanoic acid). Thereafter, the PNA is assembled, cleaved, deprotected and purified using the standard methodologies.

For example, the labeled moiety could be a lysine derivative wherein the ε-amino group is labeled with a detectable moiety. For example the moiety could be a fluorochrome such as 5(6)-carboxyfluorescein. Alternatively, the labeled moiety could be a lysine derivative wherein, the ε-amino group is derivatized with a 4-aminobenzoic acid moiety (e.g. 4-(N-(tert-butyloxycarbonyl)-aminobenzamide). Condensation of the lysine derivative with the support would be accomplished using standard condensation (peptide) chemistry. The α-amino group of the lysine derivative would then be deprotected and the PNA assembly initiated by condensation of the first PNA synthon with the α-amino group of the lysine amino acid. After complete assembly, the PNA oligomer is then cleaved from the support, deprotected and purified using well known methodologies.

According to another well known method, the label (detectable moiety) is attached to the PNA after it is fully assembled and cleaved from the support. This method would be preferable where the label (detectable moiety) is incompatible with the cleavage, deprotection or purification regimes commonly used to manufacture the PNA. For example, this method would be preferred when the label is an enzyme since the enzyme activity may be destroyed by any of the commonly utilized cleavage, deprotection or purification techniques.

By this method, the PNA will generally be labeled in solution by the reaction of a functional group on the PNA and a functional group on the label (detectable moiety). Those of ordinary skill in the art will recognize that the composition of the solution will depend on the nature of PNA and the detectable moiety (label). The solution may comprise organic solvent, water or any combination thereof. Generally, the organic solvent will be a polar non-nucleophilic solvent. Non limiting examples of suitable organic solvents include acetonitrile and N,N'-dimethylformamide. For labeling reactions involving enzymes, generally the organic concentration will be less than 50% and preferably less than 20%.

Generally the functional group on the PNA will be an amine and the functional group on the label will be a carboxylic acid or activated carboxylic acid. Non limiting examples of activated carboxylic acid functional groups include N-hydroxysuccinimidyl esters. If the label is an enzyme, preferably the amine on the PNA will be an arylamine. In aqueous solutions, the carboxylic acid group of either of the PNA or label (depending on the nature of the components chosen) can be activated with a water soluble carbodiimide. The reagent, 1-(3-dimethylaminopropyl)-3-ethylcarbodiimide hydrochloride (EDC), is a commercially available reagent sold specifically for aqueous amide forming condensation reactions.

Generally, the pH of aqueous solutions will be modulated with a buffer during the condensation reaction. Preferably the pH during the condensation is in the range of 4–10. When an arylamine is condensed with the carboxylic acid, preferably the pH is in the range of 4–7. When an alkylamine is condensed with a carboxylic acid, preferably the pH is in the range of 7–10. Generally the basicity of non-aqueous reactions will be modulated by the addition of non-nucleophilic organic bases. Non-limiting examples of suitable bases include N-methylmorpholine, triethylamine and N,N-diisopropylethylamine.

Non-limiting examples of detectable moieties (labels) suitable for labeling nucleic acid or PNA probes used in the practice of this invention would include chromophores, fluorochromes, spin labels, radioisotopes, enzymes, haptens and chemiluminescent compounds. Preferred fluorochromes include 5(6)-carboxyfluorescein, Cyanine 3 (Cy3) Dye and Cyanine 5 (Cy5) Dye. Preferred haptens include 5(6)-carboxyfluorescein, 2,4-dinitrophenyl, digoxigenin, and biotin. Preferred enzymes include soybean peroxidase, alkaline phosphatase and horseradish peroxidase. Other suitable labeling reagents and preferred methods of attachment would be recognized by those of ordinary skill in the art of PNA, peptide or nucleic acid synthesis.

Immobilization of Probes to Surfaces:

One or more probes will preferably be immobilized to a surface. In one embodiment, the probe can be immobilized to the surface using the well known process of UV-crosslinking. Alternatively, the probe can be covalently bound to a surface by the reaction of a suitable functional group on the probe. Methods are well known in the art for the attachment of oligonucleotide probes to surfaces. These procedures generally involve the reaction of a nucleophilic group (e.g. an amine or thiol) on a modified oligonucleotide with an electrophilic group on the support to be modified. Thus, one or more suitably prepared PNA probes bearing nucleophilic moieties can, likewise, be covalently immobilized to a suitable surface. Because native PNA possesses an amino terminus, PNA generally will not require modification to thereby immobilize it to a surface.

Conditions suitable for the immobilization of a PNA to a surface will generally be similar to those conditions describe above for the labeling of a PNA. The immobilization reaction is essentially the equivalent of labeling the PNA whereby the label is substituted with the surface to which the PNA probe is to be covalently immobilized. In preferred embodiments of this invention, surfaces comprising tresyl groups are reacted with arylamine modified PNA probes to thereby generate capture surfaces.

Probes:

The labeled and unlabeled probes of a set used for the practice of this invention will generally have a length of between 5 and 100 subunits. Preferably, the PNA probes will be 10 to 20 subunits in length and the nucleic acid probes will be 15–30 subunits is length. The labeled and unlabeled probes of a set may be nearly the same length or of identical length. When mixing PNA and nucleic acid probes in a set, typically the DNA probes will be longer to thereby generate probes which, when hybridized to target sequences, will have thermal stabilities (Tm values) which are comparable with the PNA probes (See: Egholm et al. Nature (1993) 365, 566–568).

In one embodiment, a detectable probe is completely complementary to the target sequence and an unlabeled or independently detectable probe, which is complementary to the non-target sequence, comprises at least one single nucleobase substitution (mismatch) as compared with the target sequence. Though, both the detectable probe and the unlabeled or independently detectable probe will hybridize, to some extent, to the target sequence, hybridization of the perfectly complementary detectable probe and the target sequence will be thermodynamically favored as compared with the hybridization of the non-complementary unlabeled or independently detectable probe and the target sequence. Similarly, hybridization of the unlabeled or independently detectable probe to the non-target sequence will be thermodynamically favored as compared with the hybridization of the non-complementary detectable probe and the non-target sequence.

In certain other embodiments, a detectable probe is selected to be substantially complementary to the target sequence such that the probe sequence need not comprise a nucleobase sequence which is exactly complementary to the target sequence to be detected in the probe-based hybridization assay. However, it is important that an unlabeled or independently detectable probe comprise a greater number of non-complementary nucleobases (point mutations) to the target sequence as compared with the detectable probe. Additionally, it is important that the detectable probe comprise a greater number of non-complementary nucleobases (point mutations) to the non-target sequence as compared with the unlabeled or independently detectable probe.

For example, the detectable probe can be designed to comprise a single nucleobase mismatch as compared with a probe which is exactly complementary to a target sequence. The unlabeled or independently detectable probe would be designed to comprise at least two nucleobase mismatches as compared with a probe which is exactly complementary to a target sequence to be detected. Similarly and by design, the detectable probe would then comprise at least two nucleobase mismatches as compared with a probe which is exactly complementary to a non-target sequence and the unlabeled or independently detectable probe would comprise less than two nucleobase mismatches as compared with a probe which is exactly complementary to a non-target sequence. Thus, when the detectable and unlabeled or independently detectable probes are present in the probe-based hybridization assay, hybridization of the more perfectly complementary detectable probe and target sequence will be thermodynamically favored as compared with the hybridization of the less complementary unlabeled or independently detectable probe and the target sequence. Similarly and by design, hybridization of the more perfectly complementary unlabeled and independently detectable probe and non-target sequence will be thermodynamically favored as compared with the hybridization of the less complementary detectable probe and the non-target sequence. Thus, if neither probe is perfectly complementary to the target sequence, hybridization of the more closely related probes and target or non-target sequences will be preferred.

Thus, when a detectable probe is designed to hybridize to a substantially complementary target sequence, it is a general requirement that a detectable probe comprise N nucleobase mismatches as compared with a probe which is exactly complementary to a target sequence. The one or more unlabeled or independently detectable probes comprise N+m nucleobase mismatches as compared with a probe which is exactly complementary to a target sequence. The integer N is 0, 1 or 2 and the integer m is 1, 2 or 3. Similarly, the unlabeled or independently detectable probe will comprise P nucleobase mismatches as compared with a probe which is exactly complementary to a non-target sequence and the one or more detectable probes will comprise P+q nucleobase mismatches as compared with a probe which is exactly complementary to a non-target sequence. The integer P is 0, 1 or 2 and the integer q is 1, 2 or 3, provided that N is greater than or equal to P.

Hybridization Assay:

In one embodiment, the invention is related to a method for suppressing the binding of detectable probe to a non-target sequence in an assay of a sample for a target sequence. The method comprises contacting the sample with a set containing two or more probes under conditions suitable for the probes to hybridize to nucleic acid. At least one of the probes is a detectable probe labeled with a detectable moiety and having a sequence complementary or substantially complementary to a target sequence. At least one of the other probes is an unlabeled or independently detectable probe having a sequence complementary or substantially complementary to a non-target sequence. The second step comprises detecting the presence, absence or quantity of a target sequence present in the sample by directly or indirectly detecting or quantitating the detectable moiety. At least one of the detectable probes or the unlabeled or independently detectable probes is a PNA probe. Preferably, the one or more unlabeled or independently detectable probes is a PNA probe. Most preferably, all probes of the set are PNA probes. In preferred embodiments, the detectable probe is perfectly complementary to a target sequence and the unlabeled or independently detectable probe is perfectly complementary to a non-target sequence which may be present in the sample.

The target sequence may comprise the entire sequence of interest or may be a subsequence of the nucleic acid target molecule of interest. The target sequence or nucleic acid target molecule of interest may comprise DNA or RNA.

According to the method, upon contacting the sample with the set of probes, a detectable probe will bind (hybridize) to the complementary or substantially complementary target sequence, if present in the sample. Thereafter, the presence or amount of target sequence present in the sample is detected by directly or indirectly detecting the presence, absence or quantity of detectable moiety (label). Generally, the one or more detectable moieties are used to identify or quantitate the probe to which they are attached. However, the detectable moieties are indirectly used to identify or quantitate the presence or amount of target sequence present in the sample. Consequently, the assay must be designed to correlate the presence of the detectable moiety with the hybridization of the detectable probe to the target sequence.

Generally, the unbound or non-specifically bound detectable probe will be removed so that the presence of the detectable moiety is a true indicator of the presence, absence or quantity of target sequence present in the sample. Thus, in certain embodiments, the probe/target sequence is separated from the detectable probe. For example, either the complex or the detectable probe may be immobilized to a support so that the other assays components are easily washed away. Alternatively, the components are separated by size using a chromatographic process. In other embodiments, the detectable moiety of the probe is detectable only when hybridized to the target sequence and, therefore, the excess detectable probe need not be removed from the sample to obtain useful hybridization information (See: Tyangi et al., Nature Biotech. (1996), 14, 303–308). In still another embodiment, the detectable moiety may be cleaved from the probe/target sequence and thereafter detected or quantitated (See: U.S. Pat. No. 5,410,068 entitled "Succinimidyl Trityl Compounds and a Process for Preparing Same" which is herein incorporated by reference).

Nonetheless, it is the correlation between hybridization and the presence, absence or amount of detectable moiety which must be maintained by appropriate design of the hybridization assay. Consequently, in certain embodiments, the complex formed between the detectable probe and target sequence may be dissociated to thereby retrieve the detectable probe for analysis. For example, this may be preferred where the target sequence has been immobilized to a surface. The MASDA technique previously described would be an example of a suitable format for dissociating the probe/target sequence complex to thereby generate information about the one or more detectable probes which hybridized to the one or more immobilized target sequences present in the sample to be analyzed.

Generally, a detectable probe will bind most strongly to a closely related sequence to thereby generate undesirable background signal. Closely related sequences are sequences having nearly identical nucleotide composition. Nonspecific binding occurs because the target and non-target sequences are so closely related that the detectable probe is very nearly the complement to the non-target sequence. Point mutations are very closely related sequences because they differ by the substitution of a single nucleotide. Consequently, single point mutations are very difficult to distinguish in a probe-based assay. Because the non-specific binding of the detectable probe to a non-target point mutation can be dramatically reduced in the presence of an unlabeled probe which is complementary to one or more closely related non-target sequences which may be in the sample of interest, this invention is very well suited to improving the sensitivity and reliability of probe-based point mutation analysis.

According to the method, there is no requirement that only a single detectable (labeled) probe be used. A mixture of two or more detectable probes may be preferred when two or more target sequences are to be identified in the same assay. Moreover, the suppression of binding to non-target sequences and the associated improvements in signal to noise ratios make the method of this invention particularly attractive when applied in a multiplex analysis of one or more samples for one or more conditions of interest. A multiplex assay would require numerous detectable probes wherein each detectable probe was used to detect, identify or quantitate a individual organism, fungi, virus or clinical condition of interest. Preferably, two or more detectable probes will comprise independently detectable moieties to thereby simplify the analysis of the data.

According to the method, there is no requirement that only a single unlabeled (or independently detectable) probe be used. A mixture of two or more unlabeled probes might be preferred when the labeled detectable probe binds non-specifically to more than one non-target sequence. A mixture of probes may also be preferred when the one or more of the non-target sequence(s) is not known with certainty. Large mixtures of unlabeled probes will most likely be preferred in multiplex analysis wherein numerous detectable probes are used and there are numerous closely related sequences which may be present in the sample.

Without intending to be bound to this description, it is believed that the binding of the detectable probe to the non-target sequence is suppressed because the unlabeled probe, which is complementary to the non-target sequence, will preferentially hybridize to the non-target sequence and thereby form a more thermodynamically stable complex than is formed by hybridization of the detectable probe and the non-target sequence. Consequently, the binding of the detectable probe to the non-target will be substantially diminished in the presence of the unlabeled probe as compared to the hybridization which occurs in the absence of the unlabeled (independently detectable) probe.

Because the method of this invention may be used in a hybridization assay, this invention will find utility in improving assays used to detect, identify of quantitate the presence or amount of an organism or virus in a sample through the detection of target nucleic acids associated with the organism or virus. (See: U.S. Pat. No. 5,641,631, entitled "Method for detecting, identifying and quantitating organisms and viruses" herein incorporated by reference). Similarly, this invention will also find utility in an assay used in the detection, identification or quantitation of one or more species of an organism in a sample (See U.S. Pat. No. 5,288,611, entitled "Method for detecting, identifying and quantitating organisms and viruses" herein incorporated by reference). This invention will also find utility in an assay used to determine the effect of antimicrobial agents on the growth of one or more microorganisms in a sample (See: U.S. Pat. No. 5,612,183, entitled "Method for determining the effect of antimicrobial agents on growth using ribosomal nucleic acid subunit subsequence specific probes" herein incorporated by reference). This invention will also find utility in an assay used to determine the presence or amount of a taxonomic group of organisms in a sample (See: U.S. Pat. No. 5,601,984, entitled "Method for detecting the presence of amount of a taxonomic group of organisms using specific r-RNA subsequences as probes" herein incorporated by reference.

Immobilization of the Target Sequence to a Surface:

In one embodiment of this invention, the target sequence or nucleic acid target molecule of interest is immobilized to a surface. Those of ordinary skill in the art will recognize the numerous methods suitable for immobilizing a nucleic acid to a surface. Preferably, the target sequence will be immobilized to a surface using UV crosslinking. When immobilized to a surface, the probes of the set will hybridize to the one or more target sequences of interest, if present. Immobilization to a surface is a preferred embodiment because non-specifically bound probes of the set can be easily washed away after hybridization to thereby more easily detect the presence, absence or quantity of the one or more detectable moieties.

The detectable moieties, present as a result of the formation of detectable probe/target nucleic acid complexes, may be detected on the support. Alternatively, the detectable probe/target nucleic acid complexes may be dissociated and the probes eluted from the support for independent analysis (e.g. the MASDA technique described in Shuber et al. Human Mol. Gen. (1997) 6, 337–347. In preferred embodiments, probes of distinct composition bearing independently detectable moieties are used to "probe" for differing target sequences of interest. Consequently, the presence of a particular independently detectable moiety in the aliquot eluted from the support can be used to detect, identify or quantitate the presence or amount of an organism, virus, fungi or clinical (disease) state of interest. In a preferred embodiment, each of the independently detectable moieties is an independently detectable mass marker and mass spectrometry is used to identify the one or more probes present in the aliquot. Preferably, positive-ion Fast Atom Bombardment Tandem Mass Spectrometry is used to identify the probes present in the aliquot (See: Takao et al., Rapid Comm. Mass. Spec. (1994), 925–928).

Detectable and Independently Detectable Moieties:

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, distinct independently detectable moieties are used to label the different probes of a set. The ability to differentiate between and/or quantitate each of the independently detectable moieties provides the means to multiplex the hybridization assay because the data which correlates with the hybridization of each of the distinctly (independently) labeled probes to a target sequence of interest can be correlated with the data for each of the independently detectable moieties. Because multiplex hybridization assays involve numerous probes and target sequences, there is a great potential for non-specific hybridization to adversely effect the sensitivity and reliability of the assay. Consequently, the sensitivity and reliability of multiplex probe-based assays should be improved when applying the methods, kits and compositions of this invention to multiplex sample analysis.

In a simple embodiment of the invention, there is a target sequence, a non-target sequence, a single detectable probe complementary to the target sequence and an unlabeled probe complementary to a non-target sequence. Though both PNA and nucleic acid probes are inherently detectable because they absorb ultraviolet light at 260 nanometers, the presence of the labeled probe (and the target nucleic acid/PNA probe complex) can be independently detected because of the unique properties of the detectable moiety (label). For example, the labeled (detectable) PNA probe could be labeled with a chromophore, a fluorochrome, a spin label, a radioisotope, an enzyme, a hapten or a chemiluminescent compound. Non limiting examples of preferred enzymes include, alkaline phosphatase, soybean peroxidase and horseradish peroxidase. Non-limiting examples of preferred haptens include, 5(6)-carboxyfluorescein, biotin, 2,4-dinitrophenyl and digoxigenin. Non-limiting examples of preferred fluorochromes include 5(6)-carboxyfluorescein, cyanine 3 dye and cyanine 5 dye. Non-limiting examples of preferred chemiluminescent compounds include luminol 1,2-dioxetanes.

Provided however, that the detectable moieties are independently detectable, there is no requirement that any of the probes be unlabeled. Indeed, it may be preferable to perform the method of this invention with two, or more, labeled PNA probes wherein the labels (detectable moieties) are independently detectable provided that the probe suppresses the binding of the other probe to their respective, non-target sequences.

Independently detectable moieties are moieties (labels) which, when both are present in a sample each, can be assayed for independently whereby the presence of the moiety of interest is not significantly affected by signal generated for the one or more other independently detectable moieties in the sample. For example, two fluorochromes could be used as labels for the PNA probes, provided the emission wavelengths of each fluorochrome were independently detectable (e.g. 5(6)-carboxyfluorescein and cyanine-3-dye(Cy3)). Alternatively two enzymes could be used as labels for the probes, provided the activity of the enzymes can be independently detected. For example, the activity of soybean peroxidase and alkaline phosphatase can be independently determined. Thus, the detectable probe is the probe which is sought to be presently detected and the unlabeled or independently detectable probe is the probe which is subsequently or independently detected.

Consequently, in still another embodiment of the invention, a mixture of four labeled, but independently detectable probes, could be used to analyze for and/or quantitate the relative abundance of point mutations of a target sequence in a sample. The set of probes would consist of four independently detectable probes wherein the sequence of each of the probes differed as a point mutation by relation to the other three. Thus, each of the probes is complementary to one of the four possible point mutations of a target sequence, and by relation, the other three probes are complementary to a non-target point mutation of that sequence. According to the method, the detectable probe would be the probe for which the signal for the detectable moiety of interest was sought to be presently detected. The assay could then be repeated three times wherein each time, a different independently detectable moiety was sought to be detected. In each of the four assays, the three independently detectable probes would thereby suppress the binding of the detectable probe to the non-target point mutations of the target sequence. Thus, the presence or absence of each of the point mutations could be detected with greater sensitivity and reliability in each of the four assays because the non-specific binding of the detectable probe to each of the specific non-targeted point mutated sequence is suppressed. Moreover, when compared with a standard curve, the relative abundance of the target point mutations could be determined by comparison of the signal intensity obtained for each of the four assays. Alternatively, the intensity of the point mutation could be determined by simultaneously detecting the four independently detectable moieties in a single assay. For example, the assay described above might be a simple multiplex assay used to analyze for a single point mutation in a target sequence of interest.

Order of Probe Addition/Incubation Period:

In a preferred embodiments, the one or more unlabeled or independently labeled probes are incubated with the sample for a first period of time, under conditions suitable for probes to hybridize to nucleic acid. Then, the one or more detectable probes are incubated with the sample for a second period of time under conditions suitable for probes to hybridize to nucleic acid. When using unlabeled or independently labeled PNA probes, the best signal to noise ratios are obtained when the first incubation period is 20 minutes or less. The applicants have determined that the application of these conditions provide the best results particularly when using unlabeled or independently detectable PNA probes to suppress the binding of detectable probes to non-target sequences.

Equivalents of Unlabeled or Independently Labeled Probe:

The applicants have surprisingly determined that the presence of between 2–500 equivalents of unlabeled or independently detectable probe (as compared with the number of equivalents of detectable probe) does not dramatically reduce the limit of detection of signal in the hybridization assay. However, as the ratio of unlabeled or independently detectable PNA probe to detectable probe increases the binding of the detectable probe to non-target sequence is dramatically reduced. Consequently, the signal to noise ratio dramatically improves as the ratio of unlabeled or independently detectable PNA probe to detectable probe is increased. The applicants have not observed any conditions whereby increasing the ratio of unlabeled probe to detectable probe is detrimental to the overall sensitivity and reliability of the hybridization assay. Consequently, the ratio of unlabeled or independently detectable probe to detectable probe is preferably greater than or equal to two.

Kits:

This invention also relates to kits suitable for suppressing the binding of a detectable probe to a non-target sequence in an assay of a sample for a target sequence. In one embodiment, the kit comprises a set of two or more PNA probes wherein, at least one of the probes is a detectable probe labeled with a detectable moiety and having a sequence complementary or substantially complementary to a target sequence. At least one of the other probes is an unlabeled or independently detectable probe having a sequence complementary or substantially complementary to a non-target sequence. PNA or nucleic acid probes may be used, provided, at least one of either a detectable probe or an unlabeled or independently detectable probe is a PNA probe. Preferably, the detectable probes are nucleic acid probes and the one or more unlabeled or independently detectable probes are PNA probes. Most preferably all probes are PNA probes. In preferred embodiments, the detectable probe is perfectly complementary to a target sequence and the unlabeled or independently detectable probe is perfectly complementary to a non-target sequence which may be present in the sample.

The kits of this invention may optionally contain instructions, buffers, DNA, RNA, instruments or any other item desirable for performing the assay.

There is no requirement that the kit comprise a single detectable probe because the assay may be designed to detect two or more target sequences simultaneously. There is no requirement the kit comprise only one unlabeled or independently label probe because there may be a need to suppress the binding of the detectable probe to more than one non-target sequence. Consequently, in one preferred embodiment, the kit comprises a set of detectable probes wherein each of the different probes of the set comprises an independently detectable moiety. In a preferred embodiment, the detectable probes of the set are nucleic acid probes and all other probes of the set are unlabeled PNA probes having a defined sequence and which hybridize to one or more non-target sequences which may be present in the sample. In another embodiment, all the probes of the set are PNA probes and each of the differing detectable PNA probes of the set comprise independently detectable moieties.

Kits of this invention will find utility in improving assays used to detect, identify of quantitate the presence or amount of an organism or virus in a sample. Similarly, the kits of this invention will also find utility in an assay used in the detection, identification or quantitation of one or more species of an organism in a sample. The kits of this invention will also find utility in an assay used to determine the effect of antimicrobial agents on the growth of one or more microorganisms in a sample. The kits of this invention will also find utility in an assay used to determine the presence or amount of a taxonomic group of organisms in a sample.

In one embodiment, the kit comprises a set of two PNA probes, wherein the first PNA probe has a sequence complementary to the target sequence and is labeled with a detectable moiety. The second PNA probe is unlabeled and has a sequence complementary to a non-target sequence which may be present in the sample. In a more preferred embodiment, the target and non-target sequences are related as point mutations.

In another embodiment, the kit comprises a set of four probes, wherein the probes of the set consist of a single detectable probe labeled with a detectable moiety and having a sequence complementary to the target sequence. The three unlabeled probes each have a defined sequence which is complementary to a non-target sequence which may be present in the sample. In a more preferred embodiment, the target and non-target sequences are related as point mutations.

Alternatively, the detectable probe of the set is a nucleic acid probe and the other probes of the kit are unlabeled PNA probes each having a defined sequence which is complementary to a non-target sequence which may be present in the sample. In a more preferred embodiment, the target and non-target sequences are related as point mutations.

Compositions:

The compositions of this invention may exist as a powder or they may comprise a solution of one or more components dissolved or suspended in a solvent. Suitable solvents include water or a mixture of water and an organic solvent. Non limiting examples of suitable organic solvents include acetonitrile, formamide, dimethylformamide, methanol, ethanol, isopropanol, tetrahydrofuran and 1,4-dioxane. The composition may comprise one or more organic or inorganic salts to thereby adjust the ionic strength of the composition. The composition may comprise one or more inorganic or organic detergents. The composition may comprise one or more buffers to thereby adjust the pH of the composition.

In one embodiment, this invention relates to a composition for suppressing the binding of a detectable probe to a non-target sequence in an assay of a sample for a target sequence. The composition consists of a set of two probes wherein, one of the probes is a detectable probe labeled with a detectable moiety and having a sequence complementary to the target sequence. The other probe is an unlabeled or independently detectable probe having a sequence complementary to a non-target sequence. PNA or nucleic acid probes may be used, provided, at least one of either a detectable probe or an unlabeled or independently detectable probe is a PNA probe. Preferably, the probes are PNA probes. The probes of the composition may be designed to hybridize specifically to complementary target or non-target sequences wherein the target. and non-target sequences are related as point mutations. In a preferred embodiment, the detectable probe is a nucleic acid probe and the other probe is an unlabeled PNA probe.

In another embodiment, the invention relates to a composition for suppressing the binding of a detectable probe to a non-target sequence in an assay of a sample for a target sequence. The composition consists of a set of four probes wherein, one of the probes is a detectable probe labeled with a detectable moiety and having a sequence complementary to the target sequence. The other three probes are unlabeled or independently detectable probes having a sequence complementary to a non-target sequence. PNA or nucleic acid probes may be used, provided, at least one of either a detectable probe or an unlabeled or independently detectable probe is a PNA probe. Preferably, the probes are PNA probes. Preferably the probe set contains probes which hybridize to target and non-target sequences which are related as the four possible sequence variations for a single point mutation. In a preferred embodiment, the detectable probe is a nucleic acid probe and the other three probes are unlabeled PNA probes.

The compositions of this invention will find utility in improving assays used to detect, identify of quantitate the presence or amount of an organism or virus in a sample. Similarly, the compositions of this invention will also find utility in an assay used in the detection, identification or quantitation of one or more species of an organism in a sample. The compositions of this invention will also find utility in an assay used to determine the effect of antimicrobial agents on the growth of one or more microorganisms in a sample. The compositions of this invention will also find utility in an assay used to determine the presence or amount of a taxonomic group of organisms in a sample.

Capture Assays:

Still another embodiment of this invention is related to a method for suppressing the binding of a non-target sequence to a capture probe immobilized on a surface in a capture assay of a sample for a target sequence of a nucleic acid target molecule. Capture assays are often preferred because the surfaces can be repetitively treated whereby the reagents are easily added and removed. Moreover, arrays of capture probes can be constructed to thereby enable simultaneous analysis of a sample for the presence, absence or quantity of numerous nucleic acid target molecules. Consequently, capture assays are easily adapted for multiplex sample analysis.

The method comprises contacting the sample with a solution containing one or more blocking probes under conditions suitable for the blocking probes to hybridize to nucleic acid. The blocking probes are complementary or substantially complementary to one or more non-target sequences which when present in the sample may bind non-specifically to the capture probe to generate a detectable signal in the assay. The sample is also contacted with a capture probe immobilized on a surface. The conditions are suitable for the target sequence, if present, to hybridize to the capture probe. The capture probe is complementary or substantially complementary to the target sequence and thereby forms a capture probe/target sequence complex upon hybridization. Finally, the presence or amount of nucleic acid target molecule which becomes immobilized to the surface by the formation of the capture probe/target sequence complex is detected, identified or quantitated. In preferred embodiments, the blocking probe is perfectly complementary to a non-target sequence and the capture probe is perfectly complementary to a target sequence.

The nucleic acid target molecule which is sought to be captured by operation of the method of this invention may be DNA or RNA. Both nucleic acid or PNA blocker probes are suitable for use in the capture assay of this invention. Preferably, the blocker probes are PNA probes. Both nucleic acid or PNA capture probes are suitable for use in the capture assay of this invention, provided at least one of a capture probe and a blocking probe is a PNA probe. Preferably, the one or more capture probes are PNA probes. In one preferred embodiment, the capture probes are nucleic acid probes and the blocker probes are PNA probes. In preferred embodiments, the capture probes and blocker probes are designed to hybridize specifically to target and non-target sequences which are closely related.

In a preferred embodiment of this method, the surface comprises an array of probes, wherein each distinct capture probe in the array is designed to capture a specific nucleic acid target molecule. The presence or quantity of a nucleic acid target molecule is indicative of the presence or quantity of a specific organism, virus, fungi or clinical (disease) state of interest in the sample.

Thus, capture assays of this invention will find utility in improving the detection, identification or quantitation of the presence or amount of an organism or virus in a sample. Similarly, the capture assays of this invention will also find utility in the detection, identification or quantitation of one or more species of an organism in a sample. The capture assays of this invention will also find utility in the determination of the effect of antimicrobial agents on the growth of one or more microorganisms in a sample. Finally, the capture assays of this invention will also find utility in determining the presence or amount of a taxonomic group of organisms in a sample.

Because hybridization of the capture probe to the target sequence results in the formation of a capture probe/target nucleic acid complex, the presence or amount of nucleic acid target molecule immobilized to the surface can be detected using a labeled antibody which specifically interacts with the capture probe/target sequence complex which is formed on the surface. If the capture probe is a nucleic acid probe, the complex formed on the surface by capture is a nucleic acid/nucleic acid complex. Thus, a labeled anti-nucleic acid/nucleic acid antibody can be used to detect the presence, absence or amount of the nucleic acid/nucleic acid complex (See: U.S. Pat. No. 5,200,313 entitled "Nucleic Acid Hybridization Assay Employing Detectable Anti-Hybrid Antibodies" herein incorporated by reference). If the capture probe is a PNA probe, the complex formed on the surface by capture of the target sequence will be a PNA/nucleic acid complex. Consequently, a labeled anti-PNA/nucleic acid antibody will be used to detect the presence, absence or amount of the PNA/nucleic acid complex (See: U.S. Pat. No 5,612,458 entitled "Antibody to PNA/nucleic acid Complexes" herein incorporated by reference). Generally, either of the antibodies can be labeled with a detectable moiety. Non-limiting examples of such detectable moieties can be selected from the group consisting of a chromophore, a fluorophore, a spin label, a radioisotope, an enzyme, a hapten and a chemiluminescent compound. Non-limiting examples of suitable enzymes include alkaline phosphatase, soybean peroxidase and horseradish peroxidase. Non-limiting examples of suitable haptens include fluorescein, biotin, 2,4-dinitrophenyl and digoxigenin.

Detection of capture probe/target nucleic acid complexes using an antibody directed to the capture probe/target sequence is particularly well suited for analysis of arrays because the individual PNA capture probe or nucleic acid capture probes need not be individually labeled. Moreover, the blocking probes also need not be labeled. Methods employing unlabeled probes are preferred because the probes generally cost less to produce and are easier to synthesize and purify. Moreover, a single reagent is used to detect and quantitate the presence or amount of the capture probe/target sequence complex.

In another embodiment, the presence or amount of target sequence immobilized to the surface is detected using a detector probe which hybridizes to a second target sequence of the nucleic acid target molecule. The detector probe may be a PNA probe or a nucleic acid probe. The detector probe may be labeled with a detectable moiety. Detectable moieties suitable for labeling the PNA or nucleic acid probes of this invention have been previously described.

In certain embodiments, the Hybridization Assay described above can be used to suppress the binding of one or more detector probes to the one or more non-second target sequences to thereby improve the reliability of the assay. According to the method, the set of probes would comprise at least one detector probe having a sequence complementary to a second target sequence of interest. The set of probes would also comprise at least one non-second target sequence probe complementary to a non-second target sequence which might be present in the sample.

Alternatively, the detector probes need not be labeled with detectable moieties but their presence, absence or quantity can be determined using labeled antibodies. If the detector probe is a nucleic acid probe, the complex formed on the surface is a detector (nucleic acid) probe/second target sequence complex. As previously described, a labeled anti-nucleic acid/nucleic acid antibody can be used to detect the presence, absence or amount of the detector (nucleic acid) probe/second target sequence complex. If the detector probe is a PNA probe, the complex formed on the surface is a detector (PNA) probe/second target sequence complex. Consequently, a labeled anti-PNA/nucleic acid antibody can be used to detect the presence, absence or amount of the detector (PNA) probe/second target sequence.

When using labeled antibodies to detect the detector probe/second target sequence complex in a capture assay, the nature of the capture probes and the detector probes should be different. For example, if the capture probes are nucleic acid and the detector probes are PNA probes, the hybrids can be independently detected by using the appropriate labeled antibody. In this example the labeled anti-PNA/nucleic acid antibody will be used to detect or quantitate the presence or amount of detector probe present since no cross reaction should occur with the capture probe/target sequence complex. Similarly, the capture probe/target sequence complex can be specifically detected using the labeled anti-nucleic acid/nucleic acid antibody since no crossreaction with the detector PNA probe/second target sequence complex should occur.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

Example 1

Synthesis of 4-(N-(tert-butyloxycarbonyl)-aminobenzoic acid

To 100 mM of methyl-4-amino benzoic acid stirring in 150 mL of dioxane was added 110 mM of di-tert-butyl-dicarbonate. The reaction was warmed to 70–80° C. and let stir for about 48 hours. The solvent was then evaporated under reduced pressure and the residue redissolved in about 300 mL of ethylacetate. The organic layer was then washed three times with 10% aqueous citric acid, dried ($Na_2SO_4$), filtered and evaporated to a solid. The solid was then suspended in 150 mL of 1N NaOH and 50 mL acetone. The saponification of the ester was allowed to run overnight until complete hydrolysis was observed by thin layer chromatography (TLC). To the solution was added citric acid until the pH of the solution was approximately 4. The solid was then collected by vacuum filtration and dried in a vacuum oven at 50° C. Yield 20.3 g, 85%. The product was a single peak when analyzed by HPLC using 0.1% trifluoroacetic acid (TFA) and a linear acetonitrile gradient.

$^1$H-NMR ($d_6$-DMSO) δ=9.7 (s, 1H), 7.8 (d, 2H), 7.6 (d, 2H), 1.5 (s, 9H).

Example 2

Synthesis of Peptide Nucleic Acids

Peptide Nucleic Acids (PNAs) were synthesized using commercially available chemicals and instrumentation from PerSeptive Biosystems, Inc. Labeling of the amino terminus of the PNA oligomer with a linker group while the oligomer was still support bound was accomplished by condensation of two subunits of Expedite PNA Linker (P/N GEN063032) using one of the auxiliary positions of the PNA synthesizer and the standard coupling cycle. To the amino terminus of the elongated polymer was condensed 4-(N-(tert-butyloxycarbonyl)-aminobenzoic acid (see Example 1). After desired modification of the amino terminus of the polymer, the oligomers were then cleaved from the support and deprotected according to the manufactures instructions. The crude oligomer samples were then purified by High Performance Liquid Chromatography (HPLC) using 0.1% trifluoroacetic acid (TFA) and a linear acetonitrile gradient. This process yielded purified aryl amine terminating oligomers suitable for either conjugation with enzyme or suitable for use in the assay as an unlabeled probe (i.e. not conjugated to SBP).

Example 3

General Procedure for Conjugation of Arylamine Containing Peptide Nucleic Acids (PNA's) to Soybean Peroxidase or Alkaline Phosphatase Stock Solutions:

1. Probe Stock:

Purified arylamine terminated PNA probe, typically fifteen residues in length, was dissolved at a concentration of approximately 0.33 μmol per milliliter in 50% aqueous dimethylformamide (DMF).

2. Enzyme Stock:

Soybean peroxidase, conjugate grade, obtained from Enzymol International, Columbus Ohio, was dissolved at a concentration of 2.65 mg per milliliter in an aqueous buffer comprised of 3 M NaCl, 10 mM $MgCl_2$, 0.1 mM $ZnCl_2$ and 30 mM N-methylmorpholine adjusted to pH 7.6 with 12 N hydrochloric acid.

3. 30% Aqueous DMF:

An aqueous DMF solution was prepared by combining three volumes of DMF with 7 volumes of water.

4. MES Buffer

An 0.2 M solution of 4-morpholineethanesulfonic acid (MES) in water was prepared (not pH adjusted).

5. Glycine Solution

A solution comprised of 0.5 M glycine and 0.25 M sodium hydroxide in water was prepared.

6. Wash Buffer

An aqueous buffer comprised of 1.5 M NaCl, 5 mM $MgCl_2$, 0.1 mM $ZnCl_2$ and 15 mM N-methylmorpholine adjusted to pH 7.6 with hydrochloric acid was prepared.

7. Storage Buffer

An aqueous buffer comprised of 3 M NaCl, 10 mM $MgCl_2$, 0.1 mM $ZnCl_2$, and 30 mM N-methylmorpholine adjusted to pH 7.6 with 12 N hydrochloric acid was prepared.

Conjugation Procedure:

In a small reaction tube was combined 10 μL of Enzyme Stock, 12.5 μL of 30% Aqueous DMF, and 7 μL of Probe Stock. In a separate tube was placed 1 mg of 1-(3-dimethylaminopropyl)-3-ethylcarbodiimide hydrochloride (EDC) and 7 μL of MES Buffer. These reagents were mixed until the EDC had dissolved in the MES Buffer. The EDC/MES Buffer solution was then added to the tube containing the enzyme and probe (Reaction Mixture). The contents were mixed, and the tube was placed at 5° C. for 40 min. To the Reaction Mixture was then added 7 μL of Glycine Solution. The contents were again mixed and the tube was placed at 5° C. for a further 20 minutes. The contents of the tube were diluted with 50 μL of Wash Buffer and then transferred to the cup of an Ultrafree microconcentrator (30,000 molecular weight cut-off, Millipore Corporation, Bedford Mass.). The concentrator was spun at 5,000×g until ~90% of the liquid had been removed from the cup. An additional 50 μL of Wash Buffer was added to the cup and the device spun again to remove 90% of the liquid. This washing procedure was repeated two additional times. The contents of the cup were then diluted to a volume of 1 milliliter in Storage Buffer. The absorbance of this solution at 260 nM was used to estimate the concentration of the PNA-enzyme conjugate for subsequent assays (0.05 absorbance units at 260 nanometers per milliliter was estimated to be 0.33 nmol per milliliter based on an estimated extinction for a PNA 15-mer of 150 optical density units per μmole of probe).

Example 4

Suppression of the Nonspecific Binding of Detectable Probe in a Probe Based Assay Overview of Experiments A and B:

Two DNA oligonucleotides which differed in sequence by a single base (point mutation) were detected in experimental assays using labeled (detectable) PNA probes, each of which was complementary to one of the two target sequences. Experiments A and B were performed to examine, compare and quantitate the effects associated with the addition of unlabeled probe on the hybridization assay performance. Experiments A and B were generally performed in the same manner except that ratios of labeled to unlabeled probe were substantially greater in Experiment B. The results of Experiments A and B demonstrate a dramatic suppression of binding of labeled probe to non-target nucleic acid which differs from the target nucleic acid as a point mutation. The suppression of binding to non-target sequence results in a correlating dramatic improvement in the signal to noise ratio for the hybridization assay.

Probes and Targets (Exp. A & B):

Target DNA oligonucleotides were obtained from a commercial vendor of custom synthesized DNA. The biotin was attached by the commercial vendor using commercially available biotin amidites. Labeled and unlabeled peptide nucleic acid (PNA) probes were prepared as described in Examples 2 and 3 above.

Target DNA Oligomer Sequences:
Wild Type: 5' Biotin-GTG GTA GTT GGA GCT GGT GGC GTA-OH 3' SEQ ID NO: 1
Mutant: 5' Biotin-GTG GTA GTT GGA GCT TGT GGC GTA-OH 3' SEQ ID NO: 2

Labeled (Detectable) PNA Probes:
PNA-Wild Type: $H_2NC(O)$-ACC TCG ACC ACC GCA-(linker)$_2$-P-SBP
PNA-Mutant: $H_2NC(O)$-ACC TCG AAC ACC GCA-(linker)$_2$-P-SBN Unlabeled PNA Probes:
PNA-Wild Type: $H_2NC(O)$-ACC TCG ACC ACC GCA-(linker)$_2$-P-NH$_2$
PNA-Mutant: $H_2NC(O)$-ACC TCG AAC ACC GCA-(linker)$_2$-P-NH$_2$ (Notes: For the PNA oligomers, "linker" designates the Expedite PNA linker attached to the amino terminus of the PNA (equivalent to the 5' hydroxyl end of a DNA or RNA probe for hybridization purposes) and the letter "P" designates the 4-amino benzoic acid moiety attached thereto. SBP designates the Soybean Peroxidase enzyme).

Reagents (Exp. A & B):
Pre-Hybridization and Hybridization Buffer
  50% Formamide
  20 mM [Tris[hydroxymethyl]amino]methane (TRIS) pH 9.4
  1.0% Casein
  2.3% Polyoxyethylene sorbitan Monolaurate (TWEEN-20)
Oligo Dilution Buffer
  100 mM TRIS pH 7.6
  20 mM Ethylenediaminetetracetic acid (EDTA)
20×SSC
  3 M NaCl
  300 mM $C_6H_5Na_3O_7 \cdot 2H_2O$ (Sodium Citrate Trisodium Salt: Dihydrate)
Wash Buffer
  2×(SSC)
  0.1% Sodium Dodecyl Sulfate
  0.5% Casein
Blocking Buffer
  500 mM NaCl
  50 mM TRIS pH 9.0
  0.5% Casein
High pH Blocking Buffer
  100 mM TRIS pH 9.4
  100 mM NaCl
  10 mM $MgCl_2$
Nylon Membrane: Biodyne A™ (Pall, Inc.) was obtained from Gibco, BRL, Gaithersburg, Md.

The detection system was a commercially available luminol based chemiluminescent substrate (SuperSignal NA™ from Pierce Chemical). Signal was enzymatically catalyzed by the enzyme Soybean Peroxidase which was conjugated to the PNA probe (detectable moiety). The enzyme catalytically produced chemiluminescent signal which was detected using an autoradiographic film.

Experiment A
Assay Description:
PNA Probe Solutions:
Set 1 No unlabeled PNA probe
Set 2 1:5, Labeled (Detectable) probe:Unlabeled probe
Set 3 1:25, Labeled (Detectable) probe:Unlabeled probe Labeled (Detectable) PNA probes were diluted to a final concentration of 4 pmole/mL using Hybridization Buffer. Set 1 was a control so no unlabeled PNA probe was added. Unlabeled PNA probes were diluted to a final concentration of: 20 pmole/mL for Set 2, and 100 pmole/mL for Set 3, using Hybridization Buffer. Table 1, summarizes the components of the mixtures used to generate Sets 1, 2 and 3.

Wild Type Labeled Probe: 293 pmole/mL
Mutant Labeled Probe: 387 pmole/mL
Wild Type Unlabeled Probe: 5 pmole/μL (diluted in 50% formamide)
Mutant Unlabeled Probe: 5 pmole/μL (diluted in 50% formamide)

TABLE 1

| Set # | Probe Type | Wild Type probe | Mutant probe | Mutant unlabeled probe | Wild Type unlabeled probe | Hyb. Buffer |
|---|---|---|---|---|---|---|
| 1 | Wild Type | 3.4 μL | — | — | — | 46.6 μL |
| 1 | Mutant | — | 2.6 μL | — | — | 47.4 μL |
| 2 | Wild Type | 3.4 μL | — | 1 μL | — | 45.6 μL |
| 2 | Mutant | — | 2.6 μL | — | 1 μL | 46.4 μL |
| 3 | Wild Type | 3.4 μL | — | 5 μL | — | 41.6 μL |
| 3 | Mutant | — | 2.6 μL | — | 5 μL | 42.4 μL |

Method:

Each Target DNA oligomer was diluted to the following final concentrations, 100 fmole/μL, 32 fmole/μL, 10 fmole/μL, 3 fmole/μL, 1 fmole/μL, 320 amole/μL, and 100 amole/μL. A control set of dilutions was also made which consisted of 50% of each of the two oligomers at each dilution. For example, the control called 100 fmole/μL was made from equal volumes of the 100 fmole/μL dilution of each target DNA oligomer. The final concentration of each target DNA oligomer in the 100 fmole/μL control was 50 fmole/μL. For each hybridization, 0.32 μL of each of the target DNAs was spotted onto a nylon membrane. Six membranes containing each of the three dilution series (Mu, WT, and Control) were made. After spotting, the membranes were dried at 37° C. for 15 minutes, then irradiated with 254 nm @ 0.033 joules/cm$^2$ of light to crosslink the DNA to the membrane. Membranes were individually sealed in plastic bags.

Membranes were then pre-hybridized with 200 μL Hybridization Buffer in a 45° C. water bath for 1 hour. During pre-hybridization, membranes were periodically shaken. Next, 50 μL of probe mixtures were added to the bags, the bags were resealed, and hybridization was allowed to proceed for 30 minutes at 45° C. with periodic mixing.

Membranes were then washed together twice at room temperature in 100 mL of Wash Buffer. A third wash was carried out at 45° C. while shaking for 15 minutes. Membranes were blocked for 15 minutes while shaking in 100 mL Blocking Buffer. Membranes were blocked again for 5 minutes while shaking in 50 mL High pH Blocking Buffer. Membranes were blotted on Whatman membrane paper and put collectively into a new plastic pouch. Next, 500 μL of Pierce™ "Stable Peroxide NA" and 500 μL of Pierce™ "Luminol/Enhancer NA" were added to the pouch. The pouch was sealed and shaken at room temperature for 10 minutes. The membranes were again blotted onto paper then resealed in individual plastic pouches. The membranes were exposed to autoradiographic film for 2–5 minutes.

Results:

With reference to FIG. 1, the left half of the figure displays the membranes probed with wild type PNA probe conjugated to soybean peroxidase as the detectable moiety. With reference to FIG. 1, the right half displays membrane probed with the mutant PNA probe conjugated to soybean peroxidase as the detectable moiety. For convenience of interpreting the Figure, columns have been designated with the letters A–R and rows have been designated with the numbers 1–7. In each column of each membrane a dilution series of target DNA oligomer was applied. For each of the six membranes there was a column labeled "WT" for the wild type DNA target, "C" for the control (mixture of wild type and mutant target DNA) and "M" for the mutant DNA target. All six membranes were identical with respect to dimensions and DNA target location, type and concentration. DNA target oligomers were spotted approximately in the center of 3 mm×3 mm squares marked on the membrane. Dilution series were arranged vertically with the highest concentration of oligomer at the top and the lowest concentration at the bottom. The two sets of membranes (wild type-probed, and mutant-probed) were arranged from left to right as the relative molar concentration ratio of labeled (detectable) PNA probe to unlabeled PNA probe in the hybridization was increased from 1:0, 1:5, and 1:25. For the wild type probe, the "WT" dilution series represented specific signal, and the "M" dilution series represents non-specific signal. For the mutant probe, the "M" dilution series represents specific signal, and the "WT" dilution series represented non-specific signal.

With reference to FIG. 1, row 5, when either the wild type or mutant targets are probed with the perfectly complementary wild type or mutant probes, whether in the presence or absence of blocker probe, the lowest discernible level of detectable DNA was 320 amole (See: row 5, columns A, D, G, L, O and R). The strength of the signal at 320 amole of spotted target was slightly reduced, in the presence of the unlabeled mutant probe (Compare: row 5, column A to row 5, columns D and G). The mutant probe does not display any visible loss of signal in the presence of unlabeled probe (compare row 5, column L to row 5, columns O and R).

The control dilution series contained a 1:1 mixture of wild type and mutant target DNA. The amount of specific signal seen in the control lanes should be approximately the same (across rows) under all conditions tested if the presence of unlabeled probe does not significantly reduce specific signal, and if the two labeled probes behave in similar ways under the assay conditions. As can be seen by comparing the signals in columns B, E, H, K, N, and Q in FIG. 1, control signal was maintained across the six membranes. On each membrane, the control signal was approximately 50% of the specific signal at all levels tested as it should be (for example compare the signals in column K to those in column L).

The intensity of the signal caused by non-specific hybridization of the wild type or mutant labeled probe was, however, dramatically reduced in the presence of the unlabeled probe. For example, with reference to FIG. 1, compare the signal intensity of the labeled wild type probe hybridized to the mutant target (column C) with that obtained from the hybridization in the presence of the unlabeled mutant probe (See: columns F and I where the unlabeled mutant probe was present in the hybridization assay in 5 and 25 relative molar excess, respectively to the labeled wild type probe). In the absence of the unlabeled probe the non-specific signal was present at 3 fmole of target DNA (See: row 3, column C). Addition of 5 fold molar excess of unlabeled mutant probe reduced the intensity of the non-specific signal by approximately 10 fold so that about 32 fmole of mutant DNA is required to observe a signal (See: row 1, column F). Addition of 25 equivalents of unlabeled mutant probe reduced the intensity of the signal such that non-specific binding of the wild type probe to the mutant target was not detectable within the parameters of this experiment (See: row 1, column I).

Consistent with these results, when the labeled mutant probe was used for hybridization, the addition of a 25 fold relative molar excess of unlabeled wild type probe to the hybridization reaction resulted in approximately a 10 fold reduction of non-specific binding of the labeled mutant probed to the wild type DNA target. With reference to FIG. 1, compare column J (no unlabeled wild type probe) with columns M and P (unlabeled wild type probe in relative molar concentrations of 5 and 25). The mutant probe was detected at about 3 fmole of wild type target in the absence of any unlabeled wild type probe (row 3, column J). Addition of a 5 fold relative molar excess of unlabeled wild type probe reduced the intensity of the non-specific signal by approximately 10 fold such that about 32 fmole of wild type target DNA was required to observe a signal (row 1, column M). Addition of 25 molar equivalents of unlabeled wild type probe to the hybridization mixture reduced the intensity of the signal observed such that the lower limit of detection remained at about 32 fmole of target DNA (row 1, column P).

In conclusion, the results illustrated in FIG. 1 demonstrate that non-specific binding of labeled (detectable) PNA probes to non-complementary nucleic acid sequences can be suppressed by the addition of unlabelled PNA probes which are complementary to non-target sequences to which the labeled (detectable) PNA probe binds non-specifically. As shown here the ability to discriminate between the wild type and mutant targets goes up from 10 fold in the absence of the unlabeled probe to greater than 100 fold in the presence of unlabeled PNA probe.

Summary:

Estimated signal to noise ratio increased from approximately 10 to 320 for the labeled wild type probe in the absence and presence of unlabeled mutant probe, respectively. For the mutant oligonucleotide target, the estimated signal to noise ratio increased from approximately 3 to 100 for the labeled mutant probe in the presence and absence of unlabeled wild type probe, respectively. Consequently, point mutation discrimination was dramatically improved in the presence of the unlabeled (blocker) PNA probe.

Experiment B

Assay Description:

PNA Probe Solutions:

Table 2 displays the components of Hybridization Sets A (1–4) and B (1–4). Labeled (detectable) PNA probes were diluted to a final concentration of 5 pmole/mL with Hybridization Buffer. Unlabeled probes were aliquoted from a concentrated stock "(conc.)" of 333 pmole/μL, or a diluted stock "(dil)" of 5 pmole/μL. The stock which was used to prepare the sample for the hybridization assay is indicated in Table 2. Because Set 1 was a control, no unlabeled PNA probe was added. Unlabeled PNA probes were diluted to a final concentration of: 25 pmole/mL for group 2,500 pmole/mL for group 3, and 2.5 nmole/mL for group 4. As indicated in the table, the total volume of probe stock was 50 μL for all Hybridization Sets prepared. The 50 μL of probe stock was then diluted in 150 μL of Hyb. Buffer so that the total volume of solution applied to the membrane was 200 μL.

TABLE 2

| Set # | Labeled Probe Type | Wild Type labeled probe | Mutant labeled probe | Wild Type unlabeled probe | Mutant unlabeled probe | Hyb. Buffer |
|---|---|---|---|---|---|---|
| 1A | Wild Type | 3.4 μL | — | — | — | 46.6 μL |
| 2A | Wild Type | 3.4 μL | — | — | 1.0 μL (dil.) | 45.6 μL |
| 3A | Wild Type | 3.4 μL | — | — | 0.3 μL (conc.) | 46.3 μL |
| 4A | Wild Type | 3.4 μL | — | — | 1.5 μL (conc.) | 45.1 μL |
| 1B | Mutant | — | 2.6 μL | — | — | 47.4 μL |
| 2B | Mutant | — | 2.6 μL | 1.0 μL (dil.) | — | 46.4 μL |
| 3B | Mutant | — | 2.6 μL | 0.3 μL (conc.) | — | 47.1 μL |
| 4B | Mutant | — | 2.6 μL | 1.5 μL (conc.) | — | 45.9 μL |

Figure 2:
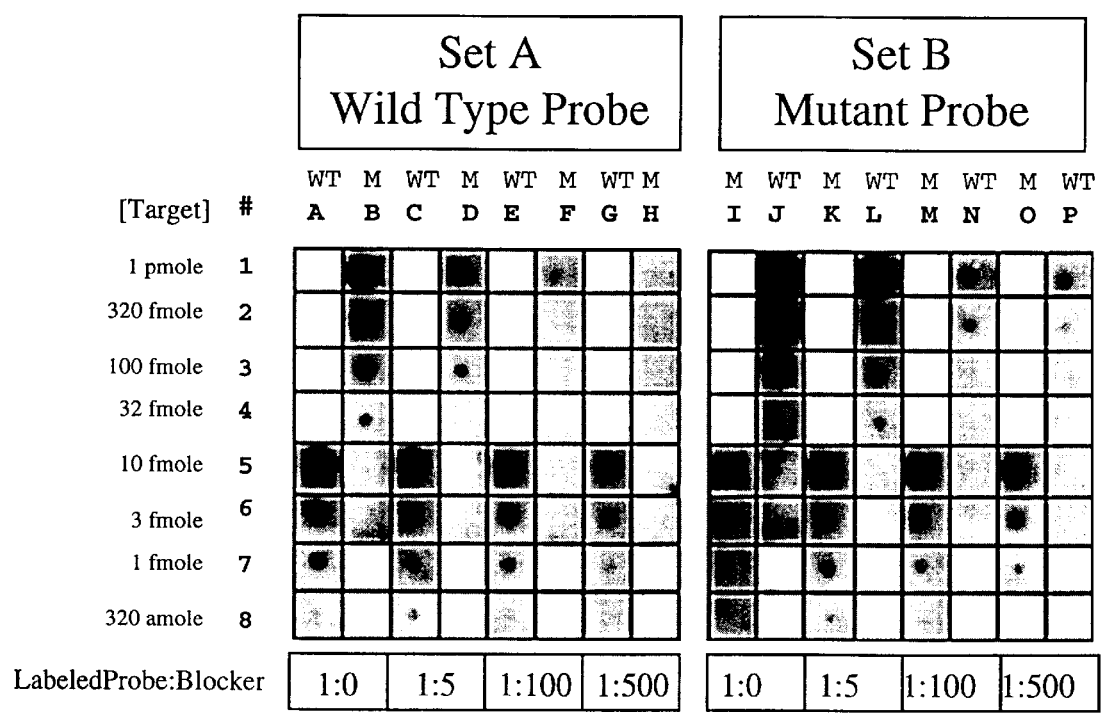
FIG. 2 is a composite electronic image of autoradiograms generated by exposure of a film to enzymatically catalyzed chemiluminescence emanating from a nylon membrane.

Method:

Dilutions of target oligonucleotides were made in Oligo Dilution Buffer to final concentrations of 3 pmole/μL, 1 pmole/μL, 320 fmole/μL, 100 fmole/μL, 32 fmole/μL, 10 fmole/μL, 3 fmole/μL, 1 fmole/μL, 320 amole/μL, and 100 amole/μL. Eight nylon membranes were prepared as described in Experiment A. Each membrane consisted of two columns of 6, 3×3 mm squares. Four membranes were designated as Set A, and the other four were designated as Set B. In the left column of Set A, aliquots of 0.32 μL of the six consecutive dilutions of the wild type target were spotted onto the membrane to generate a dot blot array of target nucleic acid present in half log steps in the range of 10 fmol to 32 amole (Because there was no observed signal below 320 amole, only the results for the first four targets are shown in FIG. 2). In the right column of Set A, aliquots of 0.32 μL of the six consecutive dilutions of the mutant target nucleic acid were spotted onto the membrane to generate a dot blot array of nucleic acid present in half log steps in the range of 1 pmole and 3 fmole. In the left column of Set B, aliquots of 0.32 μL of the six consecutive dilutions of the mutant target were spotted onto the membrane to generate a dot blot array of nucleic acid present in half log steps in the range of 10 fmole to 32 amole. In the right column of Set B, aliquots of 0.32 μL of the six consecutive dilutions of the wild type target nucleic acid were spotted onto the membrane to generate a dot blot array of nucleic acid present in half log steps in the range of 1 pmole and 3 fmole. Membranes were dried, and crosslinked as described in Experiment A.

Materials and methods were identical to Experiment A, except that the pre-hybridization incubation was extended to 90 minutes, and the third wash incubation was extended to 30 minutes. As noted above, the total volume of probe stock applied to each membrane was 200 μL, as compared with Example A wherein the total volume was 250 μL. The membranes of Set A were probed with wild type labeled PNA probe in the presence of unlabeled mutant PNA probe in the ratios indicated in FIG. 2. The membranes of Set B were probed with mutant labeled PNA probe in the presence of unlabeled wild type PNA probe in the ratios indicated in FIG. 2.

Results:

FIG. 2 is a composite of electronic images which were obtained by scanning the autoradiographic images (film). obtained as raw data from analysis of the membrane sets. The images have been arranged to align like target concentrations for easy comparison. For convenience the columns of the figure have been designated with the letters A–P and rows have been designated with the numbers 1–8. Many locations in the figure contain no data as there was either no data which was acquired for that set of conditions (i.e. rows 1–4 in columns A, C, E, G, I, K, M and O, and rows 7 and 8 in columns B, D, F, H, J, L, N, and P) or no detectable signal was observed at the particular concentration of nucleic acid target (100 amole and 32 amole).

The left half of the figure displays results for the membranes of Set A and the right half displays results for the membranes of Set B. For each membrane there is a column labeled "WT" for the wild type target, and "M" for the mutant DNA target. The two sets of membranes (A and B) are arranged from left to right as the relative molar concentration ratio of labeled (detectable) PNA probe to unlabeled PNA probe was increased from 1:0, 1:5, 1:100 and 1:500. For the wild type probe, the "WT" dilution series represents specific signal, and the "M" dilution series represents non-specific signal. For the mutant probe, the "M" dilution series represents specific signal, and the "WT" dilution series represents non-specific signal.

Signal from non-specific hybridization of the wild type or mutant labeled probe was greatly reduced in the presence of the unlabeled (blocker) probes. For example, with reference to FIG. 2, compare the signal intensity of the labeled wild type probe hybridized to the mutant target in the absence of blocker probe (column B) with that obtained from the hybridization in the presence of various amounts of unlabeled mutant (blocker) probe (columns D, F and H). In the absence of the unlabeled probe the non-specific signal was clearly evident at 32 fmole of target DNA (row 4, column B). Addition of 5 equivalents of unlabeled mutant probe reduced the intensity of the non-specific signal by approximately 3 fold, increasing the lowest detectable level of non-specific target to 100 fmole (row 3, column D). Addition of 100 equivalents of unlabeled mutant probe reduced the intensity of the non-specific signal by approximately 32 fold, increasing the lowest detectable level of non-specific target to 1 pmole (row 1, column f). Addition of 500 equivalents of unlabeled mutant probe reduced the intensity of the signal such that non-specific binding of the wild type probe to the mutant target was not detectable within the parameters of this experiment (row 1, column H).

The signal from the labeled mutant probe in the presence of wild type unlabeled (blocker) probes, and wild type targets was consistent with these results. For example, with reference to FIG. 2, compare the signal intensity of the labeled mutant probe hybridized to the wild type target in the absence of blocker probe (column J) with that obtained from the hybridization in the presence of various amounts of the unlabeled wild type (blocker) probe (columns L, N and P). In the absence of the unlabeled probe the non-specific signal was clearly evident at 10 fmole of target DNA (row 5, column J). Addition of 5 fold equivalents of unlabeled wild type probe reduced the intensity of the non-specific signal by approximately ~3 fold, increasing the lowest detectable level of non-specific target to 32 fmole (row 4, column L). Addition of 100 equivalents of unlabeled wild type probe reduces the intensity of the non-specific signal by approximately an additional 10 fold thereby increasing the lowest detectable level of non-specific target to 320 fmole (row 2, column N). Addition of 500 equivalents of unlabeled wild type probe reduced the intensity of the of the non-specific signal by approximately an additional 3 fold so that 1 pmole of wild type target is the lowest detectable level (row 1, column P). Consequently, the dynamic range (signal to noise ratio of the assay) for the reactions using the mutant probe has improved from 10 to 1 in the absence of unlabeled probe to approximately 1000 to 1 in the presence of 500 equivalents of unlabeled wild type probe.

As the ratio of unlabeled probe to labeled probe was increased there was a slight loss of specific signal. For example, with reference to FIG. 2, the lowest detectable level of wild type target was 320 amole (see row 8, columns A and C). In the presence of 100 fold equivalents of unlabeled mutant (blocker) probe, the limit of detection was reduced to 1 fmole (row 7, column E), This was a 3 fold loss of signal. In the presence of 500 fold equivalents of unlabeled probe (row 6, column G), there is approximately a 10 fold loss of signal. As discussed above, however, there was at least a 32 fold reduction in background associated with non-specific binding to non-target sequence. Consequently, there was at least a 10 fold improvement in the signal to noise ratio in the presence of 500 equivalents of unlabeled mutant probe. Similarly, the mutant target was at approximately 320 amole (see row 8, column K). The addition of 100 or 500 fold equivalents of unlabeled wild type probe, reduced the limit of detection to approximately 1 fmole (row 7 columns M and O). This was approximately a 3 fold loss in detectable signal. However, there was approximately a 100 fold reduction in background associated with non-specific binding to non-target sequence. Consequently, there was at least a 33 fold improvement in the signal to noise ratio in the presence of 500 equivalents of unlabeled wild type probe.

Summary:

In conclusion, the results illustrated in FIG. 2 further demonstrate that non-specific binding of labeled PNA probes to non-complementary nucleic acid sequences can be suppressed by the addition of unlabelled PNA probes which are complementary to non-target sequences to which the labeled PNA probes bind in a non-specific manner. The results demonstrate that point mutation discrimination improved from approximately 10 fold in the absence of the unlabeled probe to greater than 1000 fold in the presence of high levels of unlabeled (blocker) PNA probe. Moreover, there was very little loss of detectable signal (approximately 3 to 10 fold) even in the presence of 500 fold equivalents of unlabeled probe. Consequently, when employing the methods described herein, one can achieve several logs of improvement in point mutation discrimination and similar improvements in the dynamic range of the hybridization assay.

Example 5

Fluorescein Labeling of Peptide Nucleic Acids

Peptide Nucleic Acids (PNAs) were synthesized using commercially available chemicals and instrumentation from PerSeptive Biosystems, Inc. The N-terminus of the support bound oligomer was condensed with Fmoc-L-lys-(Fmoc)-OH (PerSeptive Biosystems, Inc. P/N GEN911094) using the automated synthesizer and standard PNA coupling conditions. Using the standard PNA protocols and condensation conditions, Fmoc-8-amino-3,6-dioxaoctanoic acid was condensed with each of the N-$\alpha$ and N-$\epsilon$ amino groups of the deprotected lysine amino acid to thereby branch the amino terminus of the PNA oligomer. The Fmoc groups of the support bound oligomer were then removed by treatment with piperidine in DMF. The resin was then treated with a solution containing 0.076 M 5(6)-carboxyfluorescein-NHS ester (Molecular Probes; P/N C-1311) 0.38 M diisopropylethylamine in DMF at room temperature for 30–60 minutes. The support was then washed to remove excess labeling reagent. The PNA was then cleaved from the support and purified using standard methodologies.

Example 6

Comparison of Blocking Probe Assays Using Combinations of Detectable Probes (PNA and Nucleic Acid) and Blocker Probes (PNA and Nucleic Acid)

Overview of Experiments A through C:

Experiments A–C were performed to compare combinations of PNA and nucleic acid probes as both detection and blocking probes in hybridization assays. The experiments were also performed to determine the optimal conditions for suppression of the binding of detectable probes to non-complementary nucleic acid sequences.

These experiments were directed to point mutation analysis because point mutations are some of the most difficult of all nucleic acid modifications to detect using a probe based hybridization assay. A known point mutation in the codon twelve region of the human Ki-ras gene is commonly observed in malignant tissues and immortalized cell lines. This was chosen as a model system. Two biotinylated 31-mer DNA targets having the subsequence of the mutant and wild type codon twelve regions of human Ki-ras were synthesized. These targets differed by one base pair (a base pair mismatch or point mutation) which occurs in the middle of each oligomer at position 16 (See below: Probes and Nucleic Acid Targets). PNA and DNA probes which were complementary to each of the two target nucleic acid sequences were also synthesized. The probes were prepared as both labeled with fluorescein (detectable probes) and unlabeled (blocker probes).

A set of labeled and unlabeled PNA 15-mers was prepared since PNAs of this length have demonstrated high specific binding to nucleic acid sequences with the appropriate affinity and stability. For comparison, a set of labeled and unlabeled DNA 15-mers was prepared. Additionally, a set of labeled and unlabeled DNA 25-mers was also prepared. The longer 25-mer DNAs were believed to be more suitable for comparison to the 15-mer PNAs because they have a thermal stability (Tm) which was more closely comparable with the PNA 15-mers.

In experiments not described herein, blocker probes were added at various concentrations either before, during or after the addition of labeled (detectable) probes. The results demonstrated that incubation of the blocker probe and target nucleic acid prior to addition of the labeled (detectable) probe resulted in the most favorable signal to noise ratio.

Experiment A

Signal from labeled probes hybridized to complementary or non-complementary targets over a range of blocker probe concentrations under conditions optimized for the hybridization of each probe type (PNA or DNA) was measured. The relative ability of unlabeled PNA and DNA probes to serve as blocker probes was compared.

Experiment B

The sensitivity and specificity of the DNA and PNA probe sets at various target levels in the presence and absence of blocking probes was compared.

Experiment C

PNA and DNA blocker probes were used in conjunction with labeled DNA probes in normal and accelerated hybridization assays.

Materials and Methods:

The PNA and DNA probes and targets used are shown below.

Biotinylated DNA Targets

```
Wild type  5'   Biotin-GTGGTAGTTGGAGCTGGTGGCGTAGGCAAGA-OH   3'   SEQ ID NO: 3
Mutant     5'   Biotin-GTGGTAGTTGGAGCTTGTGGCGTAGGCAAGA-OH   3'   SEQ ID NO: 4

PNA Labeled Probes

Wild type  N     (Flu-linker)2-K-ACGCCACCAGCTCCA-NH2        C
Mutant     N     (Flu-linker)2-K-ACGCCACAAGCTCCA-NH2        C PNA Blocker probes Wild type  N              H-ACGCCACCAGCTCCA-NH2              C
Mutant     N              H-ACGCCACAAGCTCCA-NH2              C DNA Labeled Probes Wild type-15  5'      Flu-spacer-ACGCCACCAGCTCCA-OH         3'   SEQ ID NO: 5
Mutant-15     5'      Flu-spacer-ACGCCACAAGCTCCA-OH         3'   SEQ ID NO: 6
Wild type-25  5'Flu-spacer-TGCCTACGCCACCAGCTCCAACTAC-OH     3'   SEQ ID NO: 7
Mutant-25     5'Flu-spacer-TGCCTACGCCACAAGCTCCAACTAC-OH     3'   SEQ ID NO: 8

DNA Blocker probes

Wild type-15  5'           HO-ACGCCACCAGCTCCA-OH            3'   SEQ ID NO: 9
Mutant-15     5'           HO-ACGCCACAAGCTCCA-OH            3'   SEQ ID NO: 10
Wild type-25  5        HO-TGCCTACGCCACCAGCTCCAACTAC-OH      3'   SEQ ID NO: 11
Mutant-25     5        HO-TGCCTACGCCACAAGCTCCAACTAC-OH      3'   SEQ ID NO: 12
```

All DNA probes are illustrated from 5' to 3' and all PNA probes are illustrated from the amino terminus (N) to the carboxyl terminus (C). Probe and target mismatch sites are underlined and lie at the centers of the molecules. Probe names indicate the sequence to which the probe is complementary. For example, the "wild type PNA" probe is a perfect match to the wild type DNA target when hybridized in the antiparallel orientation. Nucleic acid probes were either obtained from commercial vendors of custom oligonucleotides, or synthesized using commercially available instrumentation and reagents. For the fluorescein labeled DNA probes, "spacer" designates a linker incorporated into the oligonucleotide with the Fluorodite™ labeling phosphoramidite obtained from PerSeptive Biosystems, Inc. (P/N GEN080110). The biotin labeled DNA targets were prepared by a commercial vendor of custom oligonucleotides (Genosys) using their standard procedures. PNA probes were synthesized using commercially available instrumentation and reagents. PNAs were branched at the N-terminus by the condensation of a lysine amino acid (illustrated as "K") during chemical synthesis. PNAs were labeled with fluorescein as described in Example 5 of this specification. For the PNA oligomers, "linker" designates the Expedite PNA linker (P/N GEN063032) attached to the lysine amino acid at the N-terminus of the PNA oligomer.

General Assay Procedure:

Biotinylated target nucleic acids and probes were incubated under appropriate hybridization conditions, after which the contents of the hybridization reaction were placed in wells of Streptavidin coated microtitre plates to thereby capture the biotinylated target nucleic acids and any probes hybridized thereto. After removal of the unbound material and subsequent washing, the wells were contacted with an alkaline phosphates conjugated to a anti-FITC Fab fragment "Rabbit(Fab) anti-FITC/AP" The Rabbit(Fab) anti-FITC/AP binds to the fluorescein of the detectable probe, if present (note, although the PNA probes in this assay were bis-labeled with fluorescein, prior studies demonstrated that detection of these probes with the Rabbit(Fab) anti-FITC/AP conjugate produced similar levels of signal as single-labeled PNA or DNA probes). Non-specifically bound α-fluorescein antibody-alkaline phosphatase enzyme conjugate was then removed by washing, and an alkaline phosphatase activated chemiluminescent substrate was then added to the wells. Emitted light was measured using a suitable plate reader.

Figure 3:
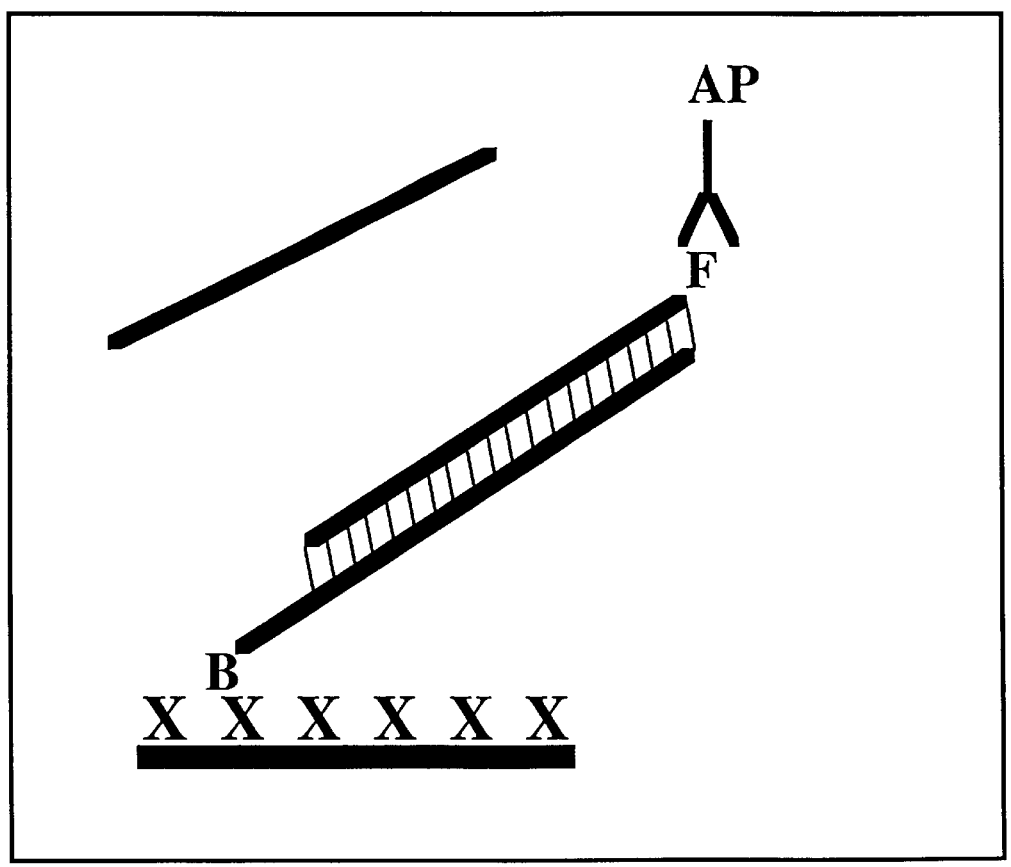
FIG. 3 is a Molecular Diagram of hybridization assay components.

The Molecular Diagram (FIG. 3) illustrates the components of the hybridization assay as described above. The Streptavidin coated plate, illustrated by the symbol "X————", binds the biotinylated nucleic acid target illustrated using the symbol "B————". Fluorescein labeled probe which is hybridized to the target nucleic acid is illustrated by the symbol "————F". The fluorescein moiety "F", is used as a hapten to thereby bind an α-fluorescein antibody which is illustrated as the upside down "Y" in the figure. The α-fluorescein antibody is conjugated to the alkaline phosphatase enzyme which is illustrated as "AP" in the figure. The α-fluorescein antibody-alkaline phosphatase enzyme conjugate "Rabbit(Fab) anti-FITC/AP" is commercially available from DAKO A/S (Copenhagen, Denmark). Non-labeled blocker probe is shown as not binding to any assay component, it is illustrated by the symbol "————".

Hybridizations were performed in polystyrene microtiter plates by mixing stock solutions of probes, nucleic acid targets, and hybridization buffers. All incubations were performed at room temperature with agitation. Each assay was performed by first adding the required amount of target nucleic acid, diluted to 80 μL volume in buffer to the polystyrene microtitre plate. For reactions containing unlabeled (blocker) probes, a solution containing the appropriate amount of unlabeled (blocker) probe, in a 10 μL volume, was then added to the target nucleic acid and the mixture was incubated at ambient temperature (22±2° C. for all experiments). For control reactions which contained no unlabeled (blocker) probe, a 10 μL aliquot of the appropriate dilution buffer was added. A solution containing the appropriate amount of labeled (detectable) probe, in 10 μL volume, was then added to the target/blocker probe mixture and this solution was again incubated at ambient temperature. Each 100 μL reaction was transferred to a well of a Streptavidin coated microtitre plate and allowed to incubate for 30 minutes. The solution in the well was then removed, and each well was washed six times with 300 μL of Wash Buffer A. Next, 100 μL of a 1:1000 dilution of Rabbit(Fab) anti-FITC/AP stock solution in Wash Buffer B was added, and allowed to incubate for 30 minutes at ambient temperature (the optimal antibody dilution factor, 1:1000, was determined experimentally, data not shown). The Anti-FITC-AP solution was then removed and the wells were washed three times with 150 μL of Wash Buffer B, then three times with 150 μL of Wash Buffer C. Between washes, the plates were incubated at ambient temperature with shaking for 1 minute. Finally, 50 μL of Visualization Reagent was added to each well and the plate was incubated at ambient temperature with shaking for exactly 4 minutes. The Visualization Reagent was transferred to an opaque (white) reading plate and read for 1 sec in a Wallac 1420 Multilabel luminometer. The readings obtained from the luminometer in relative light units (RLU) indicated the extent of binding of the labeled (detectable) probe to the target nucleic acid. For experiments A–C, each hybridization reaction was performed at least in triplicate and the resulting measurements were averaged. No data points were discarded. Background measurements were performed at least in duplicate and were also averaged.

The time required for each step of the assay is shown below.

Assay Time Line:

| Steps: | Time Line | |
|---|---|---|
| 1. | 1 hour blocker probe hybridization | 1.00 hr |
| 2. | 1 hour labeled probe hybridization | 2.00 hr |
| 3. | 30 minute capture of complexes onto SA coated plate | 2.50 hr |
| 4. | 6x Wash Buffer A washes | 2.60 hr |
| 5. | 30 minute Anti-FITC-AP binding | 3.10 hr |
| 6. | 3x Wash Buffer B Washes | 3.15 hr |
| 7. | 3x Wash Buffer C Washes | 3.20 hr |
| 8. | 4 minute Visualization Reagent incubation | 3.30 hr |

Reagent and Buffer Compositions:
Wash Buffer A
10 mM NaCl
5 mM TRIS pH 7.3
0.01% TWEEN-20
Wash Buffer B
0.5 M NaCl
50 mM TRIS pH 9.0
Wash Buffer C
10 mM TRIS pH 9.4
10 mM NaCl
1 mM $MgCl_2$
Visualization Reagent
0.4 mM CDP-Star™
1× Sapphire II Enhancer™
0.1 M Diethanolamine The Visualization Reagent comprises CDP-Star™ (Tropix, Bedford, Mass.), a 1,2-dioxetane, dioxetane, which when dephosphorylated by AP produces a metastable intermediate, which emits light at 466 nm upon decay (half life ~2 min.). Sapphire II™ (Tropix, Bedford, Mass.) is a luminescence enhancer which reduces the effects of aqueous quenching, producing amplified signals Choice of Hybridization Conditions:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known techniques of fixing several of the aforementioned stringency factors and then determining the effect of varying a single stringency factor. This was done for the various probes types and lengths. For the work presented here, the hybridization conditions for a probe set were defined as optimal when a further increase in stringency produced large reduction in signal without a corresponding increase in the ability to discriminate between perfectly matched and mismatched targets.

A number of stringency factors were fixed throughout the experiments for either probe type (PNA or DNA) including pH (7.0), temperature (ambient), detergent (0.5% v/v, Tween-20) and chaotrope (none). Ionic strength was fixed at 100 mM NaCl for hybridizations with PNA detector probes and 250 mM NaCl for hybridizations involving DNA detector probes. With these stringency factors fixed, formamide concentration was varied and found to be optimal at 70%, 65% and 35% for the PNA 15-mer, DNA 25-mer and DNA 15-mer probes, respectively. A summary of buffers which were found to provide optimal stringency is shown below.

Hybridization Buffer Table:

| Buffer | Probe Type | Formamide | NaCl (mM) | TWEEN-20 | $Na_2PO_4$ |
|---|---|---|---|---|---|
| A: | PNA | 70% | 100 | 0.5% | 10 mM |
| B: | DNA 25 | 65% | 250 | 0.5% | 10 mM |
| C: | DNA 15 | 35% | 250 | 0.5% | 10 mM |

All hybridizations were performed at room temperature when using the conditions described above.

Experiment A

Assay Description:

FIG. 4A is a plate assay schematic of the configuration of hybridization reactions performed in the wells of a microtiter plate for this experiment. Each of the reaction wells in the figure is given a specific location comprised of an alphanumeric character (e.g. A) and a number (e.g. 1). For row locations the alphanumeric character is sequentially incremented and for column locations the number is sequentially incremented. For each condition tested, three data points (arranged column wise) were generated to obtain an average. Dilutions of targets, labeled (detectable) probes and unlabeled (blocker) probes were prepared as described above. Complementary, "Match", target sequence was added at 30 fmole to rows A–C; non-complementary, "Mismatch", target sequence was added at 300 fmole to the wells in rows D–F, "No Target", control hybridizations were performed in the wells in rows G and H. Labeled detector probes were used at 3 pmole/well. The ratio of unlabeled (blocker) probe to labeled (detectable) probe is indicated at the top of each column of FIG. 4A. Labeled wild type probes (and mutant unlabeled (blocker) probes) were used in the wells in columns 1–6; labeled mutant probes (and wild type unlabeled (blocker) probes) were used in the wells in columns 7–12.

The experimental conditions, assay timing and reagent composition were described in the Materials and Methods section, above. The assay was performed three times, once with PNA probes, once with DNA 25-mer probes, and once with DNA 15-mer probes. Wild type and mutant PNA 15-mer, DNA 15-mer and DNA 25-mer labeled (detectable) probes were hybridized under conditions optimized for each probe type (See: Choice of Hybridization Conditions, above).

Figure 4B:
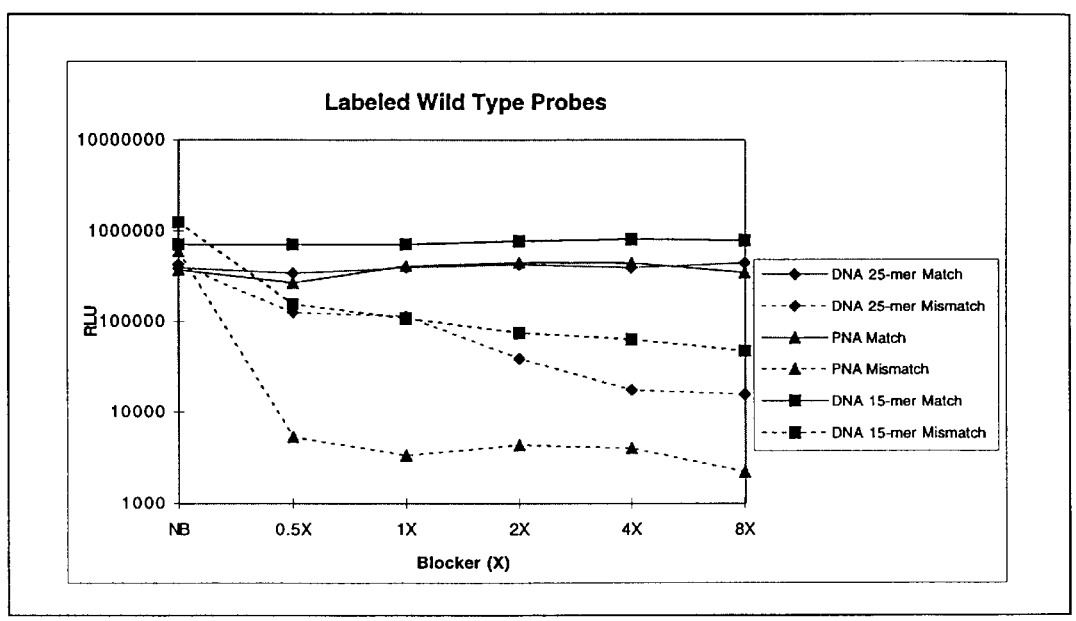
FIG. 4B is a graphical illustration of hybridization assay data.
Figure 4C:
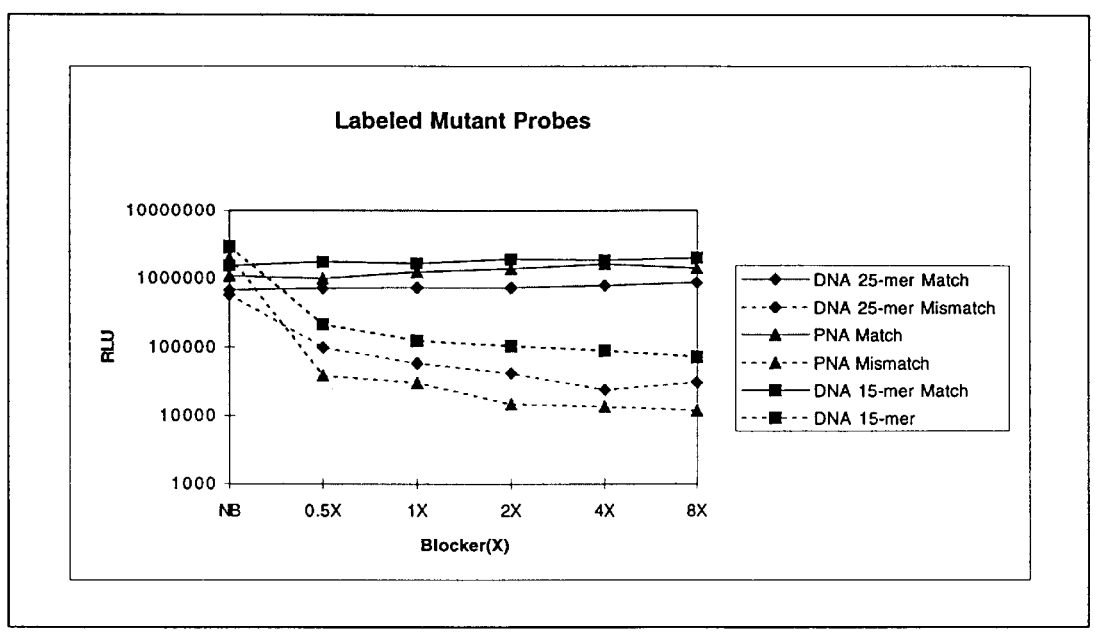
FIG. 4C is a graphical illustration of hybridization assay data.

Results and Discussion:

With reference to FIGS. 4B and 4C, the data displayed are average RLU (with average backgrounds subtracted) on the ordinate axis, vs. the relative amount of unlabeled (blocker) probe ("Blocker(X)") along the abscissas. The ordinate axes of FIGS. 4B and 4C are on the $LOG_{10}$ scale. FIG. 4B displays the data for the labeled (detectable) wild type probes in the presence of various amounts of unlabeled mutant (blocker) probe. FIG. 4C displays the data for the labeled (detectable) mutant probes in the presence of various amounts of unlabeled wild type (blocker) probe. In both Figures, the solid lines indicate data generated by hybridization between complementary targets and probes ("Match") and the dashed lines indicate data generated by hybridization between non-complementary targets and probes ("Mismatch"). In both Figures, diamond shaped symbols indicate use of DNA 25-mer probes, triangle shaped symbols indicate use of PNA probes, and square shaped symbols indicate use of DNA 15-mer probes. The use of unlabeled (blocker) probes in conjunction with labeled DNA or labeled PNA probes suppressed signal from non-complementary targets (dashed lines). Addition of unlabeled (blocker) probes to complementary target did not prevent binding (hybridization) of the complementary probe and target as was indicated by the constant signal levels maintained (solid lines). Of the three probe sets tested, the PNA probes provided the greatest level of discrimination between complementary and non-complementary sets of probes and targets as indicated by the greatest absolute difference between the solid and dashed line for each set of probes. These conclusions are further supported by the data presented in FIG. 4D.

FIG. 4D is a table of Match/Mismatch (Ma/Mi) ratios. Column A displays the relative amount of blocker probe present in each hybridization reaction. Columns B–G display the calculated Ma/Mi ratio for each probe (defined in row 2) at each relative concentration of unlabeled (blocker) probe. Match refers to signal from hybridization between perfectly complementary target nucleic acids and probe sequences, whereas; Mismatch refers to signal from hybridization between non-complementary target nucleic acids and probe sequences which are related as point mutations. The MajMi ratio gives a sense of the relative affinity of a probe for its matching target as compared to a one base pair mismatch target (i.e., point mutant). The ratios were generated by application of the following formula where "avg. bkgd" is the average background signal.

(avg. Match signal–avg. bkgd.)/((avg. Mismatch signal–avg. bkgd.)/10)=$Ma/Mi$ ratio.

The "Mismatch" term (denominator) is divided by 10 to normalize the different levels of target (30 and 300 fmole) being detected in "Match" and "Mismatch" samples. Background was calculated by averaging all of the "No Target" values for each probe tested (wells G1–H6 in FIG. 4A). As an example, the value of 9 for the wild type PNA probe Ma/Mi ratio (FIG. 4D, column B, row 3) was derived by applying the equation to the average of the signals generated in wells A1–C1 (Match), and D1–F1 (Mismatch)..

The data in FIG. 4D reveals a dramatic increase in the Ma/Mi ratio upon addition of increasing amounts of unlabeled (blocker) probe for the two probe types, PNA and DNA (See: rows 3–8 of each column). In the case of the DNA probe sets (See: columns B, C, F and G) the Ma/Mi ratios go up almost to 300. For the PNA probe sets (See: columns D and E) the ratios go well above 1000. The four DNA probe sets all demonstrate approximately equal Ma/Mi ratios. For example, at "2×" (row 6) the wild type DNA 25, mutant DNA 25, wild type DNA 15, and mutant DNA 15 are 110, 173, 105, and 185 respectively. The PNA probes display a greater increase in discrimination than the DNA probes as the concentration of unlabeled (blocker) probe was increased. At "2×" blocker (row 6), the wild type PNA and mutant PNA have Ma/Mi ratios of 1009 and 929, respectively. There is also a substantial difference in Ma/Mi ratios for the PNA probes present at only 0.5× blocker (row 4). The PNA probes are at 497 and 255, while the DNA probes have values of only 27, 73, 46, and 83. This observed difference is probably attributable to the fast rate of hybridization of PNA probes, and the relative stability difference between perfect match and one base pair mismatch PNA/DNA hybrids as compared to DNA/DNA hybrids.

Summary of Experiment A:

The data demonstrates that unlabeled PNA and DNA probes can be effectively used to suppress the binding of detectable probe to non-target sequence over a wide range of concentrations. At all concentrations tested, the unlabeled (blocker) PNA probes are better at enhancing discrimination between complementary and non-complementary targets than either of the unlabeled (blocker) DNA probes tested (i.e. 15-mer or 25-mer).

Experiment B

Assay Description:

In this experiment, wild type and mutant PNA 15-mer, DNA-15-mer and DNA 25-mer labeled (detectable) probes were hybridized to varying amounts of complementary and non-complementary nucleic acid targets. Results were obtained both in the presence and absence of two fold equivalents of unlabeled blocker probes.

FIG. 5A is a plate assay schematic of the configuration of hybridization reactions performed in the wells of a microtiter plate for this experiment. The well positions are again assigned a two digit code comprising an alphanumeric character (e.g. A) and a numeric character (e.g. 1) to designate column and row assignments, respectively. For each condition tested, four data points (arranged column wise) were generated to obtain an average (derived data) useful for comparative analysis. The top half of the plate (rows 1–4) was used to measure signal from labeled wild type sequence probes. The bottom half of the plate was used to measure signal from labeled mutant sequence probes.

Dilutions of target nucleic acids, labeled (detectable) probes and unlabeled (blocker) probes were performed as described above. For this experiment, "Match" targets were used in quantities of 50, 5, and 0.5 femtomoles (fmole) per well (columns 1–6). "Mismatch" targets were used at high levels, 500 and 50 fmoles per well (columns 9–12), due to the expected decrease in binding affinity between non-complementary target and probe. Control reactions containing no target "NT" were also performed in the wells in columns 7 and 8. The presence and absence of unlabeled (blocking) probe is indicated by the (−) or (+), respectively, above the columns. In this experiment, the wells in the odd numbered columns (1, 3, 5 etc.) were used to measure signal in the absence of unlabeled (blocker) probes, and the wells in the even numbered columns (2, 4, 6 etc.) were used to measure the signal in the presence of blocker probes. Background for the wild type sequence probes in the absence of unlabeled (blocker) probe was measured in wells A7–D7, and background for the mutant sequence probes in the absence of blocker probe was measured in wells E7–H7. The concentration of labeled (detectable) probe in each well was 5 pmole/100 μL, the unlabeled (blocker) probe was present at 10 pmole/100 μL, and the target nucleic acids were present at the concentrations depicted in the figure. The assay was performed three times, once with PNA probes, once with DNA 25-mer probes, and once with DNA 15-mer probes, each time under conditions which were optimized for the particular probe type.

Results and Discussion:

With reference to FIG. 5B, the Ma/Mi ratios for 50 fmole of target nucleic acid are shown for all three probe types, in the absence and presence of blocker probes. The Ma/Mi ratio is calculated the same way as in Experiment A except that the denominator is not divided by 10 because match and mismatch values were derived from equal amounts of target (50 fmol). Column B displays Ma/Mi ratios in the absence of blocker probe. Column C displays Ma/Mi ratios in the presence of two equivalents of unlabeled (blocker) probe. For example, the Ma/Mi ratio for the labeled PNA probe in the absence of blocker can be found in FIG. 5B column B, row 2 (Ma/Mi=2.5). In this example, the values for "Match signal", "avg. bkgd", and "Mismatch signal" from the above equation are derived from FIG. 5A, wells A1–D1, A7–D7, and A11–D11, respectively.

With reference to FIG. 5B, column B, all Ma/Mi ratios are between 1.1 and 4.1 in the absence of unlabeled (blocker) probe (whether DNA or PNA). A low value for the Ma/Mi ratio indicates comparatively poor discrimination between the match and mismatch targets. Because all values are less than ten in the absence of unlabeled (blocking) probes these conditions are not be very useful for point mutation analysis. With reference to column C of FIG. 5B, there was a dramatic increase in the Ma/Mi ratio for all experiments where blocker probe was used (compare results with column B). For the wild type probes, the PNA probe set had more than twice the power to discriminate between target and non-target nucleic acid as compared with the DNA probe sets (PNA 15-mers, 78; DNA 25-mers, 30; DNA 15-mers, 30). Likewise, for the mutant probes, the PNA probe set had more than twice the power to discriminate between target and non-target nucleic acid as compared with the DNA probe sets (PNA 15-mers, 140; DNA 25-mers, 42; DNA 15-mers, 65).

Figure 5C:
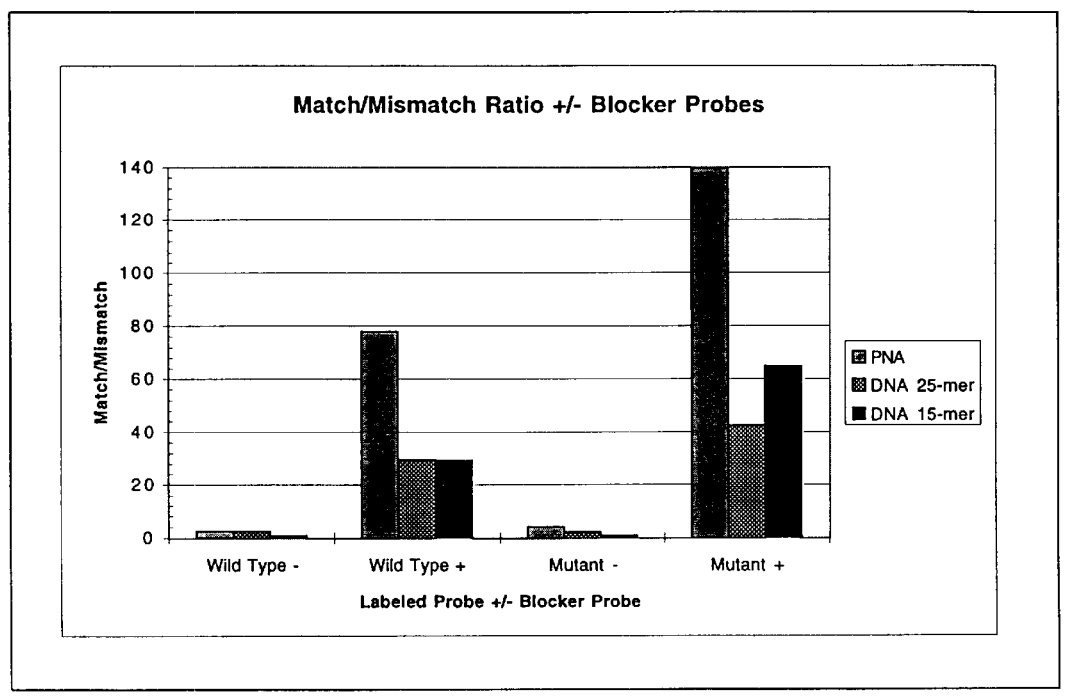
FIG. 5C is a graphical illustration of hybridization assay data.

FIG. 5C is a graphical illustration of the data from FIG. 5B. Note the ordinate axis is on a linear scale. The graphical illustration is useful as a quick means to visually analyze and compare the tabular data.

FIG. 5D shows the "Blocker Effect" (BE) values for all three probe types at all target amounts tested. The BE value is determined using the following equation.

(avg. signal w/o blocker−avg. bkgd.)/(avg. signal w/blocker−avg. bkgd.)=$BE$

The BE value measures a fold decrease in signal resulting from the addition of unlabeled (blocker) probe to a hybridization reaction. It follows from the equation, that the BE value for an ideal blocker probe would be approximately equal to 1.0 when the blocker was added to a hybridization reaction involving a detectable probe and its matched target (i.e., the blocker probe would not depress the signal). In the case of a hybridization between a labeled probe and a mismatched target, an ideal blocker probe would have a large BE value (i.e., the blocker would suppress binding of the detectable probe to the mismatch target). The calculation of a BE value is illustrated by the following example. For the wild type PNA probe at 5 fmole of wild type (Match) target nucleic acid the BE value equals 1.0 (FIG. 5D, column C, row 2). This value was calculated by using "avg. signal w/o blocker", "avg. bkgd", and "avg. signal+blocker" values derived (as averages) from wells A3–D3, A7–D7, and A4–D4 respectively (in FIG. 5A).

With reference to FIG. 5D, columns B, C, V), there is no appreciable loss of signal ($0.5 \leq BE \leq 1.5$) seen at any target level, with either the DNA or PNA probes where the labeled probes and target nucleic acids are perfect complements (i.e., match). However for mismatch targets at both the 500 and 50 fmole levels (See: columns E and F), the BE values were substantially greater especially for the PNA probes. For example, at 500 fmole of target (see column E) the wild type and mutant PNA probes have BE values of 132 and 86, respectively. The wild-type DNA 25-mers and DNA 15-mers have BE values of 11 and 17, respectively. The mutant DNA 25-mers and DNA 15-mers have BE values of and 16 and 23, respectively. This data demonstrates that the use of unlabeled (blocker) PNA probe, when used with labeled (detectable) PNA probe, results in a much higher level of discrimination between complementary and non-complementary target nucleic acid than does the use of either set of unlabeled (blocker) DNA probes in conjunction with labeled (detectable) DNA probes.

Although the data in column F generally exhibit the same trends as the data in column E, the values are consistently lower in column F. It is believed that this discrepancy is attributable to the significantly lower signal at 50 fmole, thereby resulting in lower signal to noise ratios. Therefore, the data in column E is believed to be better quantitative data.

Figure 5E:
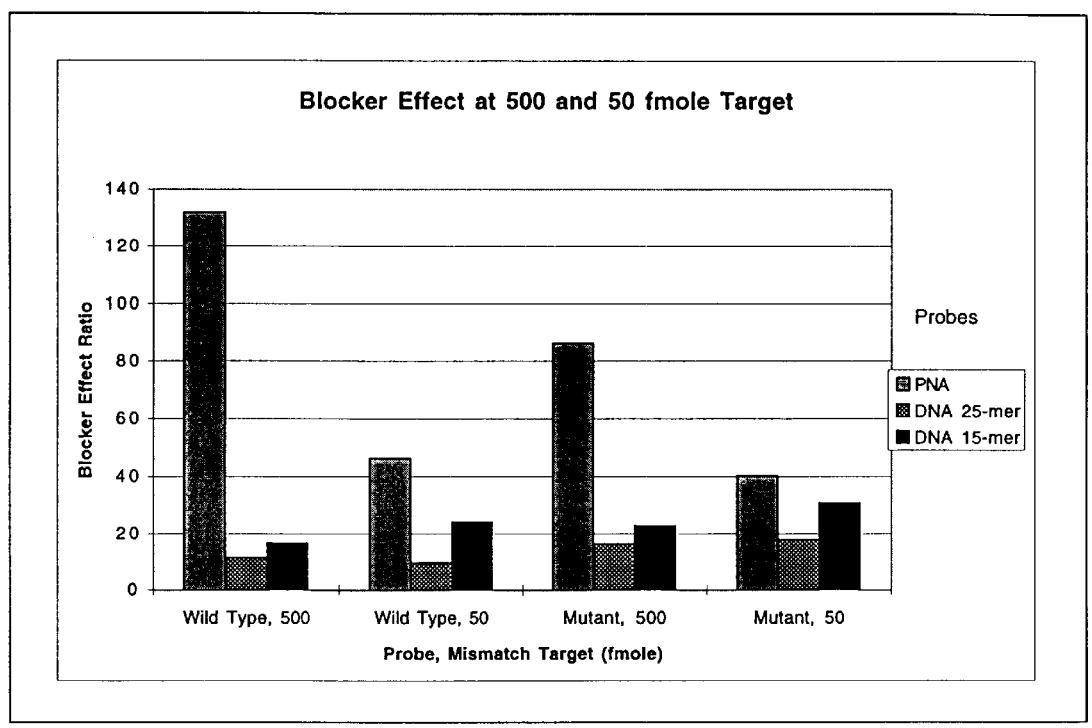
FIG. 5E is a graphical illustration of hybridization assay data.

The BE values at 500 and 50 fmole which are listed in FIG. 5D are graphically illustrated in FIG. 5E. Note the ordinate axis is on the linear scale. The graphical illustration is useful as a quick means to visually analyze and compare the tabular data.

Summary of Experiment B:

The use of unlabeled (blocker) probes significantly increased the discrimination of point mutations in target nucleic acids. The improved discrimination was obtained without any significant loss of signal when using both labeled DNA or PNA probes, at any target level tested. However, the use of unlabeled (blocker) PNA probes produced a substantially greater increase in point mutation discrimination than the use of unlabeled (blocker) DNA probes.

Experiment C

Assay Description:

Experiment C was performed to determine whether the various probe types could be intermixed (e.g., labeled (detectable) DNA used with unlabeled (blocker) PNA probes) and if so, how did the results compare with the all PNA or DNA probe sets. To this end, unlabeled (blocker) PNA 15-mer probes were used as blockers for labeled (detectable) DNA 25-mer probes under conditions optimized for the hybridization of the DNA 25-mers to their targets (Hybridization Buffer B).

Hybridization times were also varied to determine whether there was any benefit to performing the hybridization assay more rapidly. For this comparison, hybridization time for incubations with the unlabeled (blocker) probe and labeled (detectable) probe were shortened from 60 to 20 minutes.

FIG. 6A is a schematic of the plate set up used in Experiment C. The well positions are again assigned a two digit code comprising an alphanumeric character (e.g. A) and a numeric character (e.g. 1) to designate column and row assignments, respectively. Hybridization reactions were performed in the wells in rows A–C for 60 minutes. Hybridization reactions were performed in the wells in rows D–H for 20 minutes. For comparison, 20 min. hybridization reactions were also performed using labeled (detectable) PNA probes with and without unlabeled (blocker) PNA probes in Hybridization Buffer A (100 mM NaCl and 70 percent formamide) (See FIG. 6A, rows G and H) which is optimized for the all PNA system.

Only the labeled wild type probes, and their corresponding unlabeled (blocker) mutant probes were used in this experiment. Hybridization reactions containing the wild type DNA 25-mer probes were performed in the wells in rows A–F. Hybridization reactions containing the wild type PNA 15-mer probes were performed in the wells in rows G and H. The unlabeled (blocker) DNA 25-mer probe (mutant sequence) was used in the hybridization reactions performed in the wells in rows A and D. Unlabeled (blocker) PNA probe (mutant sequence) was used in the hybridization reactions performed in the wells in rows B, E and G. Control reactions containing no unlabeled (blocker) probes were performed in rows C, F and H. Reactions performed in columns 1–3 contained 500 fmole of mutant (non-complementary) target. Reactions performed in the wells in columns 4–6 contained 50 fmole of mutant target. Control reactions performed in the wells in columns 7–9 contained no target, and reactions performed in the wells in columns 10–12 contained 50 fmole of wild type (complementary) target. Data was collected from three identical hybridization reactions and averaged to generate the derived data.

Results and Discussion:

With reference to FIG. 6B, the table displays derived Ma/Mi ratios for 50 fmole of target nucleic acid for both probe types in the presence of unlabeled (blocker) probes. The Ma/Mi and blocker effect ratios are generated with the same formulas used in Experiment A, except that the denominator was not divided by 10 since the match and mismatch target amounts were equal (50 fmol). For example, use of the labeled and unlabeled DNA 25-mer probes and 60 minute hybridization times gave a Ma/Mi value of 125 (FIG. 6B, column D, row 2). In this example, the terms "Match signal", "avg. bkgd", and "Mismatch signal" from the above equation are derived from wells A10–A12, A7–A9, and A4–A6, respectively (FIG. 6A).

With reference to FIG. 6B, rows 2–4, the presence of unlabeled (blocker) DNA probe (row 2) and unlabeled (blocker) PNA probe (row 3) exhibited significant beneficial effects on the Ma/Mi ratio as compared with hybridizations in which no blocker probes were present (row 4). When using the conditions optimized for the DNA 25-mers with 60 minute hybridizations, the results obtained with the unlabeled (blocker) DNA blocker were somewhat better than the results obtained with the unlabeled (blocker) PNA probes (compare rows 2 and 3).

By comparison however, data obtained for the 20 minute hybridizations demonstrate that, under these conditions, the unlabeled (blocker) PNA had a higher Ma/Mi ratio than did the unlabeled (blocker) DNA probe (compare rows 5 and 6 respectively). Moreover, the point mutation discrimination was greatly improved in the presence of unlabeled (blocker) probes (PNA or DNA) (compare rows 5 and 6 with row 7). With reference to column D, rows 8 and 9, the presence of the unlabeled (blocker) PNA probes, under conditions optimized for PNA hybridizations, resulted in the highest specificity when used in combination with the labeled (detectable) PNA probe (Ma/Mi ratio=357). This data demonstrates that the rapid hybridization assay format when performed in combination with unlabeled and labeled PNA probes results in the most dramatic point mutation discrimination.

With reference to FIG. 6C, the BE values calculated from the derived data are presented. The BE value was calculated as described in Experiment B. In all mismatch cases the BE value was larger when using the unlabeled (blocker) PNA probes than when using the unlabeled (blocker) DNA 25-mer probes (compare row 3 to row 2, and row 5 to row 4). Concomitant with the marked increase in discrimination through the use of PNA blocker probe, there was a slight cost to signal ($1.2 \leq BE \leq 1.6$) (see column D, rows 3, 5, and 6). The BE values for the unlabeled (blocker) DNA probes are similar to those observed in Experiment B. As observed in Experiment B, there was no loss of signal associated with the presence of the unlabeled (blocker) DNA probes (see column D; rows 2, 4). With regard to columns E and F, a comparison of data in rows 1–5 with the data in row 6 demonstrated that although unlabeled (blocker) PNA probes can increase the discrimination of the labeled DNA 25-mer probes, the presence of unlabeled (blocker) PNA probes in conjunction with labeled PNA probes was far better at suppressing signal from mismatch targets.

Summary of Experiment C:

Unlabeled (blocker) PNA probes can be used to improve discrimination of labeled (detectable) DNA probes with little loss of sensitivity. However, the presence of unlabeled (blocker) PNA probes increases the level of point mutation discrimination of labeled (detectable) DNA probes to a greater extent than the most nearly equivalent unlabeled (blocker) DNA probes. Rapid hybridization assay formats are preferred when using the unlabeled (blocker) PNA probes, particularly when the conditions have been optimized for hybridization of labeled (detectable ) nucleic acid probes.

Example 7

Synthesis of PNA Capture Probe Comprising a C-Terminal Arylamine moiety

Experiment A: Synthesis of N-α-(Fmoc)-N-ε-(4-(N-(tert-butyloxycarbonyl)-aminobenzoyl)-L-Lysine-OH To 2.6 mmole of N-α-Fmoc-L-lysine-OH was added 2.7 mmole of trifluoroacetic acid to dissolve the amino acid. Once the amino acid was completely dissolved this solution was added to the activated 4-(N-(tert-butyloxycarbonyl)-aminobenzoic acid prepared as described below.

To 2.6 mmole of 4-(N-(tert-butyloxycarbonyl)-aminobenzoic acid (prepared in Example 1) was added 50 mL of N,N'-dimethylformamide (DMF), 2.7 mmole [O-(7-azabenzotriaol-1-yl)-1,1,3,3-tetramethyl uronium hexafluorophosphate (HATU) and 15 mmole diisopropylethylamine (DIEA). This solution was allowed to stir for 20 minutes and then the solution of N-α-Fmoc-L-lysine-OH was added dropwise. After reacting for 30 min., the solvent was removed by evaporation under reduced pressure. The residue was partitioned in 100 mL of dichloromethane (DCM) and 50 mL of 10% aqueous citric acid. An attempt was made to wash the organic layer with 50 mL of 5% aqueous sodium bicarbonate but the product crystallized from the solution. The white solid was then collected by vacuum filtration. An attempt was made to dissolve the solid in a mixture of 30 mL of 10% aqueous citric acid and 70 mL DCM but the product would not dissolve. Thus, the solid was again collected by vacuum filtration and used as obtained. Yield 0.924 g (1.57 mmole: 60%).

Experiment B: Synthesis of N-α-(Fmoc)-N-ε-(4-(N-(tert-butyloxycarbonyl)-aminobenzoyl)-L-Lysine-PAL-Peg/PS Synthesis Support The N-α-(Fmoc)-N-ε-(4-(N-(tert-butyloxycarbonyl)-aminobenzoyl)-L-Lysine-OH prepared as described above was used to prepare a synthesis support useful for the preparation of C-terminal arylamine modified PNA probes. The Fmoc group of commercially available bulk Fmoc-PAL-Peg-PS (PerSeptive Biosystems, Inc.) synthesis support (approx. 1 g) was removed by treatment, in a flow through vessel with 20% piperidine in DCM for 25 minutes. The deblocking solution was then removed from the reaction vessel and the resin was washed with DMF and dried with a flushing stream of argon.

A solution containing 0.440 g N-α-(Fmoc)-N-ε-(4-(N-(tert-butyloxycarbonyl)-aminobenzoyl)-L-Lysine-OH, 4.8 mL of DMF, 0.266 g HATU, 0.157 mL DIEA and 0.104 mL 2,6-lutidine was prepared by sequential addition of the reagents listed. This solution was added to the washed resin and allowed to react for 2.5 hours. The solution was then flushed through the vessel with a stream of argon and the resin washed sequentially with DMF, DCM and DMF. The resin was then dried with a flushing stream of argon.

The resin was then treated with 5 mL of standard commercially available PNA capping reagent (acetic anhydride and 2,6-lutidine in DMF) for three minutes. The capping reagent was then flushed from the vessel and the resin was washed with DMF and DCM. The resin was then dried with a stream of argon. Finally, the resin was dried under high vacuum.

Final loading of the resin was determined by analysis of Fmoc loading of three samples of approximately 11–14 mg using well known methods. Analysis determined the loading to be approximately 0.105 mmol/g.

desired OL6 PNA capture probe suitable for use in Experiment 8, below.

Example 8

Capture Assay in the Presence and Absence of Blocking Probes

Preparation of Nucleic Acid Targets:

*Neisseria gonorrhoeae* (N.g.) and *Neisseria meningitidis* (N.m.) 16S rDNAs were obtained from Dako (Copenhagen, Denmark) and then amplified using the polymerase chain reaction (PCR). The nucleotide sequence of the forward and reverse primers are reported below. Pyrococcus furiosus (Pfu) DNA polymerase was used in the PCR amplification. Each of the two 16S rDNA amplimers were approximately 1500 base pairs in length. The 16S rDNA amplimers were then cloned into the transcription vector pGEM-4Z (Promega Corp., Madison, Wis.) using standard methods such that transcription from the T7 promotor yields the 16S rRNA sequence. Regions within the 16S rDNA clones of the N.g. and N.m. clones were then sequenced using the CircumVent Phototope thermal cycling kit (New England Biolabs Inc., Beverly, Mass.). The sequence information obtained was then compared with the data available in GenBank to confirm that the PCR amplification reactions had not misincorporated any nucleotides.

Biotin-labeled 16S rRNA transcripts of N.g. and N.m. were then prepared in vitro using T7 RNA polymerase and the RiboMax transcription kit (Promega Corp., Madison, Wis.). A ratio of 3 parts uridine triphosphate (UTP) to 1 part biotin-21-UTP (Clontech Laboratories, Inc., Palo Alto, Calif.) was used in 18 hr reactions. The DNA template was then digested with DNase and protein was removed by LiCl precipitation. The unincorporated nucleotides were then removed by size exclusion chromatography on a Bio-Spin P30 column (Bio-Rad). The purified transcripts were quantitated by ultraviolet (UV) absorption at 260 nm. The transcripts were stored in 10 mM Tris pH 8, 1 mM EDTA at −20° C.

PCR Primers Used to Prepare the Amplimers:

```
Forward:    5'    HO-CCG-AAT-TCG-TCG-ACA-ACA-GAG-TTT-         SEQ ID NO: 13
primer                 GAT-CMTGGC-TCA-G-OH              3'

Reverse:    5'    HO-CCC-GGG-ATC-CAA-GCT-TAA-GGA-GGT-         SEQ ID NO: 14
primer                      GWT-CCA-RCC-OH             3'
M = 1 to 1 ratio of A & C, R = 1 to 1 ratio of A & G, and W = 1 to 1 ratio of A & T
```

Experiment C: Synthesis Of PNA Capture Probe:

Capture Section of Target Nucleic Acid Sequences:
*Neisseria gonorrhoeae* (N.g.) 16S rRNA Target Sequence

```
5'   HO-TGG-CGA-AGG-CAG-CCU-CCU-GGG-AUA-ACA-CUG-         SEQ ID NO: 15
                  ACG-UUC-AUG-UC-OH           3'
```

*Neisseria meningitidis* (N.m.) 16S rRNA Target Sequence

```
5'   HO-TGG-CGA-AGG-CAG-CCU-CCU-GGG-ACA-ACA-CUG-         SEQ ID NO: 16
                  ACG-UUC-AUG-UC-OH           3'
```

The synthesis support prepared as described in Example B, above, was then packed into a standard PNA synthesis column. PNA synthesis was performed using standard commercially available instrumentation and reagents. The deprotection and purification of the PNA was also performed using standard methodologies. The PNA synthesis gave the Capture Probe/Target Site:
The PNA capture probe, OL6, which is complementary to positions 740–754 in the N.g. 16S rRNA sequence, was prepared using commercially available chemistry and reagents, except that the PNA probe was C-terminally labeled with 4-aminobenzoic acid as described in Example 7. Within the capture site, the N.g. and N.m. targets are related as a point mutation wherein the uracil residue at position 747 in N.g. is replaced by a cytosine residue in N.m. Consequently, the capture PNA probe, OL6, would comprise a single base mismatch when hybridizing to the 16S rRNA of N.m. target (FIG. 7).

PNA Blocker Probes:

A PNA 15-mer homologous to the capture site of the 16S rRNA N.m. target was synthesized (FIG. 7) using commercially available instrumentation and reagents. Similarly, a PNA 15-mer homologous to the capture site of 16S rRNA N.g. was synthesized (FIG. 7) using commercially available instrumentation and reagents. Consequently, these PNA blocker probes are related in that they specifically hybridize with the N.g. and N.m. capture sites wherein the N.g. and N.m. capture sites are related as point mutations.

to use, this solution was removed and each of the wells was washed twice with Wash Buffer 1 and twice with DEPC dH₂O.

Assay Method:

Each of the wells in the microtitre plates were equilibrated by incubation with 100 μL of Hybridization Buffer (100 mM NaCl, 100 mM Tris pH 7.4, 20 mM EDTA, 50% formamide and 0.5% Triton X-100) for 15 min. at 50° C., immediately before use in the capture assay. This buffer was then discarded.

To perform the hybridization, a set of microtubes (supported in an 8×12 rack) containing hybridization buffer and the various amounts of biotin-labeled N.g. or N.m. target (0.17 pmole to 0.17 fmole in half log dilutions) were incubated, in the presence and absence, of 1.7 pmole of either of the N.m. or N.g. PNA blocker probe. The incubation of each of these hybridization reactions was allowed to proceed for 30 min. at 50° C.

PNA Probe Sequences:

```
OL6            N         Ac-CAG-TGT-TAT-CCC-AGG-(linker)₂-K(P)-NH₂   C
N.g. blocker   N         H-(linker)₂-CAG-TGT-TAT-CCC-AGG-NH₂          C
N.m. blocker   N            H-CAG-TGT-TGT-CCC-AGG-NH₂                 C
```

The PNA probes are illustrated from the amino terminus (N) to the carboxyl terminus (C). The illustration "Ac" designates that the amine terminus has been capped with an N-acetyl group. The illustration "linker" designates the presence of the Expedite PNA linker (P/N GEN063032). The letter "P" illustrates the 4-aminobenzoic acid moiety which is attached to the ε-amino group of the lysine amino acid moiety "K".

Preparation Of Microtitre Plates Comprising Capture Probe:

The arylamine (4-aminobenzoic acid) at the 3' terminus of the PNA capture probe was reacted with the commercially available tresyl-activated dextran coated AquaBind microtiter plates (M&E Corp., Copenhagen, Denmark). The covalent immobilization of a PNA capture probe to the microtiter plate generates a surface suitable for the specific hybridization of nucleic acid sequences.

It was experimentally determined that addition of 150 pmole of PNA capture probe (OL6) to each well in the microtitre plate produced the optimal specificity and kinetics of capture of the 16S rRNA targets. Consequently, to each well in the microtitre plate was added a solution containing 150 pmole of PNA capture probe (OL6) in 100 μL of 0.1 M carbonate buffer pH 9.62. The reaction of the capture probe and the tresyl activated Aquabind microtitre well was allowed to proceed for 2 hours at 25° C., with shaking. The PNA capture probe solution was then removed and the wells were washed four times with Wash Buffer 1 (0.01 M phosphate pH 7.2, 2.7 mM KCl, 0.5M NaCl and 1% (v/v) Triton X-100). Each of the wells was then washed twice with diethyl pyrocarbonate treated deionized water (DEPC-dH₂O). Tresyl groups which may not have reacted during the coupling reaction were quenched by treating each well with 100 μL of a solution containing 5% 2-(2-Aminoethoxy) ethanol (AEE) pH 10. This quenching reaction was performed for 15 min. at 25° C., with shaking. The AEE solution was then removed and each of the wells was washed twice with DEPC dH₂O. The wells were then treated to block the surfaces from non-specific interaction, by the addition of 300 μL of a solution containing 1% diethyl pyrocarbonate treated casein (Boehringer Mannheim, Indianapolis, Ind.) and 0.1 M carbonate buffer pH 9.62. This reaction was allowed to proceed for at least 2 hours at 25° C., with shaking. The plates were then stored at 10° C. without removing the solution containing 1% diethylpyrocarbonate treated casein (Boehringer Mannheim, Indianapolis, Ind.) and 0.1 M carbonate buffer pH 9.62. Prior After 30 min., the contents of each of the hybridization reactions was transferred from each of the microtubes to a specific well in the microtiter plate comprising the OL6 capture probe immobilized to the well surface. The capture reaction was allowed to proceed for 30 min. at 50° C., with shaking. The solutions in each of the wells was then discarded. Any, residual unhybridized target was then removed by washing once with hybridization buffer and four times with THT buffer (50 mM Tris pH 7.4, 100 mM NaCt and 0.1% Tween 20) both at 50° C.

The biotinylated N.g or N.m. target nucleic acid which was still present in each of the wells of the microtitre plate was detected using a Streptavidin/HRP conjugate (DAKO Corp. USA). The Streptavidin/HRP conjugate was diluted 1:5000 in THT buffer and each well in the microtitre plate was treated with 100 μL of the diluted stock for 30 minutes at 25° C., with shaking. Each of the wells was then washed five times with THT to remove any excess conjugate. To each well was then added 100 μL of 3,3', 5,5' tetramethyl benzidine (TMB+) (DAKO Corp., USA). This reagent was allowed to react for 15 minutes at 37° C. and then the reaction was terminated by addition of an equal volume of 0.5 M H₂SO₄. The color which was generated (absorbance at 450 nm) was then measured in a microplate reader (Molecular Devices Corp., Menlo park, Calif.).

Assay Design:

FIG. 8A is a plate schematic of the configuration of hybridization reactions performed in the wells of the microtiter plates used for this experiment. For convenience the rows of the figure have been designated with the letters A–H and the columns have been designated with the numbers 1–12. As illustrated in the figure, the reactions performed in the wells in columns 1, 2, 5, 6, 9, and 10 contained various amounts of N. gonorrhoeae target. Similarly, as illustrated in the figure, the reactions performed in wells in columns 3, 4, 7, 8, 11 and 12 contained various amounts of N. meningitidis target. As illustrated in the figure, for both the N.g. and N.m. containing reactions, the amount of target sequence present in the wells varied between 170 fmole and 0.17 fmole. Reactions performed in the wells in row H contained no target and the values obtained for these reactions were used as the assay background. The reactions performed in the wells in columns 1 through 4 contained no PNA blocker probe. The reactions performed in the wells in columns 5 through 8 contained 1.7 pmole of PNA blocker which was complementary to the N.g. target. The reactions performed in the wells in columns 9 through 12 contained 1.7 pmole of PNA blocker which was complementary to the N.m. target. Each of the conditions examined was performed in duplicate and, unless otherwise noted, the results were averaged to generate the derived data.

Results:

With reference to FIG. 8B, the derived data for each of the experimental conditions is presented. Unless otherwise indicated, the data at each target level represents the average of the two data points collected after the appropriate averaged background has been subtracted. (Of 96 data points, 3 data points were not included in the analysis since these were clearly erroneous). Though all the derived data which was acquired in the experiment is presented in the figures, essentially all the data for target levels below 5.4 fmole gave data points which were not significantly above background to be considered to be reliable or statistically significant. Consequently, only the data obtained for target levels greater than 5.4 fmole are discussed in this section.

With reference to FIG. 8C, a comparison of the percent decrease in capture of the target which is attributable to the presence of blocking probe is presented. Thus, all data in FIG. 8C is derived from data in FIG. 8B. For example, column A represents the percent decrease in capture of the N.g. target in the presence of the N.m blocker probe. Consequently, the percent decrease of 38.3 reported in FIG. 8C, column A for the target level of 170 fmole is determined by subtracting the value in FIG. 8B, in columns A and C and then dividing that difference by the value in FIG. 8B, column A.

Columns A and B in FIG. 8B contain data for the signal (absorbance 450 nm) resulting from capture of the N.g. and N.m. transcripts in the absence of PNA blocker probe. The data demonstrates that the signal generated in the presence of 5.4 fmole of N.g. target is approximately equivalent to signal generated in the presence of 0.17 pmole of N.m. target. Therefore, the discrimination between N.g. and N.m., in the absence of blocker probe, is approximately 1–1.5 logs.

With reference to FIG. 8B, columns C and D present the data for the signal (absorbance 450 nm) resulting from capture of the N.g. and N.m. transcripts in the presence of 1.7 pmole of PNA blocker probe which is homologous to the N.m. capture site (the N.m. blocker probe). At all target levels above 5.4 fmole, there is a measurable decrease in the capture of both the N.m. and N.g. targets as compared with the absence of the N.m. blocker probe (Compare: data in FIG. 8B, column A with C and data in FIG. 8B, column B with column D, respectively) However, as can be seen by comparison of the relative percent decrease in capture of the different targets in the presence of the N.m. blocker probe (data in FIG. 8C) there is a much greater decrease in capture of the N.m. target. For the three highest target levels, the average decrease in capture of the N.m. target in the presence of the N.m. blocker probe was 69% while the average decrease in the capture of the N.g. target was only 31%.

Therefore, under the conditions of this assay, addition of 1.7 pmole of N.m. blocker probe improved discrimination between N.g. and N.m. by approximately two fold.

With reference to FIG. 8B, columns E and F present the data for the signal (absorbance 450 nm) resulting from capture of the N.g. and N.m. transcripts in the presence of 1.7 pmole of PNA blocker probe which is homologous to the N.g. capture site (the N.g. blocker probe). At all target levels above 5.4 fmole, there is a significant decrease in the capture of the N.g. target as compared with the absence of the N.g. blocker probe (Compare: data in FIG. 8B, column A with E) However, as can be seen by comparison of the relative percent decrease in capture of the different targets in the presence of the N.g. blocker probe (data in FIG. 8C) there is a much greater decrease in capture of the N.g. target. Thus, for the three highest target levels, the average decrease in capture of the N.g. target in the presence of the N.g. blocker probe was 86% while the decrease in the capture of the N.m. target was minimal (only 16% for the highest target level; See: FIG. 8C, column D).

In summary, the data in FIGS. 8B and 8C demonstrate that it is possible to improve the selective inhibition of capture of a target sequences containing a point mutation on a hybridization surface composed of PNA capture probe when blocking probes are used in the hybridization assay.

Figures 8D, 8E:
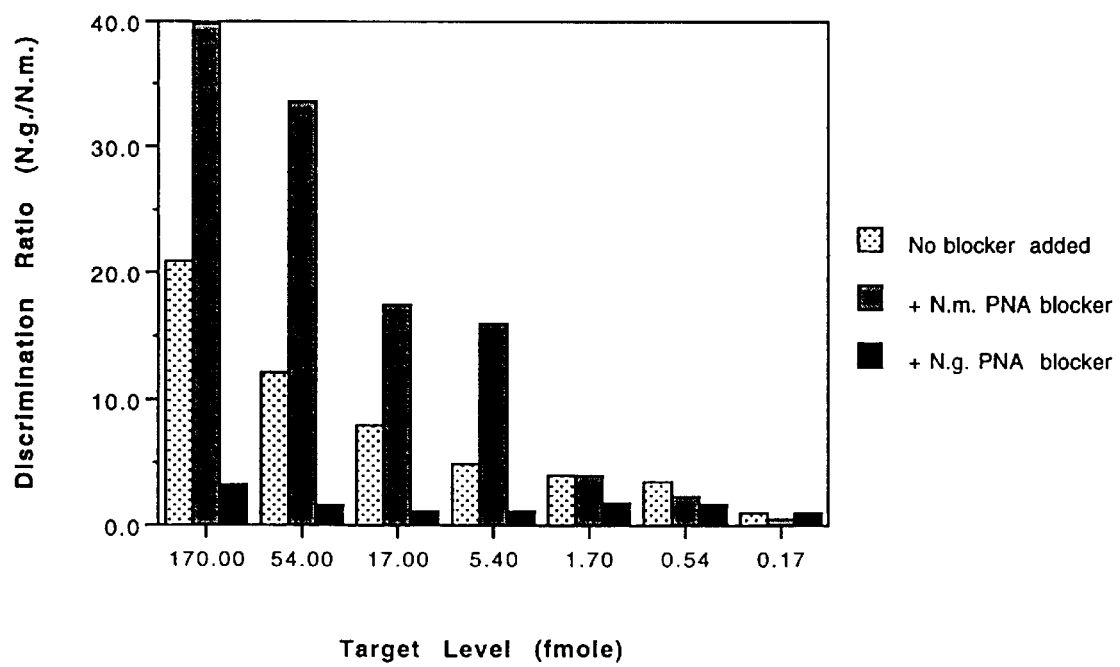
FIG. 8D is a tabular illustration of hybridization assay data.
FIG. 8E is a graphical illustration of hybridization assay data.

The discrimination ratios which are presented in FIG. 8D are derived from the data in FIG. 8B. When considering the data for only the three highest target levels examined (170–17 fmole), the discrimination ratios in the absence of PNA blocker probe are 21, 12 and 8 (See FIG. 8D, column A). In the presence of 1.7 pmole of N.m. blocker probe, the discrimination ratios for the capture of the N.m. target were increased from 21 to 40, from 12 to 34 and from 8 to 18, respectively (Compare: columns A and B). Consequently, the overall improvement in point mutation discrimination was two to three fold greater under the conditions examined.

In the presence of 1.7 pmole of N.g. blocker probe, the discrimination ratios for the capture of the N.g. target were 3, 1.6 and 1.1 at the three highest target levels examined (See: column C). This data demonstrates that, under the conditions examined, it is necessary to add PNA blocker in at least 30 fold molar excess to the amount of target present to thereby completely eliminate the capture of the N.g. target. This is evident since the discrimination ratio approaches the value of 1 when the signal for N.g. and N.m. approaches equivalent low levels.

FIG. 5E is a graphical illustration of the data in FIG. 8D. The graphical illustration is presented as a useful and quick means to visually analyze and compare the tabular data.

Summary:

A discrimination in a capture assay can be substantially improved by addition of blocking probes, which are designed to hybridize to non-target sequences which are closely related to the target of interest.

We claim:

1. A method for suppressing the binding of a detectable probe to a non-target sequence in an assay of a sample for a target sequence, the method comprising the steps of:

a. contacting the sample with a set containing two or more probes under conditions suitable for the probes to hybridize to nucleic acid, wherein, at least one of said probes is a detectable probe labeled with a detectable moiety and having a sequence complementary or substantially complementary to the target sequence, and at least one of the other probes is an unlabeled or independently detectable probe having a sequence complementary or substantially complementary to a non-target sequence which may be present in the sample; provided that at least one of the detectable probe and the unlabeled or independently detectable probe is a PNA probe; and b. detecting the presence or amount of target sequence present in the sample by directly or indirectly detecting or quantitating the detectable moiety of said detectable probe which hybridized to the target sequence.

2. The method of claim 1, wherein all probes of the set are PNA probes.

3. The method of claim 1, wherein the target sequence is DNA or RNA.

4. The method of claim 1, wherein the target sequence is immobilized to a surface.

5. The method of claim 4, further comprising the step of:

c. collecting an aliquot, by elution from the surface, containing any of the one or more detectable probes which hybridized to target sequence when performing step (a.).

6. The method of claim 5, wherein each of the detectable probes, having a distinct sequence, comprise independently detectable moieties which are used to identify or quantitate the presence or amount of each distinct probe sequence present in the aliquot collected.

7. The method of claim 6, wherein the detectable moiety of the detectable probe is a mass marker and the identity of each distinct probe in the aliquot is determined by mass analysis using Positive-ion Fast Atom Bombardment Tandem Mass Spectrometry.

8. The method of claim 1, wherein target and non-target sequences are closely related sequences.

9. The method of claim 8, wherein target sequence and the non-target sequence are related as a point mutation.

10. The method of claim 1, wherein the assay is used to detect, identify, or quantitate the presence or amount of an organism or virus in the sample.

11. The method of claim 1, wherein the assay is used to detect, identify, or quantitate the presence or amount of one or more species of an organism in the sample.

12. The method of claim 1, wherein the assay is used to determine the effect of antimicrobial agents on the growth of one or more microorganisms in the sample.

13. The method of claim 1, wherein the assay is used to determine the presence or amount of a taxonomic group of organisms in the sample.

14. The method of claim 1, wherein each of the different detectable PNA probes of the set comprise independently detectable moieties.

15. The method of claim 1, wherein the detectable moiety is selected from the group consisting of a chromophore, a fluorochrome, a spin label, a radioisotope, an enzyme, a hapten and a chemiluminescent compound.

16. The method of claim 15, wherein the enzyme is selected from the group consisting of alkaline phosphatase, soybean peroxidase and horseradish peroxidase.

17. The method of claim 15, wherein the hapten is selected from the group consisting of fluorescein, biotin, 2,4-dinitrophenyl and digoxigenin.

18. The method of claim 1, wherein step (a.) comprises i.) incubating the sample with at least one unlabeled or independently detectable probe having a sequence complementary or substantially complementary to a non-target sequence which may be present in the sample for a first period of time under conditions suitable for probes to hybridize to nucleic acid; and ii.) incubating the sample with the at least one detectable probe labeled with a detectable moiety and having a sequence complementary or substantially complementary to a target sequence for a second period of time, under conditions suitable for probes to hybridize to nucleic acid.

19. The method of claim 18, wherein;

i.) each of the first period of time and the second period or time is twenty minutes or less;

ii.) at least one detectable probe is a PNA probe; and iii.) at least one unlabeled or independently detectable probe is a PNA probe.

20. The method of claim 1, wherein the ratio of unlabeled or independently detectable probe to detectable probe is at least two to one.

21. A method for suppressing the binding of a non-target sequence to a capture probe immobilized on a surface in a capture assay of a sample for a target sequence of a nucleic acid target molecule, the method comprising the steps of:

a. contacting the sample with a solution containing one or more blocking probes under conditions suitable for the blocking probes to hybridize to nucleic acid, wherein the blocking probes are complementary or substantially complementary to one or more non-target sequences which may be present in the sample;

b. contacting the sample with the capture probe immobilized on a surface under conditions suitable for the target sequence, if present, to hybridize to the capture probe, wherein the capture probe is complementary or substantially complementary to the target sequence and thereby forms a capture probe/target sequence complex; provided that at least one of a blocking probe or a capture probe is a PNA probe; and c. detecting the presence or amount of nucleic acid target molecule immobilized to the surface.

22. The method of claim 21, wherein the target nucleic acid molecule is DNA or RNA.

23. The method of claim 21, wherein all probes are PNA probes.

24. The method of claim 21, wherein the target and the non-target sequences are related as a point mutation.

25. The method of claim 21, wherein the surface comprises an array of probes, wherein each distinct probe sequence in the array is designed to capture a specific nucleic acid target molecule, the presence or quantity of which is indicative of the presence or quantity of a specific organism, virus, fungi or disease state of interest in the sample.

26. The method of claim 21, wherein the presence or amount of nucleic acid target molecule immobilized to the surface is detected using a labeled antibody which specifically interacts with the capture probe/target sequence complex which is formed on the surface.

27. The method of claim 26, wherein the labeled antibody is a labeled anti-nucleic acid/nucleic acid antibody which detects the presence of the capture probe/target sequence complex which is formed by hybridization of the capture probe to the target sequence.

28. The method of claim 27, wherein the labeled antibody is labeled with a detectable moiety selected from the group consisting of a chromophore, a fluorophore, a spin label, a radioisotope, an enzyme, a hapten and a chemiluminescent compound.

29. The method of claim 26, wherein the labeled antibody is a labeled anti-PNA/nucleic acid antibody which detects the presence of the capture probe/target sequence complex which is formed by hybridization of the PNA capture probe to the target sequence.

30. The method of claim 29, wherein the labeled antibody is labeled with a detectable moiety selected from the group consisting of a chromophore, a fluorophore, a spin label, a radioisotope, an enzyme, a hapten and a chemiluminescent compound.

31. The method of claim 30, wherein the enzyme is selected from the group consisting of alkaline phosphatase, soybean peroxidase and horseradish peroxidase.

32. The method of claim 30, wherein the hapten is selected from the group consisting of fluorescein, biotin, 2,4-dinitrophenyl and digoxigenin.

33. The method of claim 21, wherein the presence or amount of target sequence immobilized to the surface is detected using a detector probe which hybridizes to a second target sequence of the nucleic acid target molecule.

34. The method of claim 33, wherein the method of claim 1 is used to suppress the binding of detector probe to a non-second target sequence.

35. The method of claim 33, wherein the detector probe is labeled with a detectable moiety selected from the group consisting of a chromophore, a fluorophore, a spin label, a radioisotope, an enzyme, a hapten and a chemiluminescent compound.

36. The method of claim 33, wherein the detector probe is a nucleic acid probe and the presence or quantity of hybridized detector probe is detected using a labeled anti-nucleic acid/nucleic acid antibody.

37. The method of claim 33, wherein the detector probe is a PNA probe and the presence or quantity of hybridized detector probe is detected using a labeled anti-PNA/nucleic acid antibody.

38. The method of claim 21, wherein the capture assay is used to detect, identify, or quantitate the presence or amount of an organism or virus in the sample.

39. The method of claim 21, wherein the assay is used to detect, identify, or quantitate the presence or amount of one or more species of an organism in the sample.

40. The method of claim 21, wherein the assay is used to determine the effect of antimicrobial agents on the growth of one or more microorganisms in the sample.

41. The method of claim 21, wherein the assay is used to determine the presence or amount of a taxonomic group of organisms in the sample.

* * * * *

UNITED STATES PATENT AND TRADEMARK OFFICE
CERTIFICATE OF CORRECTION

PATENT NO. : 6,962,778 B1
APPLICATION NO. : 09/545084
DATED : November 8, 2005
INVENTOR(S) : James M. Coull et al.

Page 1 of 1

It is certified that error appears in the above-identified patent and that said Letters Patent is hereby corrected as shown below:

Column 55,
Line 66, delete "a." and replace with -- a) --;

Column 57,
Line 6, delete "b." and replace with -- b) --;
Line 17, delete "c." and replace with -- c) --;
Line 60, delete "i.)" and replace with -- i) --;
Line 66, delete "ii.)" and repalce with -- ii) --;

Column 58,
Line 6, delete "i.)" and replace with -- i) --;
Line 8, delete "ii.)" and replace with -- ii) --;
Line 9, delete "iii.)" and replace with -- iii) --;
Line 18, delete "a." and replace with -- a) --;
Line 24, delete "b." and replace with -- b) --;
Line 32, delete "c." and replace with -- c) --.

Signed and Sealed this

Twentieth Day of June, 2006

JON W. DUDAS
*Director of the United States Patent and Trademark Office*

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence

```
<220> FEATURE:
<221> NAME/KEY: misc_feature
<222> LOCATION: (1)
<223> OTHER INFORMATION: 5'-BIOTIN
<220> FEATURE:
<223> OTHER INFORMATION: Description of Artificial Sequence: Synthetic
      oligonucleotide

<400> SEQUENCE: 1
gtggtagttg gagctggtgg cgta                                             24

<210> SEQ ID NO 2
<211> LENGTH: 24
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-BIOTIN
<220> FEATURE:
<223> OTHER INFORMATION: Description of Artificial Sequence: Synthetic
      Oligonucleotide

<400> SEQUENCE: 2
gtggtagttg gagcttgtgg cgta                                             24

<210> SEQ ID NO 3
<211> LENGTH: 31
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-BIOTIN
<220> FEATURE:
<223> OTHER INFORMATION: Description of Artificial Sequence: Synthetic
      Oligonucleotide

<400> SEQUENCE: 3
gtggtagttg gagctggtgg cgtaggcaag a                                     31

<210> SEQ ID NO 4
<211> LENGTH: 31
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-BIOTIN
<220> FEATURE:
<223> OTHER INFORMATION: Description of Artificial Sequence: Synthetic
      Oligonucleotide

<400> SEQUENCE: 4
gtggtagttg gagcttgtgg cgtaggcaag a                                     31

<210> SEQ ID NO 5
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-FLUORESCEIN
<220> FEATURE:
<223> OTHER INFORMATION: Description of Artificial Sequence: Synthetic
      Oligonucleotide

<400> SEQUENCE: 5
acgccaccag ctcca                                                       15
```

```
<210> SEQ ID NO 6
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-FLUORESCEIN
<220> FEATURE:
<223> OTHER INFORMATION: Description of Artificial Sequence: Synthetic
      Oligonucleotide

<400> SEQUENCE: 6
acgccacaag ctcca                                                       15

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-FLUORESCEIN
<220> FEATURE:
<223> OTHER INFORMATION: Description of Artificial Sequence: Synthetic
      Oligonucleotide

<400> SEQUENCE: 7
tgcctacgcc accagctcca actac                                            25

<210> SEQ ID NO 8
<211> LENGTH: 25
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-FLUORESCEIN
<220> FEATURE:
<223> OTHER INFORMATION: Description of Artificial Sequence: Synthetic
      Oligonucleotide

<400> SEQUENCE: 8
tgcctacgcc acaagctcca actac                                            25

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 9
acgccaccag ctcca                                                       15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 10
acgccacaag ctcca                                                       15
```

```
<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 11
tgcctacgcc accagctcca actac                                              25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 12
tgcctacgcc acaagctcca actac                                              25

<210> SEQ ID NO 13
<211> LENGTH: 37
<212> TYPE: DNA
<213> ORGANISM: Neisserian gonorrheae

<400> SEQUENCE: 13
ccgaattcgt cgacaacaga gtttgatcmt ggctcag                                 37

<210> SEQ ID NO 14
<211> LENGTH: 33
<212> TYPE: DNA
<213> ORGANISM: Neisserian gonorrheae

<400> SEQUENCE: 14
cccgggatcc aagcttaagg aggtgwtcca rcc                                     33

<210> SEQ ID NO 15
<211> LENGTH: 41
<212> TYPE: DNA
<213> ORGANISM: Neisserian gonorrheae
<220> FEATURE:
<223> OTHER INFORMATION: Description of Combined DNA/RNA Molecule:
      Clone: PdNg-1

<400> SEQUENCE: 15
tggcgaaggc agccuccugg gauaacacug acguucaugu c                            41

<210> SEQ ID NO 16
<211> LENGTH: 41
<212> TYPE: DNA
<213> ORGANISM: Neisserian meningitidis
<220> FEATURE:
<223> OTHER INFORMATION: Description of Combined DNA/RNA Molecule:
      CLONE: Pdnm-1

<400> SEQUENCE: 16
tggcgaaggc agccuccugg gacaacacug acguucaugu c                            41
```